US008568580B2

(12) United States Patent
Vann et al.

(10) Patent No.: US 8,568,580 B2
(45) Date of Patent: Oct. 29, 2013

(54) SYSTEMS AND METHODS FOR ISOLATING NUCLEIC ACIDS

(75) Inventors: Charles S. Vann, El Granada, CA (US); Maxim G. Brevnov, Union City, CA (US); David W. Ruff, San Francisco, CA (US); Kenneth J. Livak, San Jose, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1184 days.

(21) Appl. No.: 12/179,455

(22) Filed: Jul. 24, 2008

(65) Prior Publication Data

US 2009/0071830 A1 Mar. 19, 2009

Related U.S. Application Data

(60) Provisional application No. 60/961,795, filed on Jul. 24, 2007, provisional application No. 61/039,026, filed on Mar. 24, 2008.

(51) Int. Cl.
*G01N 27/453* (2006.01)
*B01D 61/42* (2006.01)

(52) U.S. Cl.
USPC ............ 204/627; 204/518; 204/606; 204/614

(58) Field of Classification Search
USPC ................. 204/665, 518–545, 627–640, 600; 436/49, 43
See application file for complete search history.

(56) References Cited

U.S. PATENT DOCUMENTS 3,873,433 A * 3/1975 Seidel et al. .................. 204/462
4,650,982 A 3/1987 Ando
4,863,582 A 9/1989 Wijangco
5,885,430 A * 3/1999 Kernan et al. ................. 204/453
5,993,611 A * 11/1999 Moroney et al. ........... 204/157.6

(Continued)

FOREIGN PATENT DOCUMENTS

| | | |
|---|---|---|
| WO | 98/10277 A | 3/1998 |
| WO | 00/50870 A | 8/2000 |
| WO | 01/10470 A | 2/2001 |

OTHER PUBLICATIONS

International Search Report for application No. PCT/US2008/071071 dated Sep. 4, 2008, along with the Written Opinion of the International Searching Authority.

*Primary Examiner* — Luan Van
*Assistant Examiner* — Steven Rosenwald

(57) ABSTRACT

A system for collecting target nucleic acids from a sample can include at least one sample chamber configured to receive a sample containing target nucleic acids and other material, at least one collection chamber removably mountable relative to the at least one sample chamber and configured to collect target nucleic acids separated from the other material, a filter removably mountable relative to the at least one sample chamber and configured to be disposed between the at least one sample chamber and the at least one collection chamber when the at least one collection chamber is mounted relative to the at least one sample chamber. The system may further include a pair of electrodes configured to generate an electric field sufficient to cause target nucleic acids in the at least one sample chamber to migrate via electrophoresis from the at least one sample chamber through the filter into the at least one collection chamber, wherein the filter may be configured to permit passage of target nucleic acids and to block passage of material of a size larger than the target nucleic acids.

17 Claims, 33 Drawing Sheets

(56) References Cited

U.S. PATENT DOCUMENTS 6,129,828 A * 10/2000 Sheldon et al. ............... 204/518
7,169,279 B2 * 1/2007 King et al. .................... 204/601
2002/0092767 A1 * 7/2002 Bjornson et al. .............. 204/451
2006/0144707 A1 7/2006 Landers

* cited by examiner

SYSTEMS AND METHODS FOR ISOLATING NUCLEIC ACIDS

CROSS-REFERENCE TO RELATED APPLICATIONS

This application claims priority to U.S. Provisional Application No. 60/961,795, filed Jul. 24, 2007 and to U.S. Provisional Application No. 61/039,026, filed Mar. 24, 2008, both of which are hereby incorporated by reference herein in their entireties.

TECHNICAL FIELD

The present teachings relate to systems and methods for isolating and collecting nucleic acids from a sample. The present teachings also relate to systems and methods for isolating and collecting target nucleic acids from a sample containing differing cell types.

INTRODUCTION

The section headings used herein are for organizational purposes only and are not to be construed as limiting the subject matter described in any way.

Nucleic acid extraction and isolation from cells and other entities containing nucleic acids is important in a variety of settings. In many applications, to detect the presence and/or type, and/or otherwise perform analysis, of nucleic acids in a sample first requires isolation of the nucleic acids from the remainder of the contents of the sample (e.g., cell debris and/or other impurities, proteins, etc.). Under some conventional techniques, extraction, isolation, and collection of nucleic acids involve manual operation steps that may be expensive and/or time-consuming.

In forensics, for example, identifying the source of cells collected at a crime scene or other location can be accomplished by separating nucleic acids from a sample of collected material (e.g., a sample containing cells) and detecting, such as by polymerase chain reaction, the nucleic acids that are separated. Some methods conventionally used to isolate target nucleic acids include processing several small amounts of collected sample (e.g., several Eppendorf tubes of collected sample) by, for example, centrifuging the sample; capturing the nucleic acids from the sample on a binding medium; separating the binding medium with the captured nucleic acids from the remainder of the sample, by, for example, rinsing or washing; eluting the captured nucleic acids; and detecting the eluted nucleic acids. Such methods often involve processing one or a limited number of tubes at a time, making the procedure relatively time-consuming.

Detecting pathogens in food using some conventional techniques also is a time-consuming process. For example, a sample of food suspected of containing a pathogen (e.g., bacteria) may be placed in a medium that allows the pathogen to grow and, after sufficient time has elapsed, be observed and cultured to determine the existence of or type of pathogen. That growth and detection process can take several hours, for example, up to at least 8 hours. This is in part because there may be a single pathogen or limited number pathogens (e.g., bacteria cells) in a relatively large sample size.

It may be desirable, therefore, to provide a technique that permits relatively rapid isolation and collection of target nucleic acids from a sample. It also may be desirable to provide a technique for isolating and collecting target nucleic acids from a sample that yields an amount of collected target nucleic acids suitable for performing detection via conventional nucleic acid detection techniques, such as, for example, polymerase chain reaction (PCR).

More generally, it may be desirable to automate sample preparation, including nucleic acid extraction, isolation, and/or collection, for example, to achieve greater efficiency when preparing samples for further analysis.

SUMMARY OF EXEMPLARY EMBODIMENTS

The present teachings may satisfy one or more of the above-mentioned desirable features. Other features and/or advantages may become apparent from the description which follows.

According to various embodiments, the present teachings include a system for collecting target nucleic acids from a sample, the system comprising at least one sample chamber configured to receive a sample containing target nucleic acids and other material, at least one collection chamber removably mountable relative to the at least one sample chamber and configured to collect target nucleic acids separated from the other material, and a filter removably mountable relative to the at least one sample chamber and configured to be disposed between the at least one sample chamber and the at least one collection chamber when the at least one collection chamber is mounted relative to the at least one sample chamber. The system may further comprise a pair of electrodes configured to generate an electric field sufficient to cause target nucleic acids in the at least one sample chamber to migrate via electrophoresis from the at least one sample chamber through the filter into the at least one collection chamber. The filter may be configured to permit passage of target nucleic acids and to block passage of material of a size larger than the target nucleic acids.

According to yet other exemplary embodiments, the present teachings contemplate a system for collecting target nucleic acids from a sample, the system comprising at least one sample chamber configured to receive a sample containing target nucleic acids and at least one electrophoresis matrix comprising at least one collection chamber and at least one filter, the at least one electrophoresis matrix configured to be removably mountable relative to the at least one sample chamber such that the at least one filter is disposed between the at least one sample chamber and the at least one collection chamber. The system may further comprise a pair of electrodes configured to generate an electric field sufficient to cause target nucleic acids in the at least one sample chamber to migrate via electrophoresis from the at least one sample chamber through the filter and into the at least one collection chamber.

According to various exemplary embodiments, the present teachings may include a method for collecting target nucleic acids from a sample, the method comprising subjecting entities containing target nucleic acids in a sample contained in at least one chamber to disruption to release the target nucleic acids from the entities, migrating via electrophoresis at least some of the target nucleic acids released from the entities from the at least one chamber through a filter to at least one collection chamber in flow communication with the at least one chamber, blocking migration via electrophoresis through the filter of material of larger size than the target nucleic acid that is in the at least one chamber, and removing the at least some target nucleic acids from the at least one collection chamber.

According to yet other exemplary embodiments, the present teachings include a method for collecting pathogen nucleic acids, the method comprising subjecting at least one pathogen in a food product sample to disruption to release pathogen nucleic acids, separating the pathogen nucleic acids released from the at least one pathogen from other material in the sample by migrating via electrophoresis the pathogen nucleic acids through a filter, and collecting the pathogen nucleic acids that have moved through the filter.

According to various exemplary embodiments, the present teachings also contemplate a method of collecting nucleic acids from a sample, the method comprising disrupting a first type of entities in a sample that comprises a first type of entities containing nucleic acids and a second type of entities containing nucleic acids, wherein the disrupting releases a first type of nucleic acids from the first type of entities without disrupting the second type of entities. The method may further include causing migration via electrophoresis of at least some of the first type of nucleic acids through a filter to separate the at least some first type of nucleic acids from contents of the sample remaining after the disrupting of the first type of entities, disrupting the second type of entities in the sample to release a second type of nucleic acids from the second type of entities, and causing migration via electrophoresis of at least some of the second type of nucleic acids through a filter to separate at least some of the second type of nucleic acids from contents of the sample remaining after the disrupting of the second type of entities, and collecting the separated second type of nucleic acids.

In yet additional exemplary embodiments, the present teachings include a kit for collecting nucleic acids from a sample, the kit comprising a device comprising at least one chamber configured to receive a sample containing a first type of entities and a second type of entities, at least one collection chamber, and at least one filter configured to permit passage of material of a first size while blocking passage of material of a size larger than the first size. The kit may further comprise a first lysing reagent effective to lyse a first type of entities containing nucleic acids without lysing a second type of entities containing nucleic acids in a sample comprising the first type of entities and the second type of entities and a second lysing reagent effective to lyse the second type of entities.

Additional objects and advantages may be set forth in part in the description which follows, and in part will be obvious from the description, or may be learned by practice of the present teachings. Those objects and advantages will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various exemplary embodiments of the present teachings and together with the description, serve to explain certain principles.

In the drawings.

DESCRIPTION OF EXEMPLARY EMBODIMENTS

Figure 1A:
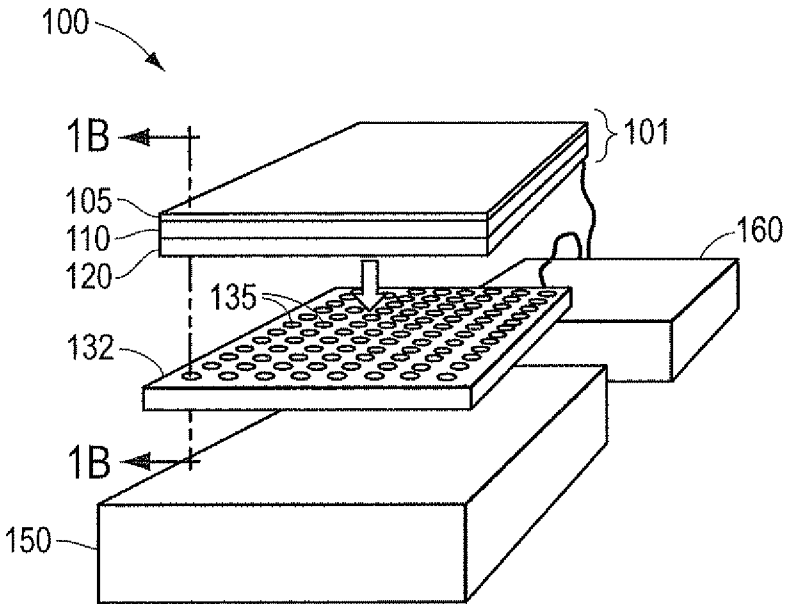
FIG. 1A is an isometric view of an exemplary embodiment of an electrophoresis-based sample preparation system in accordance with the present teachings.

Reference will now be made in detail to various exemplary embodiments, some of which are illustrated in the accompanying drawings. Wherever possible, the same reference numbers will be used throughout the drawings to refer to the same or like parts.

As used herein, "sample" is used to mean any biological substance that contains cells, including, for example, pathogen cells, matter contained in cells, other pathogens, including viral particles, and/or matter contained in viral particles. Samples also may contain the aforementioned materials mixed with other substances, such as, for example, buffers, reagents, and other substances that may react with the material or may be added to support a future reaction with the material.

The term "nucleic acid" can be used interchangeably with "polynucleotide" or "oligonucleotide" and can include single-stranded or double-stranded polymers of nucleotide monomers, including 2'-deoxyribonucleotides (DNA) and ribonucleotides (RNA) linked by internucleotide phosphodiester bond linkages, or internucleotide analogs, and associated counter ions, for example, H+, NH4+, trialkylammonium, Mg2+, Na+ and the like. A polynucleotide may be composed entirely of deoxyribonucleotides, entirely of ribonucleotides, or chimeric mixtures thereof. Polynucleotides may be comprised of nucleobase and sugar analogs. Polynucleotides typically range in size from a few monomeric units, for example, 5-40 when they are frequently referred to in the art as oligonucleotides, to several thousands of monomeric nucleotide units. Unless denoted otherwise, whenever a polynucleotide sequence is represented, it will be understood that the nucleosides are in 5' to 3' order from left to right and that "A" denotes deoxyadenosine, "C" denotes deoxycytidine, "G" denotes deoxyguanosine, and "T" denotes thymidine, unless otherwise noted. A labeled polynucleotide can comprise modification at the 5'terminus, 3'terminus, a nucleobase, an internucleotide linkage, a sugar, amino, sulfide, hydroxyl, or carboxyl. See, for example, U.S. Pat. No. 6,316,610 B2, which issued Nov. 13, 2001 and is entitled "LABELLED OLIGONUCLEOTIDES SYNTHESIZED ON SOLID SUPPORTS," which is incorporated herein by reference. Similarly, other modifications can be made at the indicated sites as deemed appropriate.

"Filter" or "filter material" as used herein may refer to any material through which it is possible to pass substances smaller or equal to a certain size while blocking the passage of other substances larger than that size. Filters or filter materials herein may therefore pass liquids, gases, and solids, but may be configured so as to exclude various materials from passage on the basis of size.

The term "meat" as used herein may refer to any edible portion of a variety of animals and/or fish and can include, but is not limited to, poultry, beef, pork, fish, ostrich, buffalo, venison, and virtually any other type of meat from an animal or fish intended for consumption.

The term "pathogens" as used herein may refer to any of a variety of pathogen cells or viral particles, wherein pathogen cells may include, but are not limited to, for example, molds, bacteria, protozoa, fungi, parasites, pathogenic proteins (e.g., prions). "Pathogen nucleic acids" as used herein may refer to nucleic acids from any of the pathogens included in the above definition.

As used herein, an "entity containing nucleic acid" and variants thereof may refer to pathogens (as defined above), other types of cells, and/or any other unit containing nucleic acids.

The term "disruption," "disrupting," "disrupt," and variants thereof, when used herein in the context of disrupting cells, pathogens, and/or other entities containing nucleic acids may include any process for effecting the release of nucleic acids from an entity containing nucleic acids. Such processes may include, for example, rupturing or otherwise breaching the membrane of a cell, including a pathogen cell, and/or the viral envelope and/or capsid of a viral particle to release nucleic acid contained therein. Also, it should be noted that reference to disrupted sample herein refers to a sample containing entities that have been subjected to disruption; similarly, reference to disrupted cells or pathogens, respectively refers to cells or pathogens that have been subjected to disruption.

Although many of the exemplary embodiments described utilizing chemical lysing to achieve disruption, it should be understood that any of a variety of disruption techniques known to those skilled in the art could be used in lieu of or in combination with the chemical lysing. Examples of suitable disruption techniques include, but are not limited to, thermal, electrical, and/or mechanical techniques. Mechanical techniques may include, for example, agitating the sample and cells therein by any of a variety of mechanisms, e.g, beads, vibration, sonication, and/or passing the sample through structures that may cause shearing of cells, pathogens, and/or other entities containing nucleic acids to rupture the outer boundaries of those entities. In various exemplary embodiments, disruption should not significantly break apart the nucleic acids so as to achieve filtering via size exclusion as desired. In the various exemplary embodiments described above, it is contemplated that a lysing reagent may be predeposited or added to the various chambers, as desired. Moreover, in various exemplary embodiments, reference is made to multiple lysing steps (e.g., 2 lysing steps), wherein a first lysing reagent is used in a first lysing step to disrupt a first type of entities containing nucleic acid without disruption of a second type of entities containing nucleic acid, and a subsequent (e.g., second) lysing reagent is used in a subsequent (e.g., second) lysing step to disrupt a second type of entities containing nucleic acid. In various exemplary embodiments, the subsequent (e.g., second) lysing reagent may also be effective to lyse the first type of entities in addition to lysing the second type of entities.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present teachings. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," and any singular use of any word, include plural referents unless expressly and unequivocally limited to one referent. Thus, for example, reference to "a biological sample" includes two or more different biological samples. As used herein, the term "include" and its grammatical variants are intended to be non-limiting, such that recitation of items in a list is not to the exclusion of other like items that can be substituted or added to the listed items.

Although detection of nucleic acids (and therefore the determination of the existence and/or type of such nucleic acids) from a sample can be relatively efficiently accomplished using detection techniques, such as, for example, PCR, in some applications, the size (e.g., volume) of a sample from which it is desired to determine the presence and/or kind of nucleic acids in the sample may not be conducive to such conventional detection methods. By way of example, in pathogen detection of a food sample, such as, for example a stomacked meat sample, the sample size may be relatively large (e.g., on the order of 25 grams of hamburger meat) with only one to a few pathogens present in some cases A sample size of that magnitude may be too large for conventional PCR methodologies that typically use relatively small sample sizes, for example on the order of 1 microliter to about 100 microliters, such as, for example, those relying on multi-well titer plate formats. That is, for a 25 gram sample, to perform PCR, the sample may be stomacked and mixed with appropriate PCR reagents, probes, primers, etc., ultimately yielding a liquid sample volume on the order of about 250 milliliters, much larger than can be accommodated using conventional PCR detection platforms.

Further, if only a portion of the sample were subjected to PCR, in circumstances where only a single to a few pathogens are present in, for example, a 25 gram sample, it is statistically unlikely that the reduced sample volume extracted from the initial sample size will contain the pathogen(s) of interest.

As will be explained, various exemplary embodiments of the present teachings can accommodate a relatively large initial sample size and relatively rapidly isolate and collect target nucleic acids, such as, for example, pathogen nucleic acids, from the sample in a reduced amount that is amenable to conventional PCR detection methodologies. By way of example only, the isolated nucleic acids sample size may be reduced, thereby concentrating the nucleic acids, relative to the initial sample size by an order of about $10^4$.

In various applications, isolation and subsequent detection of target nucleic acids also may be complicated by a sample that contains various cell types or other matter containing nucleic acids such that nucleic acids of one type may contaminate (e.g., be mixed with) collected nucleic acids of another type. In other words, isolating and detecting target nucleic acids in a sample that has a mixture of material (e.g., cells, viral particles, and/or other entities containing nucleic acid) containing target and nontarget nucleic acids can pose challenges. In forensics, one example includes separating nucleic acids (e.g., DNA) from a mix of sperm cells (S-cells) and epithelial cells (E-cells), wherein the separated nucleic acids from the S-cells are not substantially contaminated with the nucleic acids from the E-cells and vice versa. In pathogen detection, an example includes separating and collecting target nucleic acids (e.g., nucleic acids from bacteria cells such as, for example, *E. coli*) from nontarget nucleic acids (e.g., host cells, such as, for example, cow cells in the case of hamburger meat). In the latter example, the amount of host cells may far exceed the amount of bacteria, and performing PCR detection may be complicated by host nucleic acids being present with the pathogen (e.g., bacteria in this example) nucleic acids.

In accordance with the present teachings, various exemplary embodiments use electrophoretic forces, including using two or more rounds of electrophoresis, to permit relatively rapid isolation and collection of target nucleic acids from a sample that may contain entities containing the target nucleic acids as well as other material, including, for example, one or more of entities containing nontarget nucleic acids, impurities, including, for example, cell debris, and/or proteins. In accordance with various exemplary embodiments of the present teachings may remove nucleic acids from dead pathogens and/or other dead cells, thereby isolating live nucleic acids (including, for example, pathogen nucleic acids) for subsequent analysis (e.g., detection).

In accordance with various exemplary embodiments, the present teachings provide techniques that may rely on multiple disruption and electrophoresis steps to relatively rapidly permit isolation of differing nucleic acids (e.g., target and nontarget) from differing types of entities containing nucleic acids. Various exemplary embodiments also permit a relatively large sample size to be reduced to a relatively small purified nucleic acid sample size amenable for conventional PCR detection techniques by relatively rapidly isolating and collecting target nucleic acids from an initial sample amount, with the isolated and collected target nucleic acids forming a small, concentrated size sample ultimately subjected to PCR detection.

In comparison to some conventional techniques for detecting the presence and/or type of nucleic acids, various exemplary embodiments may be performed in a fraction of the time. For example, in the case of pathogen detection in food products, various exemplary embodiments may take from about 10 minutes to about 90 minutes to isolate the pathogen nucleic acids, and about 40 minutes to about 120 minutes to perform PCR detection of pathogen nucleic acids in an initial food sample having a volume of about 25 milliliters to about 1000 milliliters. This relatively short time period may be attributed to the relatively rapid time in which disruption and electrophoresis to isolate target nucleic acids can be performed, and the relatively fast nature of PCR detection when used on an appropriate sample (e.g., containing concentrated (e.g., purified) nucleic acids). Using conventional growth, culture, and detection techniques described above, such pathogen detection and/or identification can take several hours, for example, from about 4 hours to about 12 hours for a similar sample size. Moreover, various exemplary embodiments may permit parallel processing of a collected sample, as will be explained further below, rather than sequential analyzing of one or a limited number of collected sample vials.

Various exemplary embodiments also may be suitable for automated raw and prepared sample handling, thereby minimizing contamination and increasing processing efficiency. Various exemplary embodiments may automate the process of isolating pathogen nucleic acids so that operators are not exposed to dangerous concentrations of pathogens. Further, various exemplary embodiments may provide platforms for sample preparation that are compatible with conventional PCR and other biological assay platforms, such as, for example, standard titer plate configurations.

Figure 1B:
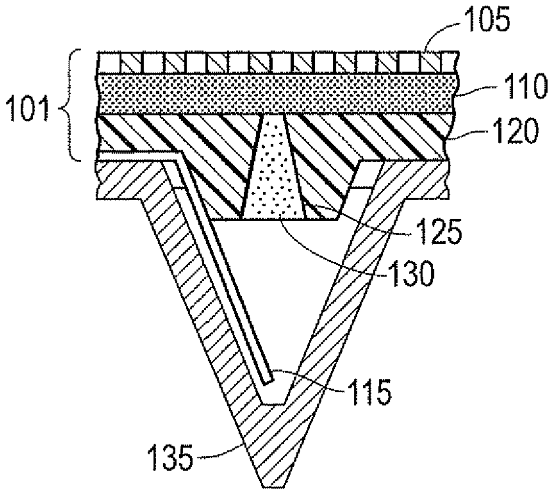
FIG. 1B is a partial cross-sectional view of the system of FIG. 1A showing a single sample chamber.

An exemplary embodiment of a system that relies on electrophoretic forces for isolating and collecting nucleic acids from a sample is depicted in FIGS. 1A and 1B. The system of FIGS. 1A and 1B facilitates automated preparation of a sample by extracting, isolating, and collecting nucleic acids from a sample prior to performing further analysis of the nucleic acids, such as, for example, PCR and/or other desired assays. The configuration of the exemplary embodiments of FIGS. 1A and 1B also allows for the collection of nucleic acids of interest into a standard format of wells of a titer plate, which can reduce the overall sample preparation time by obviating the need to manually pipette or otherwise manually transfer isolated nucleic acids to a titer plate.

With reference to FIG. 1A, an isometric view of an electrophoresis-based sample preparation system 100 is shown. The system 100 includes a sample holder 132, which in the exemplary embodiment shown is a titer plate. Such a titer plate can have a plurality of sample chambers 135 (e.g., wells) formed therein in any of a variety of formats with which those skilled in the art have familiarity, including, but not limited to, for example, an array of 96, 384, 1536, etc. wells. In various exemplary embodiments, each sample chamber 135 may have a volume ranging from about 5 microliters to about 500 microliters.

The system 100 also includes an electrophoresis matrix plate 101 that includes a substantially planar electrode 105, filter 110, and a support plate 120 supporting the electrode 105 and the filter 110. Another filter (not shown in FIG. 1A) may be provided on the side of the support plate 120 opposite to the side supporting the filter 110. In various exemplary embodiments, the filter 110 may be a gel, such as for example, an agarose gel, that is used to adhere the plate 120 to the electrode 105. Alternatively, the components of the electrophoresis matrix plate 101 may be secured together via any suitable adhesive or securing mechanism with which those ordinarily skilled in the art would be familiar.

The system 100 also may include a power supply 160 configured to be placed in electrical connection with the electrode 105 to supply power thereto. In various exemplary embodiments, the electrode 105 may be perforated (e.g., have a mesh configuration) that may allow gas from the sample chambers 135 to escape therethrough when the electrophoresis matrix plate 101 is in mating engagement with the sample holder 132 for nucleic acid collection.

In various exemplary embodiments, the system 100 also may optionally include a heater and/or shaker plate 150, the purpose of which will be described in more detail below with reference to an exemplary operation of the system 100.

With reference now to FIG. 1B, a partial cross-sectional view of the system 100 is shown with a single well 135 of the sample holder 132 depicted. As shown, the support plate 120 may define a plurality of collection chambers 125 containing the second filter 130. The plurality of chambers 125 may be arranged such that when the electrophoresis matrix plate 101 is aligned with the sample holder 132, each chamber 125 aligns with a respective chamber 135.

Each chamber 135 also is configured to be associated with an electrode 115. As depicted in the exemplary embodiment of FIG. 1B, the electrodes 115 may be connected to the matrix plate 101 and extend from the support 120 proximate each chamber 125 such that when the plate 101 is positioned over the sample holder 132, each electrode 115 extends into the chamber 135 with the free end of the electrode 115 near the bottom of each chamber 135. The electrodes 115 also may be configured to be placed in electrical connection with the power source 160. The electrodes 105 and 115 may be oppositely charged when powered by the power source 160. For example, in various operations described in further detail below, the electrode 105 may be positively charged and the electrode 115 may be negatively charged. The electrodes 105 and 115 may be made of any electrically conductive material, including, but not limited to, for example, platinum, copper, silver, aluminum, electrically conductive plastics, or other electrically conductive material.

As illustrated in FIG. 1B, the electrode 115 may be configured to facilitate insertion of the electrode 115 into the sample chamber 135. The length of the electrode 115 may be selected so that the electrode 115 extends substantially the entire depth of the chamber 135, for example, such that a free end of the electrode 115 is located proximate a bottom of the chamber 135. In various exemplary embodiments, the electrode 115 may be a wire to facilitate positioning within the chamber 135. To enable an electric field between the electrode 105 and the electrode 115 to penetrate substantially all of the sample contained in sample chamber 135, the electrode 115 may be electrically isolated, for example with insulative cladding, for example, made from plastic, rubber, and/or any suitable electrically insulating material, along substantially its entire length up to the free end.

In accordance with various exemplary embodiments, the filters 110 and 130 may be configured as size exclusion filters, permitting the passage of selected materials while preventing (e.g., through size exclusion) the passage of other materials. In other words, the filters may permit the passage of gases, liquids, and solid materials of a preselected size. Suitable materials for the filters of various exemplary embodiments described herein may include, but are not limited to, for example, beads, fibers, gels, metals formed with holes (e.g., via laser), and/or any porous material configured to pass particles of less than or equal to a preselected size (e.g., DNA) and block particles larger than the preselected size. As mentioned above, in various exemplary embodiments, the filters described may be made of an agarose gel that allows the pore size of the filter to be controlled by altering the concentration of agarose used to form the gel. Those having ordinary skill in the art would be familiar with the formation of such gels. Each filter also may be made of a differing material and/or differing concentrations of material, which may permit passage or exclusion materials of differing sizes, for example by controlling the pore size of each filter. Another gel material that may be suitable for use with exemplary embodiments in accordance with the present teachings includes, but is not limited to, polyacrylamide.

The filters 110 and 130 also may be saturated with an electrically conductive medium, such as, for example, a TBE (tris/borate/EDTA (ethylene diamine tetra-acetic acid)) buffer or other salt-based buffer, or may be made of an electrically conductive material. In the case of a gel filter, the substance used to form the gel (e.g., agarose powder) may be mixed with the electrically conductive medium (e.g., electrically conductive buffer) and allowed to solidify to form the gel. As will be explained in more detail below, providing the filters 110 and 130 with electrically conductive properties permits charged particles less than a predetermined size to pass through the filters during electrophoresis.

FIGS. 2A-2E depict exemplary steps for operating the system of FIGS. 1A and 1B to extract, isolate, and collect target nucleic acids from a sample. Although FIGS. 2A-2E illustrate a single sample chamber 135, it will be understood that the operation which will be described applies to each of the sample chambers 135 of the sample holder 132 and the sample processing may occur in parallel in each chamber 135.

Figures 2A, 2B, 2C, 2D, 2E:
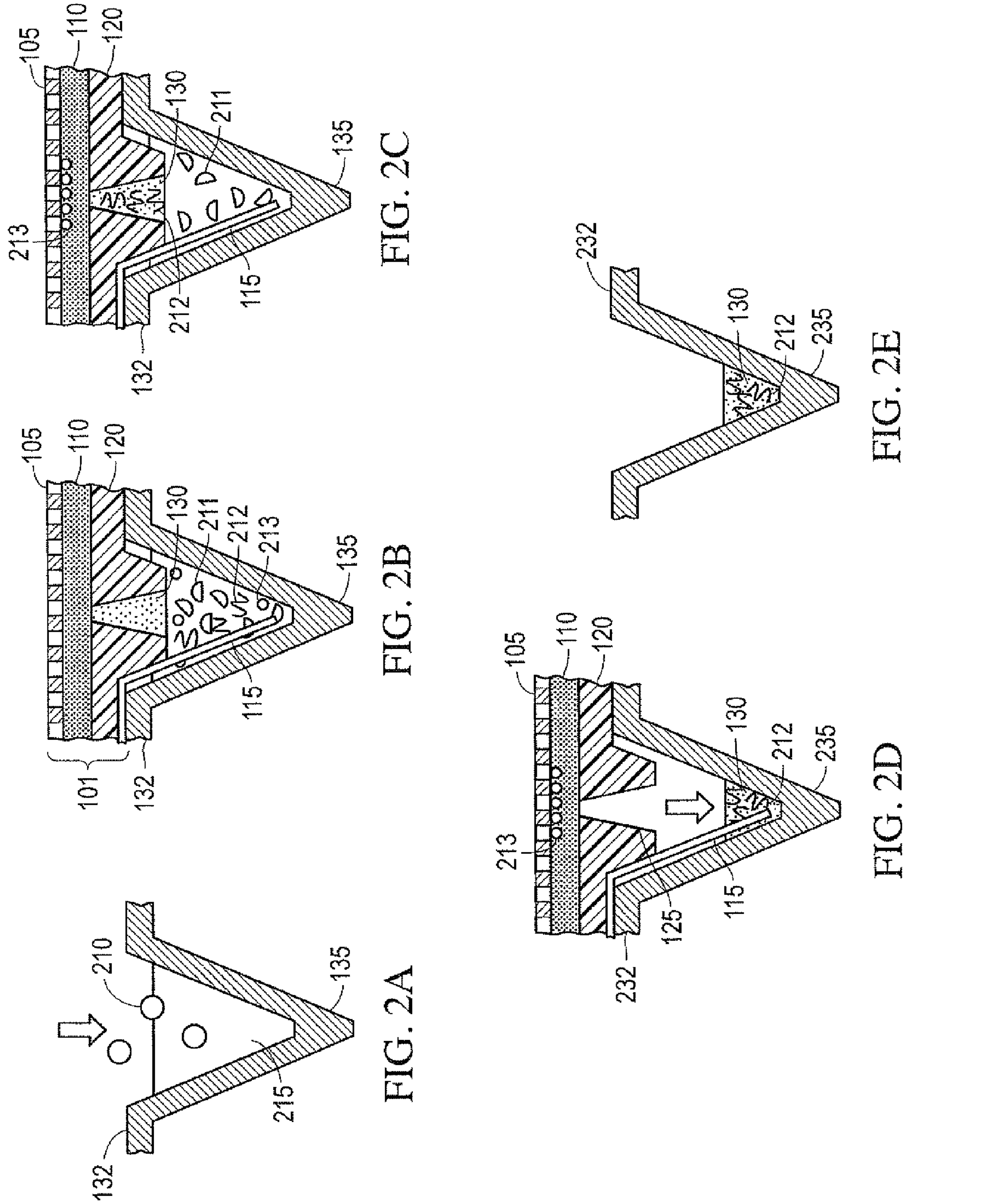
FIGS. 2A-2E show an exemplary embodiment of operating the system of FIGS. 1A and 1B in accordance with the present teachings.

In FIG. 2A, a sample containing entities, such as, for example, cells 210, from which it is desired to extract and collect target nucleic acids is introduced into the sample chamber 135. In addition to the sample, a lysing reagent 215 may be placed in the sample chamber 135. The lysing reagent 215 may be predeposited in the sample chamber 135 or may be introduced after or at the same time as the raw sample 210. The lysing reagent 215 may be selected so as to achieve disruption of the cells in the raw sample from which it is desired to extract the target nucleic acids. The lysing reagent 215 may be selected from any of a variety of lysing reagents based on the type of cell for which lysis is desired. Those having ordinary skill in the art are familiar with the selection of suitable lysing reagents. To perform electrophoresis, the lysing reagent 215 may be electrically conductive or the lysing reagent can be added to an electrically conductive medium, such as, for example, an electrolyte, in the chamber 135. Suitable lysing reagents that may be used with various exemplary embodiments of the present teachings include, but are not limited to, detergents.

The lysing reagent 215 and sample with cells 210 may be permitted to mix for a sufficient time to lyse the cells 210 (e.g., rupture the cell membranes). In various exemplary embodiments, either in lieu of or in addition to the chemical lysing achieved by the lysing reagent, mechanical (e.g., agitating with beads, shearing with a pipette or other shearing mechanism, vibrating, sonicating), electrical, and/or thermal disruption mechanisms may be employed to rupture the membranes of the cells 210. By way of example, a heater and/or shaker plate 150 (shown in FIG. 1A) may be used to agitate and/or heat the contents of the sample chamber 135 to assist in or achieve disruption. Those having ordinary skill in the art would be familiar with various mechanisms for achieving disruption of the cells 210 and the exemplary embodiment of FIG. 2A is not intended to limit the scope of present teachings. Thus, it is envisioned as within the scope of the present teachings for any of a variety of disruption techniques that would be known to those ordinarily skilled in the art, or a combination of such techniques, may be used to disrupt the cells 210 to release nucleic acids therefrom. Further, those having ordinary skill in the art would understand the disruption of the cells 210 in the sample may occur prior to being placed into the sample chambers 135.

Once disruption of the cells 210 has occurred, the sample chamber 135 may contain various materials, including, for example, cell debris 211, target nucleic acids 212, impurities (e.g., other than cell debris and which may include small negatively charged particles as is discussed further below), proteins, and/or ribonucleic acids. The electrophoresis matrix plate 101 may also be placed in alignment with the sample holder 132 such that each collection chamber 125 substantially aligns with and each electrode 115 is received by a respective sample chamber 135, the alignment of one such collection chamber 125 with and receipt of one such electrode 115 by one sample chamber 135 being shown in FIG. 2B. The electrophoresis matrix plate 101 may be positioned relative to the sample holder 132 by either manual or automated placement. As mentioned previously, the filters 110 and 130 may be electrically conductive by virtue of either the material from which they are formed or being saturated with an electrically conductive medium.

When the electrophoresis matrix plate 101 is appropriately positioned relative to the sample holder 132, as illustrated for example in FIG. 2B, power may be provided to the electrodes 105 and 115 via the power source 160 (shown in FIG. 1), causing the electrode 105 to take on a positive charge and the electrode 115 to take on a negative charge. Activated as such, an electric field may be established between the electrodes 105 and 115, and may penetrate through the substance in the sample chamber 135 and the filters 130 and 110 (e.g., substantially across a height of the filters 130 and 110, e.g., in the vertical direction of in FIGS. 1 and 2). The electric field may be sufficient to cause negatively charged particles, including, for example, the target nucleic acids 212, contained in the sample chamber 135 to migrate via electrophoresis from the sample chamber 135 toward the positively charged electrode 105. Positively charged particles and/or uncharged particles will remain within the sample chamber 135, the former being attracted to the negatively charged electrode 115.

As the negatively charged particles, including target nucleic acids 212, for example, migrate toward the electrode 105, they will follow a path toward the filter 130 in the collection chamber 125 due to the porous nature and electrically conductive properties of that filter 130. The filter 130 may be configured so as to permit the target nucleic acids 212 to pass into the filter 130 while not permitting (blocking) passage of negatively charged particles larger than the nucleic acids 212, for example cell debris 211.

Once sufficient time has elapsed and the target nucleic acids 212 have migrated via electrophoresis into the filter 130, power to the electrodes 105 and 115 may be stopped leaving the captured target nucleic acids 212 trapped within the filter 130. As will be described in more detail below with reference to FIGS. 2D and 2E, at this point, the filter 130 with the captured target nucleic acids 212 may be removed from the collection chamber 125.

In some cases, after disruption, the sample may contain negatively-charged particles 213, such as, for example, impurities, smaller in size than the target nucleic acids 212. Such smaller, negatively-charged particles 213 therefore also may migrate via electrophoresis toward electrode 105 and into the filter 130. In such a case, the filter 110 may be configured (e.g., have pore sizes) so as to permit the passage of the smaller, negatively-charged particles 213 while not permitting passage of the target nucleic acids 212. In the case of the disrupted sample containing smaller, negatively charged particles 213 in addition to target nucleic acids 212, power to the electrodes 105 and 115 may be provided for a time sufficient to permit the smaller, negatively-charged particles 213 to pass via electrophoresis into the filter 110. Once the particles 213 have been trapped in the filter 110, the electrodes 105 and 115 may be deactivated, leaving target nucleic acids 212 captured in the filter 130 and smaller, negatively-charged particles 213 captured in the filter 110, as illustrated in FIG. 2C.

FIG. 2D depicts an exemplary step for collecting the isolated nucleic acids 212. In FIG. 2D, the electrophoresis matrix plate 101 may be removed from the sample holder 132 and positioned over another sample holder 232 having a similar configuration as the sample holder 132. For example, the sample holder 232 may be a titer plate having a plurality of sample chambers 235 that are arranged to align with the collection chambers 125 in the electrophoresis matrix plate 101. As with the views of FIGS. 2A-2C, FIGS. 2D and 2E illustrate only a single sample chamber 235, but it will be understood that the sample holder 232 may include a plurality of such chambers 235.

To remove the target nucleic acids 212, the electrophoresis matrix plate 101 and the sample holder 232 may be centrifuged together so as to force the filter 130 and the target nucleic acids 212 captured therein out of the collection chambers 125 and into the sample chambers 235 of the sample holder 232. During this removal step, any suitable mechanism, such as, for example, one or more clamps, may be used to secure the electrophoresis matrix plate 101 and sample holder 232 together. The force associated with centrifuging may be selected so that the denser filter 110 remains in the electrophoresis matrix plate 101, The configuration of the collection chamber 125 also may be selected to hinder the filter 110 from entering the collection chamber 125 during centrifugation. For example, as depicted in FIGS. 2A-2E, an opening of the chamber 125 closest to the filter 110 may be smaller than the opening that is further from the filter 110, for example, the chamber 125 may have a substantially frustro-conical configuration with the smaller opening closer to the filter 110. Such a configuration for the chamber 125 is exemplary only, however, and the chamber 125 may have a variety of other configurations that permit removal of the filter 130 via centrifugation without permitting the filter 110 to pass through the chamber 125.

Techniques other than centrifugation also may be used to release the filter 130 with captured nucleic acids from the collection chamber 125. Such techniques may include, but are not limited to, for example, vibrating the electrophoresis matrix plate 101, utilizing pressure, such as air or water pressure, to force the filter 130 out of the collection chamber 125, and/or otherwise exerting a force on the plate 101 sufficient to release the filter 130 from the collection chamber 125.

As shown in FIG. 2E, removal of the filter 130 and target nucleic acids 212 leaves substantially concentrated isolated target nucleic acids in the chambers 235 of the sample holder 232. Isolation and collection of the target nucleic acids 212 as illustrated in FIG. 2E enables further analysis and/or processing, such as for example PCR detection, of the target nucleic acids 212 as desired. In various exemplary embodiments, the volume of the target nucleic acids 212 collected in each sample chamber 235 of the sample holder 232 may range from about 1 microliters to about 500 microliters.

In various exemplary embodiments in accordance with the present teachings, in the case of a gel filter, once the filter capturing the target nucleic acids has been collected and removed from the electrophoresis system, if it is desired to perform PCR on the collected nucleic acids, a suitable PCR mixture (e.g., primers, probes, and reagents) may be added directly to the gel. The gel may be heated to liquefy the gel and PCR may be performed on the isolated, collected nucleic acids. As an alternative to perform further processing and/or analysis of captured target nucleic acids, the captured nucleic acids may be washed (e.g., eluted) from the filter and appropriate processing steps taken to perform the desired processing and/or analysis.

Figure 3A:
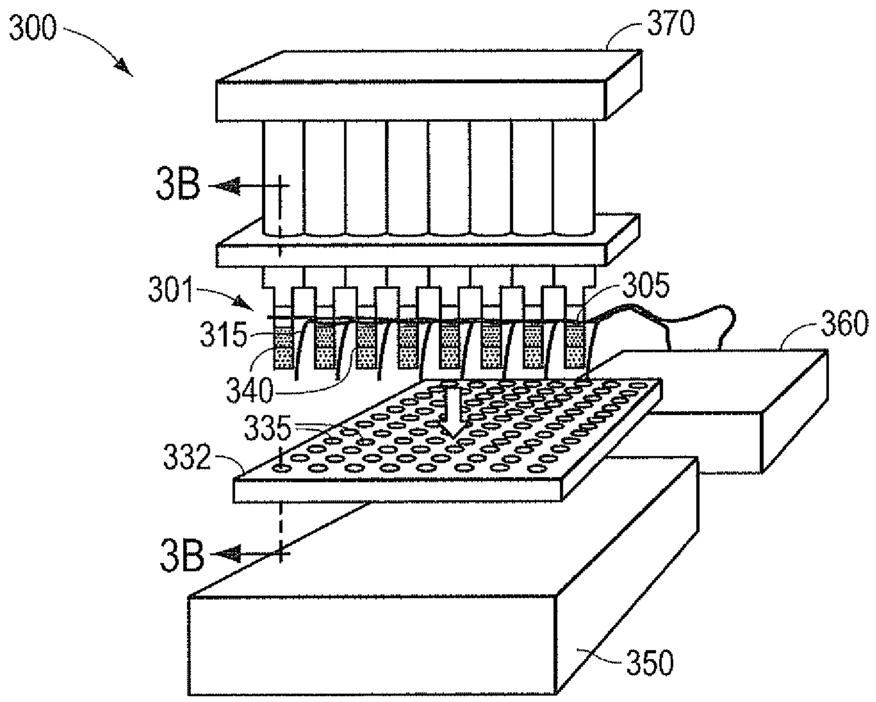
FIG. 3A is an isometric view of another exemplary embodiment of an electrophoresis-based sample preparation system in accordance with the present teachings.
Figure 3B:
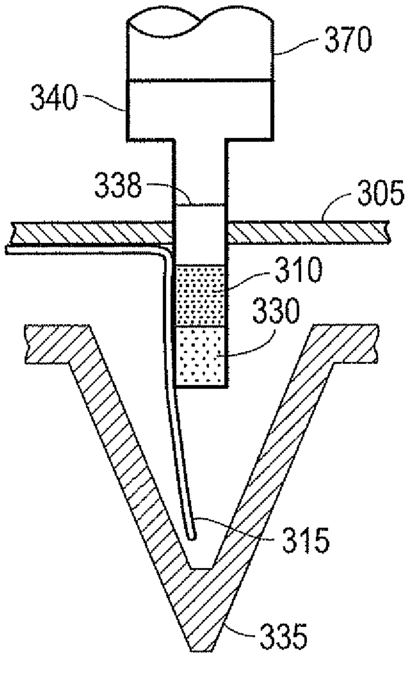
FIG. 3B is a partial cross-sectional view of the system of FIG. 3A showing a single sample chamber.

FIGS. 3A and 3B illustrate another exemplary embodiment of a system that relies on electrophoresis for isolating and collecting nucleic acids from a sample, with an isometric perspective view of the system being illustrated in FIG. 3A and a partial cross-sectional view of the system showing a single sample chamber 335 illustrated in FIG. 3B. In the exemplary embodiment of FIGS. 3A and 3B, the electrophoresis matrix plate 101 of FIGS. 1A and 1B is replaced by an electrophoresis matrix 301 comprising a plurality of electrophoresis matrix tips 340 that house the first and second filters and define therein collection chambers. The sample holder 332, optional heater/shaker plate 350, power supply 360, and electrodes 315 may have substantially the same configuration as described above with respect to those components of the exemplary embodiment of FIGS. 1A and 1B.

According to an exemplary embodiment, the matrix tips 340 may be configured as plate dispenser tips similar to a syringe pump type mechanism. The matrix tips may be formed from any suitable material known to those of skill in the art, for example plastic, such as polypropylene.

The electrophoresis matrix tips 340 may be arranged in an array that substantially coincides with the sample chambers 335 of the sample holder 332, which in various exemplary embodiments may be a titer plate with a plurality of wells. Each tip 340 may have a substantially hollow cylindrical configuration and contain therein a filter 310 and a filter 330 of differing configurations such that the filter 310 permits the passage of material of a selected size and the filter 330 permits the passage of material of a different selected size, as will be set forth below in the description of FIGS. 4A-4E. Each tip 340 also may contain an electrolyte 338 or other electrically conductive medium above the filter 310.

In an exemplary embodiment, the filters 310 and 330 may be formed of a porous gel material (e.g., agarose gel). To position each filter 310 and 330 in the matrix tips 340, the tips 340 may first be filled with a liquid that forms the gel filter 310 upon solidification. After the filter 310 has solidified, the tip 340 may be filled with a liquid that forms the gel filter 330 upon solidification. Thus, each filter 310 and 330 may fill the matrix tip 340 as a liquid and be permitted to solidify to form the gels. Those having ordinary skill in the art would understand a variety of ways to provide the matrix tips 340 with filters 310 and 330, whether those filters are gel filters or other suitable filter material in accordance with the present teachings.

A pair of electrodes 305 and 315 may be associated with each electrophoresis matrix tip 340. In an exemplary configuration, each tip may be associated with a respective first electrode 315 having a configuration similar to the electrode 115 of FIGS. 1 and 2 and configured to be inserted in a corresponding sample chamber 335 of the sample holder 332. A second electrode 305 may be common to the array of tips 340 and may be disposed near a top of the tips 340 in the proximity of the electrolyte 338. By way of example only, the second electrode 305 may have a wire-like configuration and may pass through the array of tips 340, for example through small holes formed in each tip 340. Both electrodes 305 and 315 may be configured to be placed in electrical connection with the power source 360 and upon activation, the electrode 305 may be positively charged and the electrode 315 may be negatively charged. With the electrode 315 positioned with its free end proximate or at the bottom of the sample chamber 335, the electric field generated between the electrode 305 and the electrode 315 may penetrate substantially all of the contents contained in the sample chamber 335, as well as through the thickness of the filters 310 and 330 which may be saturated with electrically conductive medium (e.g., an electrically conductive buffer) or otherwise may be configured to be electrically conductive.

In the exemplary embodiment of FIGS. 3A and 3B, the system also may include a liquid handling head 370 which may be automated (e.g., robotic), for example, including a syringe pump and/or a mechanism to transfer the tips 340 into cooperation with the sample holder 332.

Figure 4A:
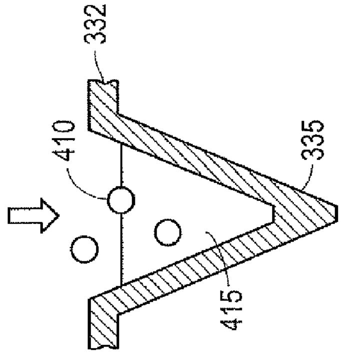
FIGS. 4A-4E show an exemplary embodiment of operating the system of FIGS. 3A and 3B in accordance with the present teachings.

Referring now to FIGS. 4A-4E, an exemplary operation of the system of FIGS. 3A and 3B is depicted. In FIG. 4A, a sample containing entities containing nucleic acids, such as, for example, cells 410 and a lysing reagent 415 may be introduced into each of the sample chambers 335 of the sample holder 332. In various exemplary embodiments, the lysing reagent 415 may be predeposited in the chambers 335 or may be added at the same time or after the raw sample 410. In various exemplary embodiments, the lysing reagent may be electrically conductive. Alternatively, an electrically conductive medium separate from the lysing reagent also may be added to the sample chambers 335. Optionally, the heater/shaker plate 350 may be activated to heat and/or agitate the sample holder 332 and assist in lysing cells containing target nucleic acids in the sample 410. Those ordinarily skilled in the art would understand that any disruption technique may be used in lieu of or in addition to lysing, as discussed above with reference to FIGS. 2A-2E, with lysing being one exemplary embodiment. Further, as described above with reference to FIGS. 2A-2E, instead of the disruption of cells 410 occurring while the sample is in the chamber 335, the disruption step may occur prior to introducing sample to the sample chamber 335.

Figure 4B:
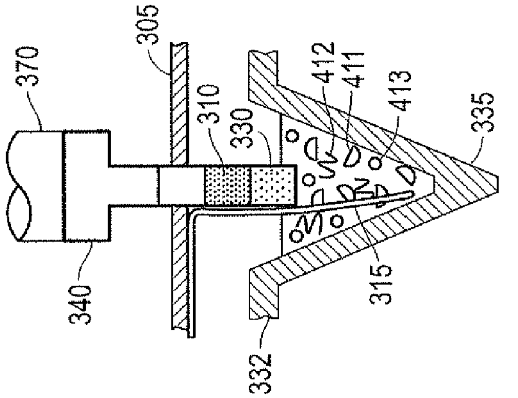

After sufficient time has elapsed for disruption of the cells 410 to occur and release target nucleic acids 412, the array of tips 340 may be inserted into each of the corresponding array of sample chambers 335. Positioning of the tips 340 relative to the sample chambers 335 may occur manually or via an automated mechanism such as, for example, a robotic transfer mechanism moving either the electrophoresis matrix 301 or the sample holder 332 into position. Once the tips 340 are positioned appropriately relative to the respective sample chambers 335, with the electrodes 315 being inserted in each chamber 335, as illustrated in FIG. 4B, the electrodes 305 and 315 may be supplied power from the power source 360 thereby generating an electric field therebetween. With electrode 305 being positively charged and electrode 315 being negatively charged, negatively charged particles in the sample chamber 335, including, for example, target nucleic acids 412, may migrate away from electrode 315 and toward electrode 305. Because the filters 310 and 330 are electrically conductive, whether by being saturated with an electrically conductive medium or otherwise, the electric field between the electrodes 305 and 315 will extend through the thickness of the filters 310 and 330, causing negatively charged material from the disrupted sample to attempt passage through those filters 310 and 330. In a manner similar to filters 130 and 110, respectively, the filter 330 may be configured to permit passage of target nucleic acids 412 while excluding on the basis of size larger negatively charged particles. If the disrupted sample also contains negatively-charged, smaller particles 413, such as impurities for example, the filter 310 may be used and configured to block passage of the larger target nucleic acids 412 and permit passage of smaller, negatively charged particles 413. Those having skill in the art would understand, however, that the filter 310 may not be needed, for example, if there are no negatively charged particles smaller than the target nucleic acids 412 for which separation and capture are desired.

Figure 4C:
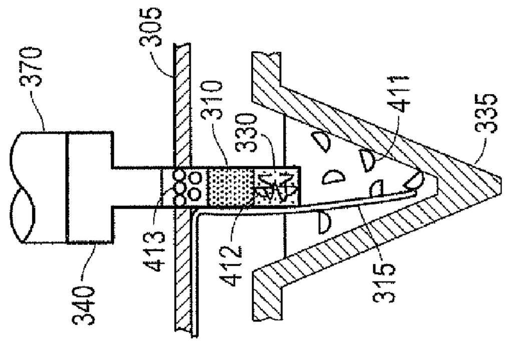
Figure 4D:
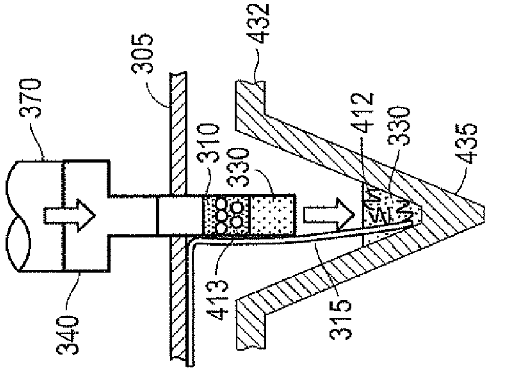
Figure 4E:
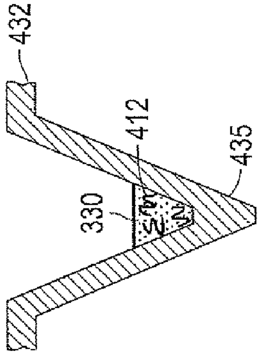

After sufficient time has elapsed, the target nucleic acids 412 will have migrated via electrophoresis into the filter 330 and be captured therein and the smaller, negatively-charged particles 413 will have migrated into the filter 310, as shown in FIG. 4C. Electrophoresis may continue until the smaller, negatively-charged particles 413 pass through the filter 310 and into the electrically conductive medium (e.g., electrolyte) 338. Once the target nucleic acids 412 have been captured and any smaller, negatively-charged particles 413 have been separated from the target nucleic acids 412, power to the electrodes 305 and 315 may be removed and the tips 340 may be moved from the raw sample holder 332 to another sample holder 432, aligning each tip 340 with a corresponding sample chamber 435 (e.g., well in a titer plate), as depicted in FIG. 4D. To release the target nucleic acids 412 captured and collected in the tips 340, a positive pressure may be applied above the electrolyte 338 in the tips 340 to force the filter 330 and the target nucleic acids 412 therein out of the tips 340 and into the sample chamber 435. The positive pressure may be removed prior to release of the filter 310 out of the tips 340. In various exemplary embodiments, as mentioned above, the tips 340 may be syringe-like barrels and a syringe pump 370 (the entire syringe pump being shown in FIG. 3A) may be used to exert the positive pressure used to extract the filter 330 from the tips 340.

After removal of the filter 330 and the target nucleic acids 412 to the sample holder 432, the electrophoresis matrix tips 340 may be removed and the isolated and collected sample in the sample holder 432 subjected to further processing and/or analysis as desired, for example, in a manner similar to that described above with reference to the exemplary embodiments of FIGS. 1 and 2.

Figure 5A:
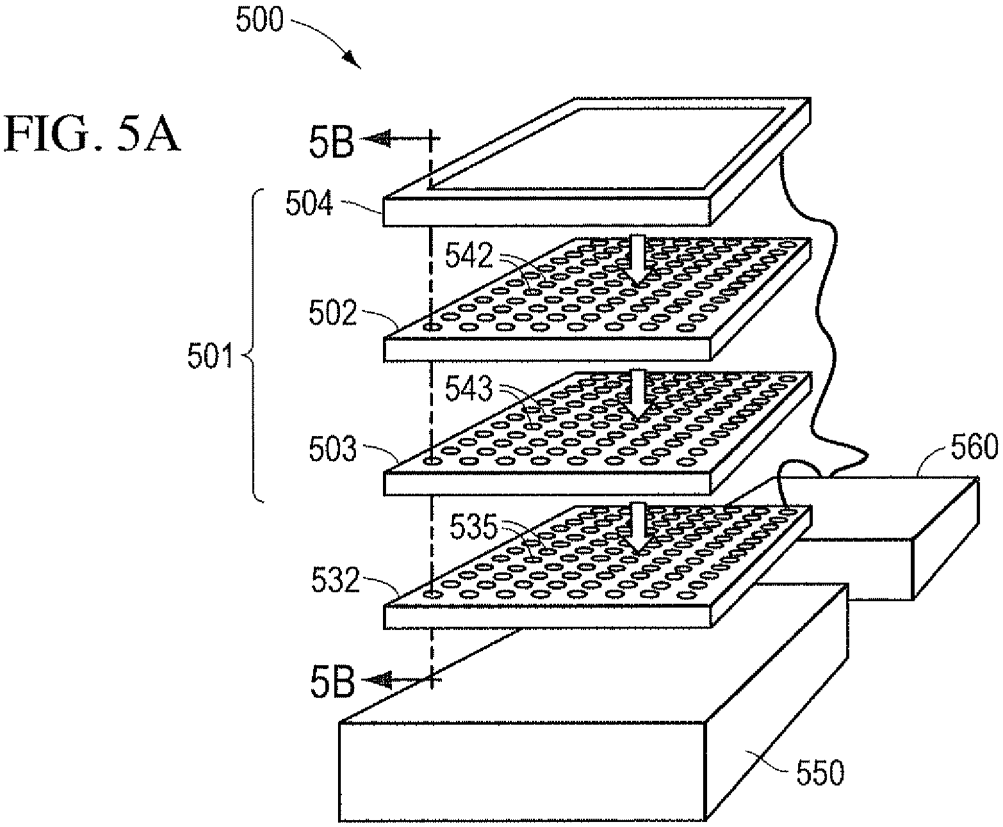
FIG. 5A is an isometric view of yet another exemplary embodiment of an electrophoresis-based sample preparation system in accordance with the present teachings.
Figure 5B:
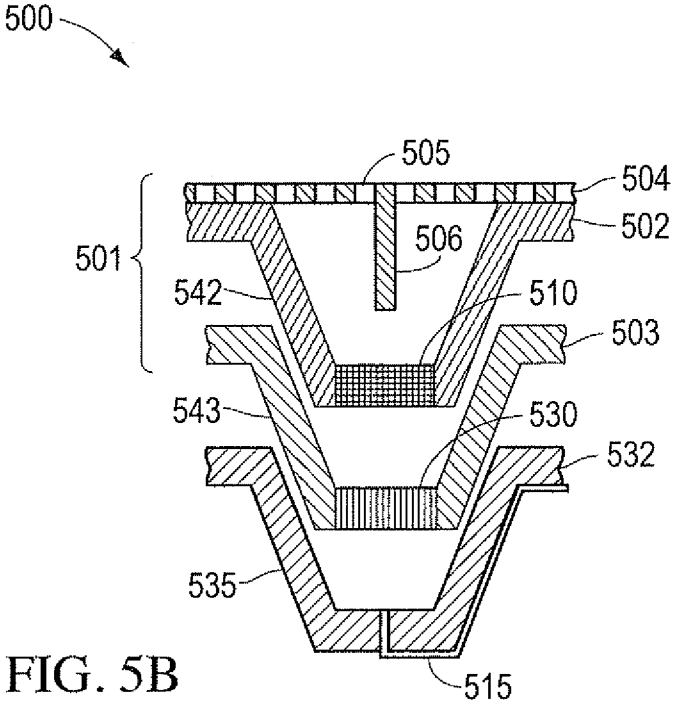
FIG. 5B is a partial cross-sectional view of the system of FIG. 5A showing a single sample chamber.

Another exemplary embodiment of an electrophoresis-based system used to extract, isolate, and collect target nucleic acids is depicted in FIGS. 5A and 5B. In the exemplary embodiment of FIGS. 5A and 5B, a plurality of titer plates are used to form an electrophoresis matrix 501 for isolating and collecting target nucleic acids from a raw sample. More specifically, the electrophoresis-based sample preparation system 500 of the exemplary embodiment of FIGS. 5A and 5B includes an electrode plate 504, a first separation plate 502, a second separation plate 503, and a sample holder 532. The separation plates 502 and 503 may each have a configuration similar to the sample holder 532, for example, they may be titer plates having a plurality of collection chambers 542 and 543, respectively, arranged in a format similar to sample chambers 535 of the titer plate 532. In this way, as shown in FIG. 5B, the plates 502, 503, and 532 may align with each other and the respective chambers 542, 543, and 535 of each may cooperate in a nesting manner. As shown in FIG. 5B, the chambers 542 may nest inside chambers 543 and the chambers 543 may nest inside the chambers 535, with the bottom portions of the chambers 542 and 543 and of the chambers 543 and 535, respectively, being spaced apart. In the exemplary embodiment of FIGS. 5A and 5B, the chambers 542, 543, and 535 are configured as wells, however, those having skill in the art would recognize numerous other configurations, including, for example, tubes, that the chambers may have.

As best shown in FIG. 5B, each of the chambers 542 and 543 may have a bottom portion that is configured to permit passage of various substances. In particular, the bottom portion of the chambers 542 may include a filter 510 and the bottom portion of the chambers 543 may include a filter 530. The filters 510 and 530 may be size exclusion filters and may operate similarly to the size exclusion filters 110 and 130, and 310 and 330, respectively, described above. That is, the filter 510 may be configured to block the passage of particles of larger size than the filter 530. In various exemplary embodiments, the filters 510 and 530 may be made of porous gels by placing the bottom portions of each of the chambers 542 and 543 into a suitable liquid (e.g., an agarose solution) and permitting the liquid to solidify to a gel. In various exemplary embodiments, the filters 510 and 530 may be made of various other materials, such as, for example, beads, porous metals (e.g., formed with laser holes), fibers, and/or other porous materials, and the sample chambers 542 and 543 may include structure suitable to support such materials.

The electrode plate 504 may have a substantially planar electrode 505 which in the exemplary embodiment may be embedded in or deposited on a surface of the plate 504. In various exemplary embodiments, as depicted in FIG. 5B, the electrode 505 may be perforated (e.g., have a mesh-like configuration) to permit gas to escape, similar to that described above with reference to the exemplary embodiment of FIGS. 1A and 1B. Extending from contact with the planar electrode 505 may be a plurality of electrode posts 506, for example wire-like posts, arranged so as to correspond to the positioning of respective chambers 535, 542, and/or 543 when the electrode plate 540 is aligned with the plates 532, 502, and/or 503. A power supply 560 may be configured to be placed in electrical connection with the electrode plate 504 to supply power to electrode 505 and electrode posts 506. Upon the supply of power from the power supply 560, the electrode 505 and electrode posts 506 may become negatively charged.

Each of the sample chambers 535 also may be associated with an electrode. By way of example only, FIG. 5B depicts each sample chamber 535 having an electrode 515 embedded in a bottom of the chamber 535. The electrodes 515 may extend through a bottom of the chambers 535 so as to be in electrical contact with the contents of the sample chamber 535 and may run along an exterior surface of the sample chambers 535 and into electrical connection with the power supply 560. Upon supply of power to the electrodes 515 from the power supply 560, the electrodes 515 may become positively charged and create an electric field with the electrode posts 506.

Those having ordinary skill in the art would recognize that the configurations of the electrode layer 505, electrode posts 506, and electrodes 515 are exemplary only and nonlimiting. Various other configurations for the electrodes may be used to generate an appropriate electric field to achieve migration via electrophoresis of charged particles from the sample holder 532 to a collection area. For example, it should be understood that the wire electrode configuration shown and described with reference to the exemplary embodiments of FIGS. 1 and 3 may be used in lieu of the electrode 515 and vice versa in the exemplary embodiments of FIGS. 1 and 3.

Figure 6B:
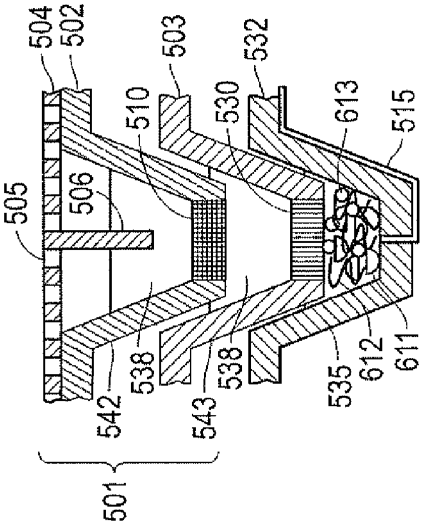
FIGS. 6A-6D show an exemplary embodiment of operating the system of FIGS. 5A and 5B in accordance with the present teachings.
Figure 6D:
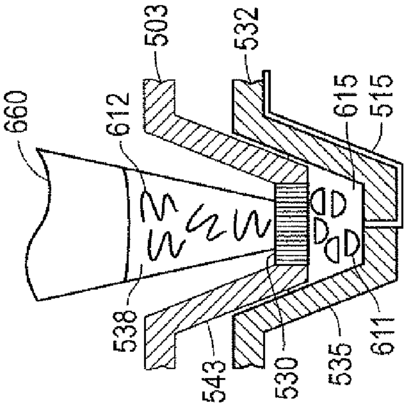
Figure 6A:
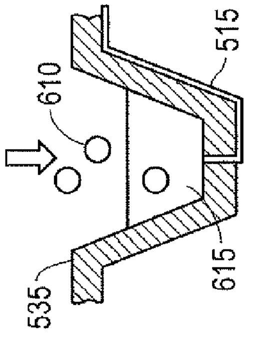

An exemplary operation of the electrophoresis-based system 500 will now be described with reference to FIGS. 6A-6D. As with exemplary embodiments described above, for ease of illustration, the cross-sectional views of FIGS. 6A-6D are partial, depicting a section of the system 500 through only a single sample chamber 535. In FIG. 6A, a sample containing entities containing nucleic acids, such as for example, cells 610, and a lysing reagent 615 may be introduced into each of the sample chambers 535 of the sample holder 532. In various exemplary embodiments, the lysing reagent 615 may be predeposited in the chambers 535 or may be added at the same time or after the raw sample. In various exemplary embodiments, the lysing reagent may be electrically conductive. Alternatively, an electrically conductive substance (e.g., electrolyte) separate from the lysing reagent also may be added to the sample chambers 535. Optionally, the heater/shaker plate 550 may be activated to heat and/or agitate the sample holder 532 and assist in disruption to release target nucleic acids in the sample 610 and/or another type of disruption technique may be used. As with exemplary embodiments described above, those having skill in the art would understand that disruption of cells 610 may be achieved via any of a variety of disruption techniques, with lysing being exemplary only. Further, disruption may occur to disrupt cells 610 prior to their introduction into the sample chambers 535.

After sufficient time has elapsed for disruption of the cells 610 to occur and release target nucleic acids 612, the electrophoresis matrix 501 may be aligned with the sample holder 532 such that the chambers 543 are inserted into sample chambers 535, the chambers 542 are inserted in the chambers 543, and the electrode posts 506 are inserted in the chambers 542. The collection chambers 542 and 543 may also be filled with an electrolyte or other electrically conductive medium 538. Such electrically conductive medium 538 may either be predeposited in the chambers 542 and 543 or may be added to the chambers 542 and 543 before matrix 501 is used.

In various exemplary embodiments, the positioning of the matrix 501 relative to the sample holder 532 may occur manually or via an automated mechanism such as, for example, a robotic transfer mechanism. Skilled artisans would understand various automated mechanisms that could be used to move the matrix 501 into position relative to the sample holder 532. Once the matrix 501 is positioned appropriately relative to the respective sample chambers 535, with the electrodes 506 being inserted in each chamber 542, as illustrated in FIG. 6B, power from the power source 560 may be supplied to the electrodes 505, 506, and 515 thereby generating an electric field between the electrodes 505, 506, and 515. With electrode 505 and electrode posts 506 being positively charged and electrode 515 being negatively charged, negatively charged particles in the sample chamber 535, including, for example, target nucleic acids 612, may migrate via electrophoresis away from electrode 515 and toward electrode post 506. Because the filters 510 and 530 are electrically conductive, whether by being saturated with an electrically conductive medium or otherwise having electrically conductive properties, the electric field between the electrode post 506 and the electrode 515 will extend through the thickness of the filters 510 and 530, causing negatively charged material in the sample chamber 535 to attempt passage through those filters 510 and 530. In a manner similar to filters 130 and 110, respectively, the filter 530 may be configured to permit passage of target nucleic acids 612 while excluding larger, negatively charged particles 611, such as, for example, cell debris and/or other particles on the basis of size. If the disrupted sample also contains negatively charged, smaller particles 613, such as impurities other than cell debris too large to pass through filter 530, for example, the filter 510 may be used and configured to block passage of the larger target nucleic acids 612 and permit passage of smaller, negatively-charged particles 613. Other particles (not shown) in the sample chambers 535 that are not charged or are positively charged also will remain in sample chamber 535.

Figure 6C:
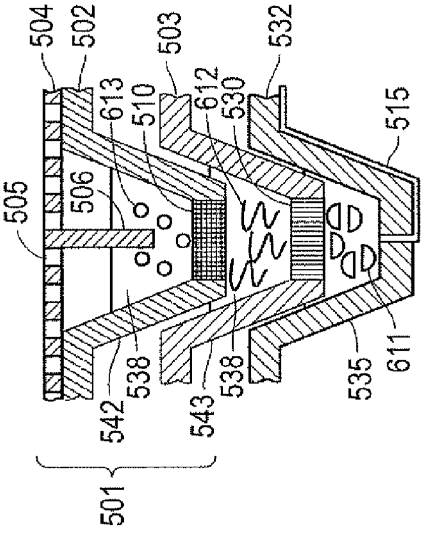

After sufficient time has elapsed, the target nucleic acids 612 will have migrated via electrophoresis into the filter 530 and the smaller, negatively-charged particles 613 will have migrated via electrophoresis into the filter 510. Electrophoresis may be allowed to continue until the target nucleic acids 612 pass through filter 530 and into the chamber 543 and the smaller, negatively-charged particles 613 pass through the filter 530 and 510 and into the chamber 542, as shown in FIG. 6C. Once the target nucleic acids 612 have been separated and collected in chamber 543 and any smaller, negatively-charged particles 613 have been separated from the target nucleic acids 612 and collected in chamber 542, power to the electrodes 505 and 515 may be removed and the electrode plate 504 and plate 502 may be removed from the plate 503, leaving the sample chambers 543 exposed. A manual or automated removal device 660, such as, for example, a needle, pipette, or other removal device, may be used to remove the captured target nucleic acids 612 and the electrically conductive medium 538 from the sample chambers 543, which may then be brought to another location and/or deposited into another sample holder (not shown) for further processing and/or analyzing, such as PCR for example, of the target nucleic acids 612, as desired.

Figure 7A:
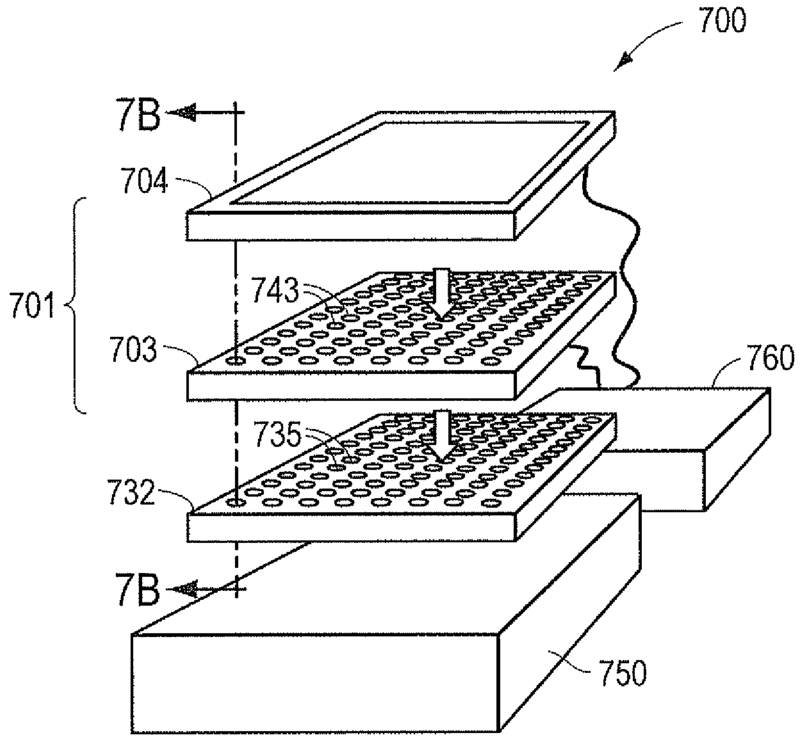
FIG. 7A is an isometric view of another exemplary embodiment of an electrophoresis-based sample preparation system in accordance with the present teachings.
Figure 7B:
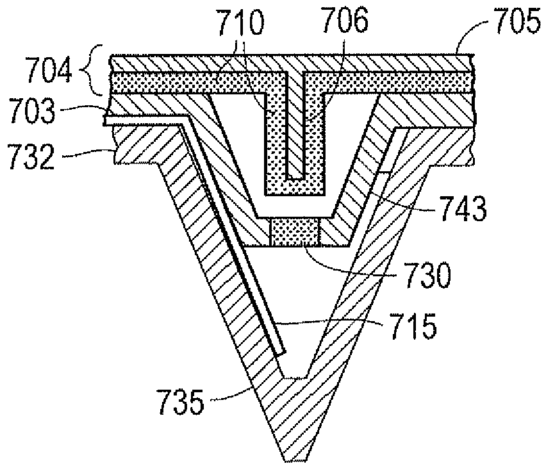
FIG. 7B is a partial cross-sectional view of the system of FIG. 7A showing a single sample chamber.

Yet another exemplary embodiment of an electorphoresis-based sample preparation system is illustrated in FIGS. 7A and 7B. As with the exemplary embodiment of FIGS. 5A and 5B, the exemplary embodiment of FIGS. 7A and 7B utilizes a plurality of nesting titer (e.g., well) plates for isolating and collecting target nucleic acids from a raw sample. More specifically, the electrophoresis-based sample preparation system 700 of the exemplary embodiment of FIGS. 7A and 7B includes an electrophoresis matrix 701 and a sample holder 732. The electrophoresis matrix plate includes a combination electrode filter plate 704 and a separation plate 703.

The separation plate 703 may have a configuration similar to the sample holder 732, for example, it may be a titer plate having a plurality of collection chambers 743 (e.g., wells) arranged in a format similar to chambers 735 of the titer plate 732. In this way, as shown in FIG. 7B, the plates 703 and 732 may align with each other and the respective chambers 743 and 735 of each may cooperate in a nesting manner. As shown in FIG. 7B, the chambers 743 of the plate 703 may nest inside the chambers 735 of the plate 732, with the bottom portions of the chambers 743 and 735 being spaced apart. In the exemplary embodiment of FIGS. 7A and 7B, the chambers 743 and 735 are configured as wells, however, those having skill in the art would recognize numerous other configurations, including, for example, tubes, that the chambers may have.

As mentioned above, the electrophoresis matrix 701 also includes a combination electrode filter plate 704. The electrode filter plate 704 may include a substantially planar electrode 705, which in the exemplary embodiment may be embedded in or deposited on a surface of the plate 704. In various exemplary embodiments (not depicted), the electrode 705 may be perforated (e.g., have a mesh-like structure) to permit air and other gases from the chambers 743 and 735 to escape from the system 700. Extending from contact with the planar electrode 705 are a plurality of electrode posts 706, for example wire posts, arranged so as to correspond to the positioning of respective chambers 743 when the electrode plate 704 is aligned with the plate 703. In other words, each electrode post 706 is configured to be received by a respective chamber 743. The electrode filter plate 704 also may include a plurality of electrodes 715 configured to be respectively received in the plurality of sample chambers 735 when the plates 704, 703, and 732 are placed in the nesting relationship shown in FIG. 7B. In various exemplary embodiments, the electrodes 715 may be wires of an appropriate length and shape to be positioned such that their respective free ends are disposed near the closed bottom end of the sample chambers 735 when the plates 704, 703, and 732 are placed in a nesting relationship. In various exemplary embodiments, the electrodes 715 may be provided with an electrically insulative material (e.g., cladding) on an exterior thereof along substantially the entire length of the electrodes 715 up to about the free end so that the electric field between the electrode 705 and 715 may be applied to a majority of the sample contained in the sample chambers 735.

A power supply 760 may be configured to be placed in electrical connection with the electrodes 705 and 715 to supply power thereto. Upon the supply of power from the power supply 760, the electrode 705 and electrode posts 706 may become negatively charged and the electrodes 715 may become positively charged, and an electric field may be generated therebetween.

As best shown in FIG. 7B, the chambers 743 may have a bottom portion that is configured to permit passage of various substances. In particular, the bottom portion of the chambers 743 may be formed of a filter 730. The electrode filter plate 704 may be provided with another filter 710 surrounding the electrode post 706 and extending along the length of the electrode layer 705. In various exemplary embodiments, the filters 710 and 730 may also be made of porous gels (e.g., agarose, polyacrylimide, or other similar porous gel), as described above with reference to other exemplary embodiments of the present teachings. The filters 710 and 730 may be size exclusion filters with the filter 730 configured to pass particles of larger size than the filter 710. The filter 710 may be provided as a coating along an underside of the electrode layer 705 and along the outer surface of the electrode posts 706. Both filters 710 and 730 may be made of an electrically conductive material or otherwise saturated (e.g., a gel made with) with an electrically conductive buffer, such as, for example, a TBE buffer. Of course, those having ordinary skill in the art would recognize that the filters 710 and 730 may be made of various other materials, such as, for example, beads, porous metals (e.g., formed with laser holes), fibers, gels, etc. and the sample chambers 743 and plate 704 may have structures to support such materials.

Those having ordinary skill in the art would recognize that the configurations of the electrode layer 705, electrode posts 706, and electrodes 715 are exemplary only and nonlimiting. Various other configurations for the electrodes may be used to generate an appropriate electric field to achieve migration of charged particles from the sample holder 732 to a collection area. For example, it should be understood that electrodes could be embedded in the sample holder 732 similar to the exemplary embodiment depicted in FIGS. 5 and 6.

Figures 8A, 8B, 8C, 8D:
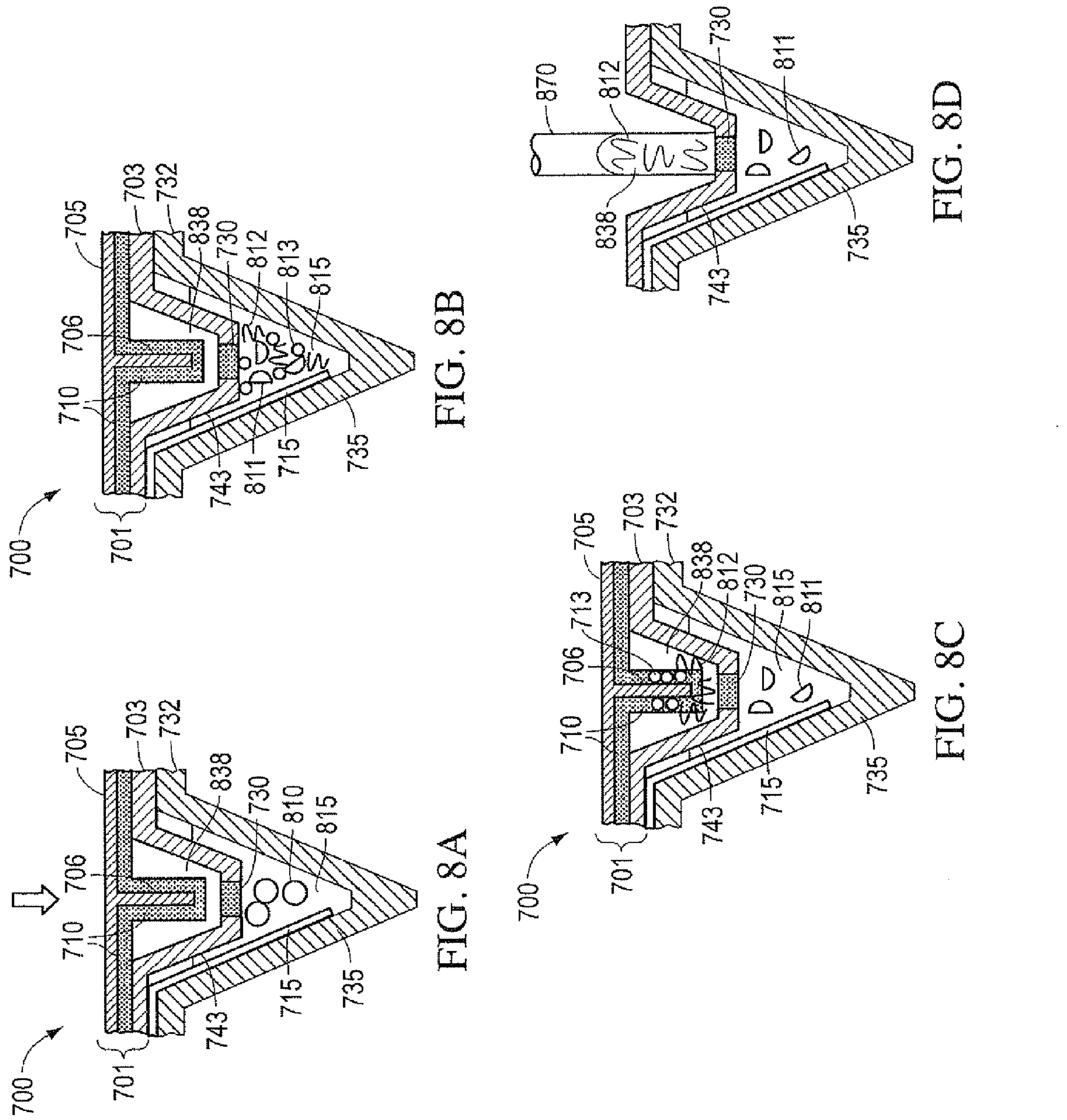
FIGS. 8A-8D show an exemplary embodiment of operating the system of FIGS. 7A and 7B in accordance with the present teachings.

An exemplary operation of the electrophoresis-based system 700 will now be described with reference to FIGS. 8A-8D. As with exemplary embodiments described above, for ease of illustration, the cross-sectional views of FIGS. 8A-8D are partial, depicting a section of the system 700 through only a single sample chamber 735. In FIG. 8A, a sample containing entities containing nucleic acids, such as, for example, cells 810 and a lysing reagent 815 may be introduced into each of the sample chambers 735 of the sample holder 732. In various exemplary embodiments, the lysing reagent 815 may be predeposited in the chambers 735 or may be added at the same time or after the sample containing cells 810. The arrow depicts introduction of the sample and, if not predeposited, the lysing reagent 815, into the chamber 735. In various exemplary embodiments, the lysing reagent may be electrically conductive. Alternatively, an electrically conductive medium separate from the lysing reagent 815 also may be added to the sample chambers 735, Optionally, a heater/shaker plate 750 may be activated to heat and/or agitate the sample holder 732 and assist in disrupting the cells containing target nucleic acids in the sample and/or other disruption techniques may be utilized in lieu of or in conjunction with chemical lysing, as has been described above with reference to other exemplary embodiments. Also, as has been discussed above in describing other exemplary embodiments, the sample and cells 810 therein may be subjected to one or more disruption techniques prior to be introduced in to the chambers 735.

The electrophoresis matrix 701 may be aligned and positioned over the sample holder 732 after addition of the sample 810 and lysing reagent 815 such that the chambers 743 and electrodes 715 are inserted into sample chambers 735. In this configuration, the sample chambers 735 may be sealed by the electrophoresis matrix 701 during disruption. The collection chambers 743 may be filled with an electrically conductive medium (e.g., an electrolyte) 838 in order to perform electrophoresis as will be described. Such electrically conductive medium 838 may either be predeposited in the collection chambers 743 or may be added to the chambers 743 before matrix 701 is used for sample preparation.

In various exemplary embodiments, the positioning of the matrix 701 relative to the sample holder 732 may occur manually or via an automated mechanism (not shown) such as, for example, a robotic transfer mechanism. Skilled artisans would understand various automated mechanisms, including, but not limited to, for example, the mechanism 370 in the exemplary embodiment of FIG. 3A, that could be used to move the matrix 701 into position relative to the sample holder 732. Once the matrix 701 is positioned appropriately relative to the respective sample chambers 735 and the cells 810 of the raw sample have been disrupted to release target nucleic acids 812, as shown in FIG. 8B, the electrodes 705 and 715 may be supplied power from the power source 760 (shown in FIG. 7A) thereby generating an electric field between the electrodes 705 and 715 via the electrically conductive media 815, 838, 710, and 730.

With electrode 705 being positively charged and electrode 715 being negatively charged, negatively charged particles in the sample chamber 735, including, for example, target nucleic acids 812, may migrate away from electrode 715 and toward electrode post 706 and electrode 705. Because the filters 710 and 730 are electrically conductive, whether by being saturated with an electrically conductive medium or otherwise made of an electrically conductive material, the electric field between the electrode 705 and the electrode 715 will extend through the filters 710 and 730 disposed between the electrode 705 and electrode 715, causing negatively charged material in the disrupted sample to migrate toward the filters 710 and 730. The filter 730 may be configured to permit passage of target nucleic acids 812 while blocking passage of larger negatively charged particles, such as cell debris 811, on the basis of size. If the disrupted sample also contains negatively charged, smaller particles 813, such as impurities (e.g., other than the cell debris 811), the filter 710 may be used and configured to block passage of the larger target nucleic acids 812 and permit passage of smaller, negatively-charged particles 813. Other particles (not shown) in the sample chambers 735 that are not charged or are positively charged will remain in sample chamber 735.

After sufficient time has elapsed, the target nucleic acids 812 will have migrated via electrophoresis through the filter 730 and the smaller, negatively-charged particles 813 will have migrated into the filter 710. Electrophoresis may be allowed to continue until the target nucleic acids 812 pass through filter 730 and into the chamber 743 and the smaller, negatively-charged particles 813 pass through the filter 730 and into the filter 710 where they are captured, as shown in FIG. 8C. Once the target nucleic acids 812 have been separated and collected in collection chamber 743 and any smaller, negatively-charged particles 813 have been separated from the target nucleic acids 812 and collected in the filter 710, power to the electrodes 705, 706 and 715 may be removed and the electrode plate 704 may be removed from the separation plate 703, leaving the chambers 743 exposed and containing the isolated target nucleic acids 812 and electrically conductive medium 838. A removal device 870, such as, for example, a needle, pipette, or other type of removal device may be used to remove the capture target nucleic acids 812 and the electrically conductive medium 838 from the chambers 743, as shown in FIG. 8D. The concentrated and isolated target nucleic acids may then optionally be brought to another location and/or deposited into another sample holder (not shown) for further processing and/or analyzing, such as PCR for example, of the target nucleic acids 812, as desired.

The various exemplary embodiments for operating the electrophoresis-based sample preparation systems described above involve a single disruption procedure (although numerous techniques may be used individually or in combination to achieve such disruption) to release target nucleic acids from entities containing the target nucleic acids in a sample. The various exemplary systems described herein, both above and further below, however, may be used to isolate and collect nucleic acids from a sample that contains differing types of entities containing nucleic acids (e.g., pathogens and/or other cells). By way of example only, the sample could include entities containing target nucleic acids and other entities containing nontarget nucleic acids and it may be desirable to separate the former from the latter. Alternatively, the mixture of entity types may include differing types of target nucleic acids and it may be desirable to extract, isolate, and/or separately collect each of the differing target nucleic acids without having the differing types contaminate (e.g., be mixed with) each other once collected.

To achieve such separation, the exemplary systems described herein may be operated to perform multiple disruption steps and multiple electrophoresis separation and collection steps. By way of example only, entities for which disruption is easier in such a mixture may be subjected to a first disruption step and entities that are more difficult to disrupt may be subjected to a second disruption step; after each disruption step, the released nucleic acids may be subjected to electrophoresis for separation and collection. The description that follows sets forth an exemplary operation for using the exemplary embodiment of FIGS. 7A and 7B for extracting, separating, and collecting differing types of nucleic acids from a sample that contains a mixture of cells of two differing types. Those having ordinary skill in the art will recognize that the number of differing types of cells or other entities containing nucleic acids in a sample may be more than two and in such cases, the disruption, electrophoresis separation, and collection steps may be repeated as needed to isolate and collect differing types of nucleic acids (for example, including target and nontarget nucleic acids) from such a sample. Moreover, although the exemplary operation that will now be described refers to use of the exemplary embodiment of FIGS. 7A and 7B, those having ordinary skill in the art would readily understand from the following description and teachings how to utilize the exemplary systems of FIGS. 1A and 1B, 3A and 3B, and 5A and 5B to achieve extraction, isolation, and collection of differing types of nucleic acids from a sample containing differing types of cells and/or other entities containing nucleic acids.

Referring to FIGS. 9A-9H, an exemplary embodiment of using the electrophoresis-based sample preparation system 700 to extract, separate and collect nucleic acids from a sample containing a mixture of sperm cells (S-cells) and epithelial cells (E-cells) is described. It will be understood that the operation set forth in FIGS. 9A-9H is not limited to separating nucleic acids from a mixture of S-celis and E-cells and may be applied to various mixtures of differing cell types. Separating nucleic acids (e.g., DNA) from a sample containing both S-cells and E-cells under some conventional forensics techniques can take several hours, for example up to 8 hours. Moreover, conventional techniques may result in nucleic acids from E-cells contaminated with nucleic acids from S-cells and vice versa. The electrophoresis-based sample preparation systems described herein may be used to achieve relatively efficient separation and collection of nucleic acids from S-cells from E-cells, yielding relatively rapid separation and collection with substantially no contamination between the two types of collected nucleic acids. The entire procedure of disruption, electrophoresis separation and collection taking from about 5 minutes to about 60 minutes, with subsequent PCR on the collected nucleic acids taking from about 30 minutes to about 120 minutes.

Figure 9B:
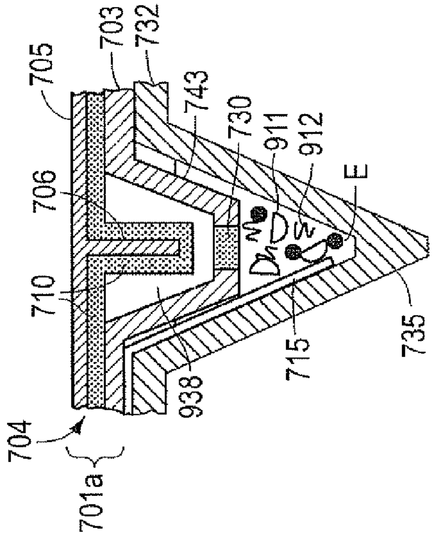
FIGS. 9A-9H show another exemplary embodiment of operating the system of FIGS. 7A and 7B in accordance with the present teachings.
Figure 9A:
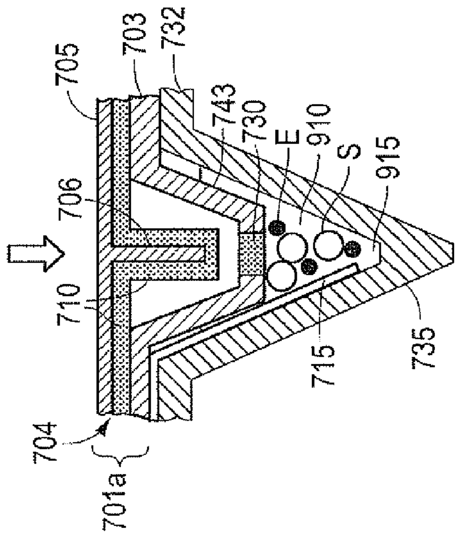
Figure 9D:
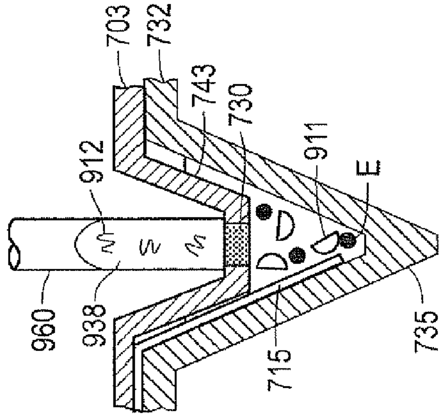

In FIG. 9A, a sample 910 containing a mixture of S-celis S and E-cells E are placed in the sample chambers 735 of the sample holder 732. A lysing reagent 915 also may be provided in the sample chambers 735, either via predeposition in the chambers 735 or added to the sample chambers 735 with or after the sample 910. The lysing reagent 915 may be electrically conductive, for example a TBE buffer, or an electrically conductive substance may be added to the lysing reagent 915 for the purposes of conducting electrophoresis. In any case, the lysing reagent 915 may be selected so as to effect the lysing of the S-cells S but not the E-celis E. The electrophoresis matrix 701, with an electrically conductive medium 938 in the chambers 743 may be positioned in cooperating relationship with the sample holder 732 so as to seal the chambers 735 during lysis.

After a sufficient time period under the influence of a disruption mechanism, for example lysing reagent 915 and/or optionally with a mechanical (e.g., agitation, vibration, sonication, etc.), thermal, and/or other disruption mechanism with which those ordinarily skilled in the art are familiar and which have been described herein, the S-cells S may rupture releasing S-nucleic acids 912, as depicted in FIG. 9B. Once the S-nucleic acids 912 have been released, the electrodes 705 and 715 may be activated with the electrode 705 and electrode posts 706 becoming positively charged and the electrodes 715 becoming negatively charged. Due the presence of an electrically conductive medium 938 in the chamber 743, the electrically conductive lysing reagent 915 or other electrically conductive medium in chamber 735, and soaked filters 710 and 730, negatively charged S-nucleic acids 912 may migrate under electrophoresis toward the electrode post 706 and through the filter 730. The filter 730 may be sized so as to allow passage of the negatively charged S-nucleic acids 912 while blocking passage of larger negatively-charged particles, such as, for example, the S-cell debris 911 and the E-cells E. Any positively-charged or neutrally-charged material in the sample chambers 735 will remain in the chamber 735 while the electrodes 705 and 715 are activated and generate an electric field.

If the sample of FIG. 9B that has been subject to disruption also contains negatively-charged particles (e.g., impurities other than S-cell debris 911) that are smaller than the S-nucleic acids 912, the filter 710 may be used to collect such negatively-charged smaller particles (not shown), in a manner similar to that described with reference to FIGS. 8A-8D. That is, electrophoresis may continue until the smaller, negatively charged particles migrate and are captured in the filter 710. The configuration of filter 710 may be such that it blocks the S-nucleic acids 912 from passage based on size exclusion.

Figure 9C:
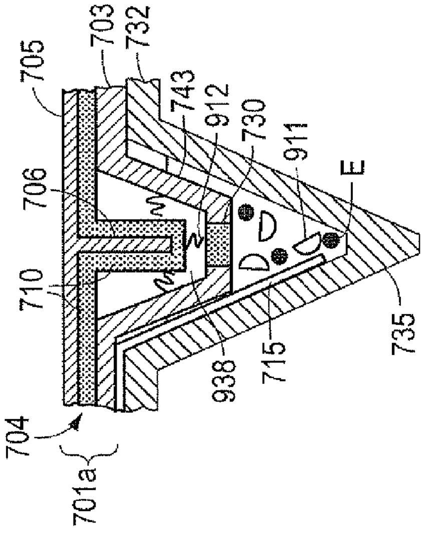

Once the S-nucleic acids 912 have been passed to the chambers 743, as shown in FIG. 9C, and smaller negatively-charged particles, if any, have been captured in filter 710, the electrodes 705 and 715 may be deactivated. In the next exemplary step shown in FIG. 9D, the combined electrode filter plate 704 may be removed from the filter plate 703 and a removal device 960, such as a needle, pipette, or other removal device, for example, may be used to remove the S-nucleic acids 912 in the medium 938 from the chambers 743. Further processing (e.g., PCR, etc.) and/or disposal of the isolated and collected S-nucleic acids 912 may optionally be performed as desired.

After removal of the S-nucleic acids, the filter plate 743 also may be removed and a second disruption step may be performed. For example, a new lysing reagent 917, shown in FIG. 9E, may be added to the chambers 735 that contain the intact E-cells, cell debris 911 from the ruptured S-cells, and the lysing reagent 915. As with previously described lysing reagents, the lysing reagent 917 may be, or may be mixed with, an electrically conductive medium. In various exemplary embodiments, the lysing reagent 917 may be a TBE buffer for example. For lysing reagents that may be used for the selective lysing of S-cells, reference is made to U.S. application Ser. No. 12/015,414, filed Jan. 16, 2008 in the name ofYingjie Jason Liu, which is incorporated by reference in its entirety herein. The lysing reagent 917 may be selected so as to lyse the E-cells E. In FIG. 9E, once the lysing reagent 917 has been added to the chambers 735, if being used to achieve disruption, a new electrophoresis matrix 701*a* having a configuration like that described above with reference to electrophoresis matrix 701 may be positioned over the sample holder 732 to seal the sample chambers 735 during lysis. The various parts of the electrophoresis matrix 701*a* are the same as those described with respect to matrix 701 and therefore will not be described in detail. Like parts are labeled with the subreference "a" in FIGS. 9E-9H. Those having ordinary skill in the art would understand, however, that the filters 710*a* and 730*a* may have different size exclusion properties than filters 710 and 730 depending on the size of the particles for which each filter 710*a* and 730*a* is intended to pass and/or block.

Figure 9F:
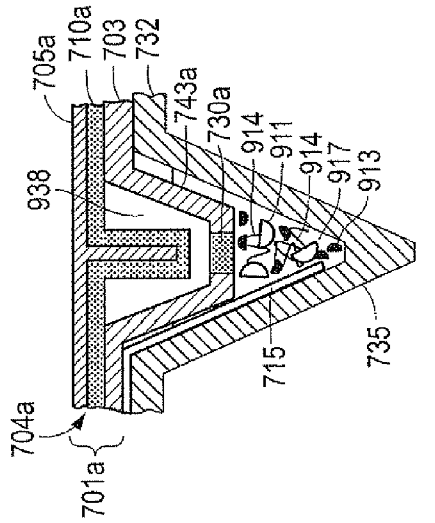
Figure 9:
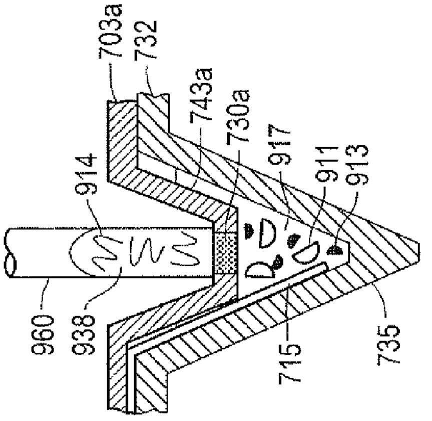
Figure 9E:
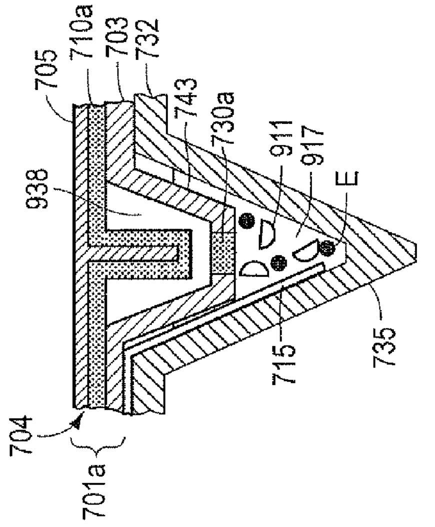
Figure 9G:
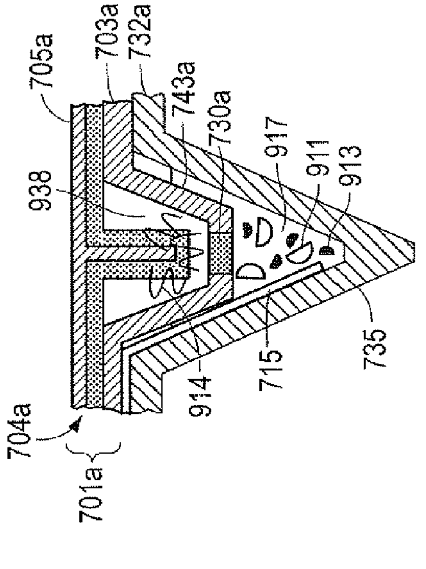

In FIG. 9F, disruption of the E-cells may continue under the influence of the lysing reagent 917, thermal, electrical, and/or mechanical action as described with reference to FIG. 9B and once the E-cells rupture to release the E-nucleic acids 914, the electrode 705*a*, electrode post 706*a*, and electrode 715*a* may be activated to generate an electric field therebetween. The electric field may cause the E-nucleic acids 914 to migrate via electrophoresis through the filter 730*a* and into the chambers 743*a*, leaving particles, such as S-cell debris 911 and E-cell debris 913 in chambers 735. Electrophoresis via activation of the electrodes 705*a* and 715*a* may continue to isolate and collect in filter 710*a* smaller, negatively-charged particles (e.g., impurities other than S- and E-cell debris) (not shown), in a manner similar to that described with reference to FIG. 9C. The filter 710*a* may be configured to block the passage of the E-nucleic acids 914 on the basis of size, and the filter 730*a* may be configured to block the passage of any other negatively charged material larger than the E-nucleic acids 914. After extraction and electrophoretic separation of the E-nucleic acids 914 into the chambers 743*a*, as shown in FIG. 9G, power to the electrodes 705*a*, 706*a*, and 715*a* may be stopped, the combined electrode filter plate 704*a* removed, and a removal device 960 used to remove the separated E-nucleic acids 914 and medium 938. Further processing (e.g., PCR) and/or disposal of the isolated E-nucleic acids 914 may optionally be performed as desired.

Electrophoresis-based nucleic acid isolation systems may also be useful for pathogen testing. A challenge that can arise in this setting includes detecting a relatively small amount of bacteria in a relatively large sample size (e.g., such as a food product sample or sample from equipment handling such products). Determining the existence of one or a few pathogens in relatively large sample size, for example on the order of dozens of grams in the case of a meat product, can be like trying to find a needle in a haystack. PCR detection has the capability of detecting relatively small amounts of nucleic acids. However, conventional PCR tooling platforms (such as, for example, titer plates) may not be amenable to handling large sample sizes that accompany food pathogen detection. Using electrophoresis-based sample preparation systems may permit pathogen nucleic acids from a single bacterial cell or a relatively small amount of such cells in a relatively large sample size to be extracted, separated from the rest of the sample, and collected. Various exemplary embodiments of electrophoresis-based sample preparation systems configured to accommodate relatively large sample sizes, like those that may be found in a food pathogen detection application, are described below. The electrophoresis-based systems in various exemplary embodiments may have the ability to process a relatively large sample size to extract and isolate target nucleic acids in the sample and collect such target nucleic acids in an amount suitable for performing conventional PCR detection and/or other biological assays.

Figure 10:
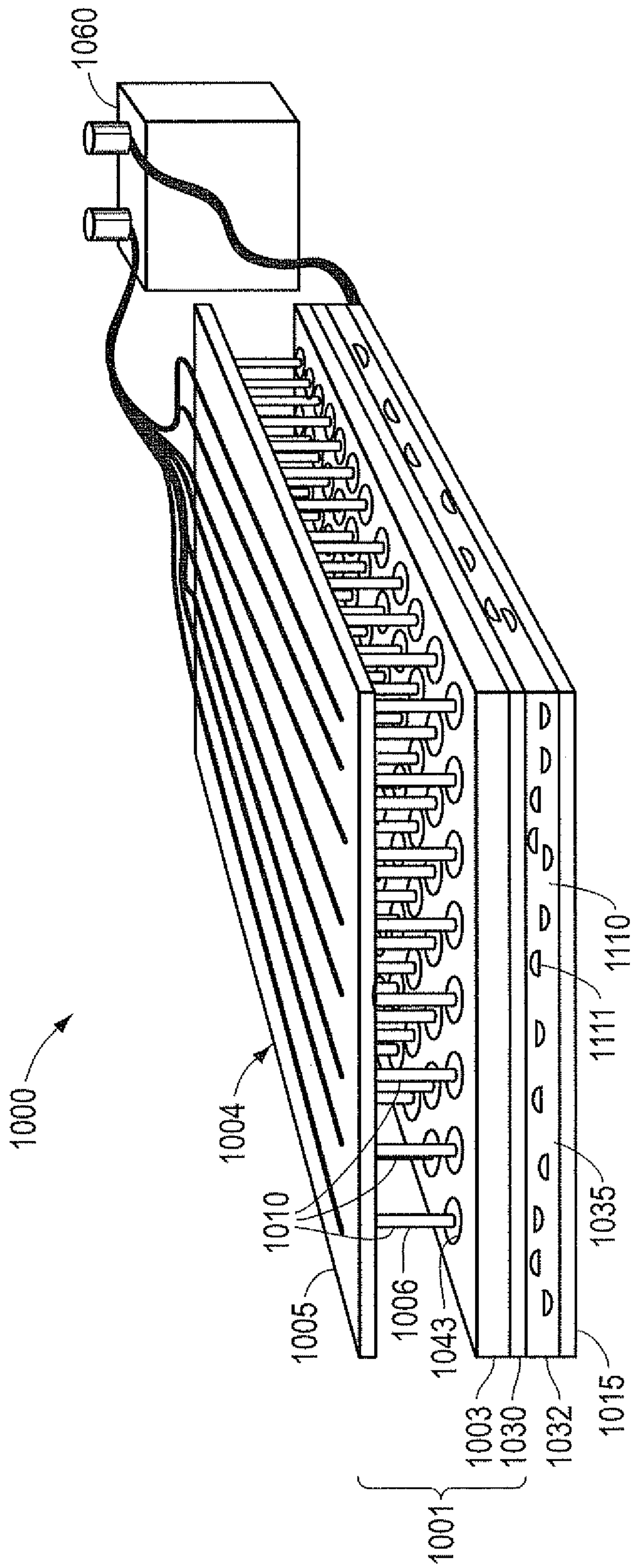
FIG. 10 is a perspective view of another exemplary embodiment of an electrophoresis-based sample preparation system.

FIGS. 10-13 illustrate an exemplary embodiment of an electrophoresis-based system and exemplary operation of the system for extracting, isolating, and collecting target pathogen nucleic acids from a food product containing host cells, for example hamburger meat containing host cow cells. With reference to FIG. 10, an electrophoresis-based system 1000 may include a sample plate 1032 having an electrode 1015 on a bottom of the plate 1032. The plate 1032 may define a single sample chamber 1035, for example having a volume ranging from about 1 ml to about 500 ml, for example about 50 ml. The chamber 1035 may be configured to receive a sample from a food product, for example, water that washed equipment handling a food product, water that washed the food product, including vegetables, poultry, fish, beef, etc., or the food product itself. The sample may be pulverized and/or stomacked, if needed, and also subjected to disruption. If the sample food product includes both host cells and pathogens, for example when the sample is the food product itself disruption may release both pathogen nucleic acids and host nucleic acids. In various exemplary embodiments, the thickness of the sample plate 1032 may range from about 3 mm to about 30 mm, for example, the thickness may be about 5 mm.

The system also may include an electrophoresis matrix 1001 that includes a separation plate 1003 and a filter layer 1030 between the separation plate 1003 and the chamber 1035. In the exemplary embodiment of FIG. 10, the separation plate 1003 is a titer plate defining a plurality of collection chambers 1043 (e.g., wells) with openings in the bottom thereof to place the chambers 1043 in flow communication with the chamber 1035 through the filter layer 1030. In an alternative configuration, the filter layer 1030 may be removed and each of the bottom portions of the chambers 1043 may be provided with filters similar to the configuration of the plates 502 and 503 described above with reference to the exemplary embodiment of FIGS. 5A and 5B. As described above with reference to various exemplary embodiments of the present teachings, in the case of filter 1030 being a porous gel, it may be formed by solidification of a liquid substance to a gel. For other types of filters, those skilled in the art would understand how to form such filters and secure them appropriately to the electrophoresis matrix plate 1001.

The separation plate 1003 and filter 1030 may be positioned over the sample holder 1032 so as to substantially align with the sample holder 1032 and seal the sample chamber 1035, as shown in FIG. 10. The system 1000 may further include an electrode plate 1004 having a planar electrode portion 1005 and plurality of electrode posts 1006 that extend vertically from the portion 1005. The plurality of electrode posts 1006 may be arranged so as to correspond to respective chambers 1043 of the separation plate 1003 when the electrode plate 1004 is aligned with the separation plate 1003. The posts 1006 also may be configured to be received by the chambers 1043 such that the free ends of the posts 1006 are disposed proximate the bottoms of the chambers 1043. The collection chambers 1043 may be filled with an electrolyte or other electrically conductive medium. Electrode 1005 and electrode 1015 may be configured to be placed in electrical connection with a power supply 1060 to activate the electrodes 10051 electrode posts 1006 and electrode 1015. The electrode 1015 may become negatively charged when activated and the electrode 1005 and posts 1006 may become positively charged, thereby establishing an electric field between the electrode 1005/electrode posts 1006 and the electrode 1015.

The electrode posts 1006 may be provided with a filter material 1010 on an exterior surface of the posts 1006. By way of example, a porous gel may be used to coat the exterior surface of the posts 1006. Other filter materials that have been described herein also may be used and supported around the exterior of the electrode posts 1006 and those having skill in the art would recognize appropriate modifications to the structure of the electrode plate 1004 and posts 1006 in order to provide supporting structure for various filter materials, including, for example, beads, fibers, metals, etc. For example, the electrode posts 1006 may be housed in a sheath or the like and a filter material held between the sheath and the posts 1006. Regardless of its structure, the filter 1010 may be configured as a size exclusion filter and may block the passage of particles that a filter 1030 may permit passage of. In this way, as will be explained in more detail below, the filter 1010 may be configured to trap small negatively-charged impurities in the lysed sample 1110 while blocking the entry of the larger target nucleic acids (e.g., pathogen nucleic acids) from the sample 1110.

To use the system 1000 of FIG. 10, for example to isolate pathogen nucleic acids from the sample, a sample of food product 1110 that has been subjected to disruption and, if needed, stomacked, may be placed in the sample chamber 1035 of the sample holder 1032. The lysed sample 1110 may contain both pathogen nucleic acids and, if the food product itself is the sample, host nucleic acids (e.g., cow nucleic acids in the case of beef. In various exemplary embodiments, disruption should not significantly shear the nucleic acids so that host nucleic acids may remain relatively large (e.g., on the order of 31 Mbp for the smallest cow chromosome) compared to relatively small pathogen nucleic acids (e.g., about 0.6 Mbp to about 10 Mbp). The disrupted sample 1110 also may contain cell debris 1111 remaining from disruption and/or other small particles, such as, for example, proteins, impurities other than cell debris, etc. The sample 1110 may also contain an electrically conductive medium, which may be included in a lysis medium or may be otherwise added to disrupted sample 1110.

The separation plate 1003 and filter 1030 may be positioned over the sample holder 1032, and the electrode plate 1004 may be positioned over the separation plate 1003 such that the electrode posts 1006 are positioned with their free ends proximate a bottom of the chambers 1043, respectively. Power may be then be supplied to the electrodes 1005 and 1015 via the power supply 1060 causing the electrode 1015 to become negatively charged and the electrode 1005 and electrode posts 1006 to become positively charged. The electric field generated between the electrodes 1015 and 1005, which will pass through the sample chamber 1035 and the filters 1010 and 1030 (which may be saturated with an electrically conductive medium or may be made of an electrically conductive material) may cause migration via electrophoresis of negatively-charged material in the sample 1110 away from electrode 1015 and toward the electrode posts 1006 and electrode 1005.

As mentioned above, the filter 1030 may be configured so as to permit the passage of pathogen nucleic acids while blocking the passage of host nucleic acids and other negatively charged material that is larger in size than the pathogen nucleic acids. The filter material 1010 associated with the electrode posts 1006 may be configured to block the passage of the pathogen nucleic acids while permitting passage of negatively charged particles that are smaller than the pathogen nucleic acids, for example, impurities. After a sufficient time period such that electrophoresis has caused impurities to migrate to and be captured in filter 1010 and the pathogen nucleic acids to migrate through the filter 1030 and be collected in the chambers 1043, the electrodes 1005 and 1015 may be deactivated. In various exemplary embodiments, the chambers 1043 may have a volume ranging from about 1 microliter to about 100 microliters, for example, for a 96-well titer plate, the chambers 1043 may have a volume of about 5 microliters each. The isolated pathogen nucleic acids collected in the chambers 1043 may at this point optionally be further processed and/or analyzed as desired, for example, via PCR detection.

Figure 11:
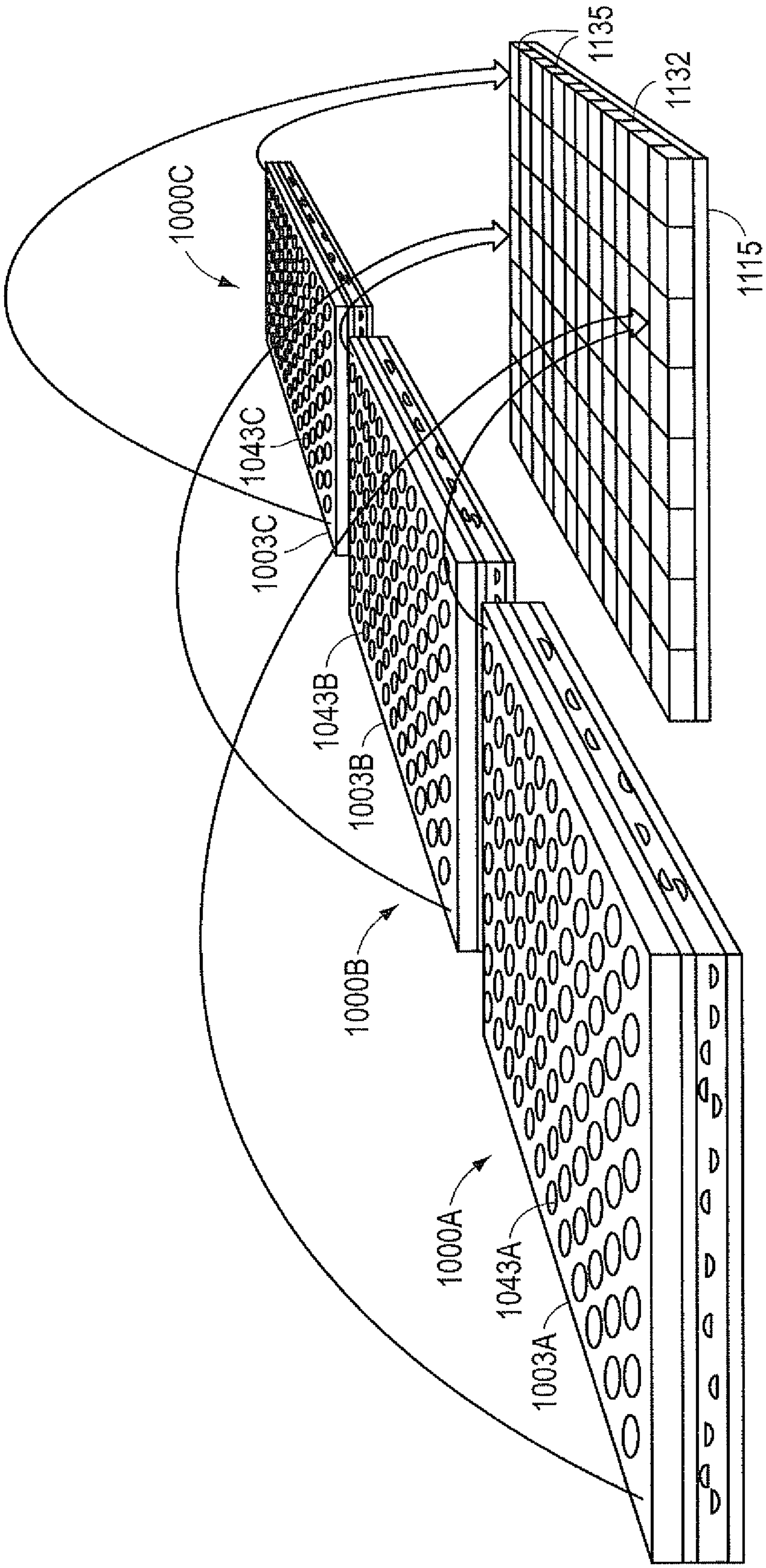
FIGS. 11-13 show exemplary steps for operating the system of FIG. 10.

In an exemplary embodiment, as illustrated in FIG. 11, a plurality of electrophoresis-based systems 1000A, 1000B, and 1000C may be used to perform parallel processing of a sample, for example by dividing a relatively large volume of a sample into plural amounts. The electrophoresis-based systems 1000A, 1000B, and 1000C also may be used to perform parallel processing of differing samples (e.g., from differing sample lots). Upon isolation and collection of the pathogen nucleic acids in the chambers 1043A, 1043B, and 1043C of each separation plate 1003A, 1003B, and 1003C, the collected pathogen nucleic acids from each separation plate 1003A, 1003B, and 1003C, respectively, may be transferred to another sample holder 1132. More specifically, the sample holder 1132 may have a plurality of sample chambers 1135. Each sample chamber 1135 may have a volume sufficient to hold the total volume of all the chambers 1043A, 1043B, or 1043C of a respective separation plate 1003A, 1003B, or 1003C. By way of example only, in the case where the plates 1003A-1003C have 96 sample chambers 1043A, 1043B, 1043C each, with each sample chamber having a volume of about 5 microliters, the sample holder 1132 may also have 96 sample chambers 1135, each having a volume of about 500 microliters. Those having ordinary skill in the art would understand that the volumes and number of sample chambers may vary depending on the application. The sample holder 1132 also may have an electrode 1115, for example a planar electrode, disposed at a bottom thereof. Those having skill in the art would understand that the number of separation plates 1000 used in the transfer step of the exemplary embodiment of FIG. 11 may be equal to or less than the number of chambers 1135 of the sample holder 1132.

Figure 12:
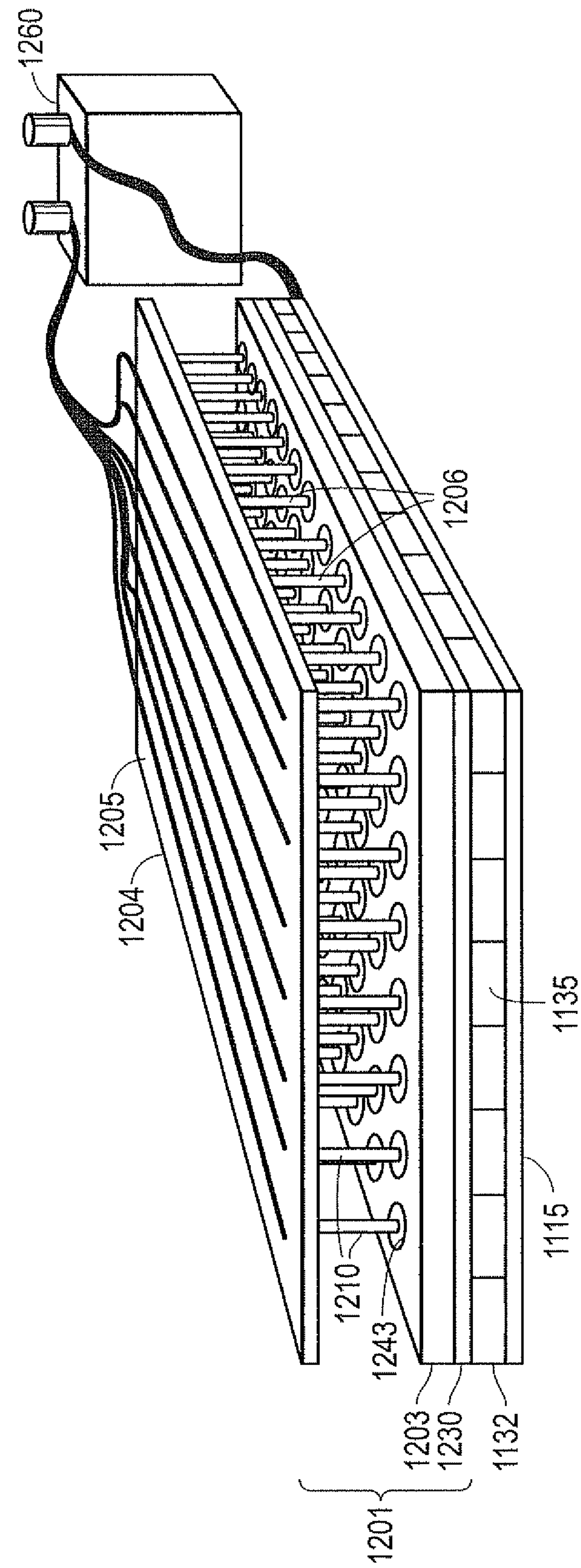
Figure 13:
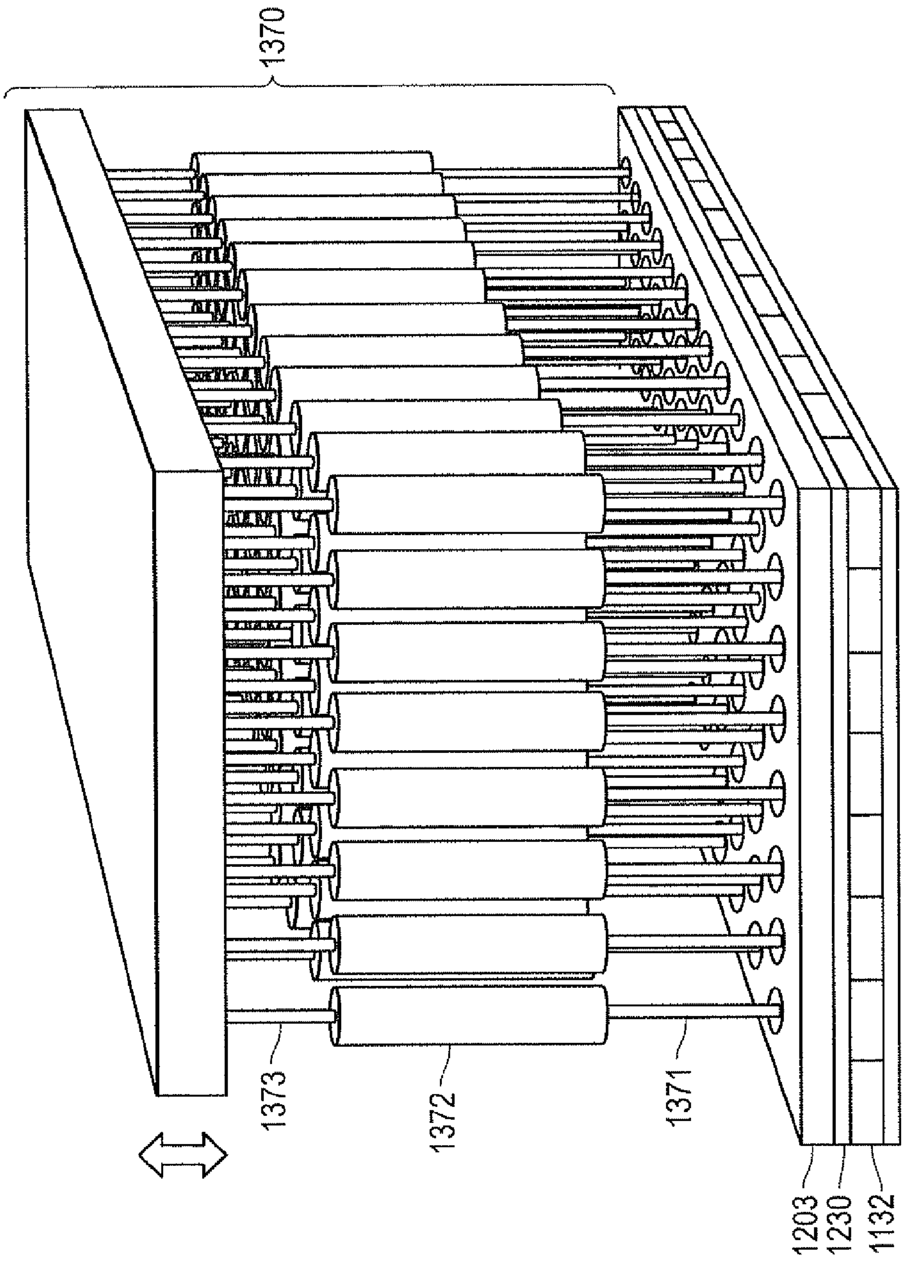

The transfer process depicted in FIG. 11 may be performed manually, for example, via manual pipetting or other aspiration, or via an automated liquid handling device, such as, for example, a syringe pump device 1370 depicted in FIG. 13. After performing the transfer process depicted in FIG. 11, the sample holder 1132 contains an isolated nucleic acid sample in each chamber 1135. With reference to FIG. 12, the sample holder 1132 may be placed in cooperation with another electrophoresis-based preparation matrix 1201 having a filter 1230, separation plate 1203 with chambers 1243, an electrode plate 1204 with planar electrode 1205 and electrode posts 1206, and having an overall structure similar to the electrophoresis matrix 1000 discussed with reference to FIG. 10. Electrophoresis may be performed again in the exemplary operation of FIG. 12 to isolate the pathogen nucleic acids from each sample in the chambers 1135 and collect the isolated pathogen nucleic acids in the respective chambers 1243. The chambers 1243 may have a volume similar to the volume of the chambers 1043. Thus, in FIG. 12, the volume of the samples from the initial amount in the larger chambers 1135 is reduced for the isolated and collected nucleic acids, for example from about 500 milliliters to about 5 microliters.

After collecting the pathogen nucleic acids in the chambers 1243 and also removing impurities, if any, by capturing them in the filter 1210 associated with electrode posts 1206, electrophoresis may be stopped and electrophoresis matrix 1201 removed. The nucleic acids in the chambers 1243 may be collected, either manually or via an automated liquid handling mechanism, such as, for example, the syringe pump device 1370 comprising a plurality of needles 1371, syringe barrels 1372, and automatic plungers 1373 depicted in FIG. 13. Those ordinarily skilled in the art would understand the configuration of a suitable syringe pump for use in removing substance from the chambers 1243, such syringe pumps being conventionally used in various biological assay applications.

The exemplary embodiments of FIGS. 11-13 therefore provide a relatively rapid food pathogen detection technique, on the order of several minutes to perform disruption and electrophoresis. By using the parallel, iterative process of the exemplary embodiments of FIGS. 11-13, multiple, smaller sample sizes may be processed at a time (e.g., in the plates 1000A-1000C), thereby leading to faster electrophoresis isolation times for target nucleic acids. Although an iterative process of isolating, collecting, and isolating again may not be necessary, such an iterative process may provide collected nucleic acid sample sizes amenable to PCR detection techniques. Further, because the sample amounts associated with each of the plates 1000A-1000C are relatively small, it may be desirable to perform parallel processing on multiple plates at a time to help ensure that the nucleic acids collected include target nucleic acids, such as, for example, pathogen nucleic acids. Using only a single plate 1000A-1000C may require that only a portion of an overall sample be subjected to nucleic acid isolation and detection and that selected portion may not contain the target nucleic acids if the overall sample is relatively large in size.

Thus, the exemplary embodiments of FIGS. 11-13 may permit handling a relatively large sample size typically associated with food samples and permitting collection of a relatively pure small sample size of target (e.g., pathogen) nucleic acids to further analyze (e.g., via PCR detection). The exemplary embodiments also permit isolation of a relatively small amount of pathogen nucleic acids that may be mixed with a relatively large amount of host nucleic acids, thereby reducing noise due to the presence of host nucleic acids during PCR detection. In exemplary embodiments, automated liquid handling and tooling that is configured for conventional PCR platforms may be utilized.

Although only the exemplary embodiment of FIGS. 11-13 have been described with reference to disruption of a single entity type and collecting nucleic acids from that entity type, it should be understood that a multiple-step disruption process for disrupting two or more differing types of entities containing nucleic acids and collecting the respective nucleic acids from the differing entity types may also be performed using the system of FIGS. 11-13. In such a case, all of the steps described above with reference to FIGS. 10-13 may be repeated for each disruption procedure. That is, after a first disruption procedure releasing a first type of nucleic acids from the sample in sample chamber 1032, the steps of FIGS. 10-13 would be performed and may then be repeated after a second disruption procedure releasing a second type of nucleic acids from the remaining sample in sample chamber 1032.

Figure 14A:
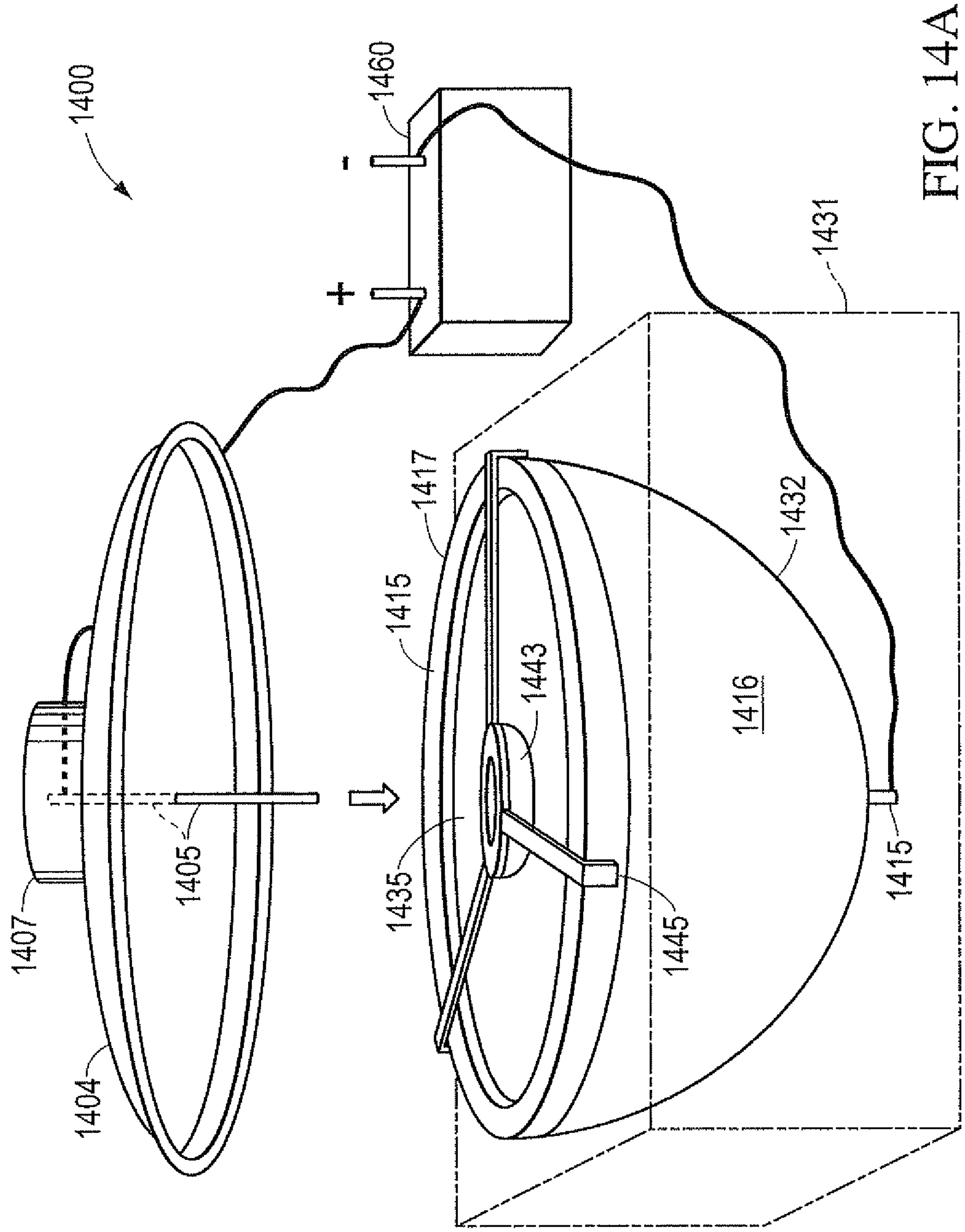
FIG. 14A is a perspective view with some internal features depicted of yet another exemplary embodiment of an electrophoresis-based sample preparation system in accordance with the present teachings.
Figure 14B:
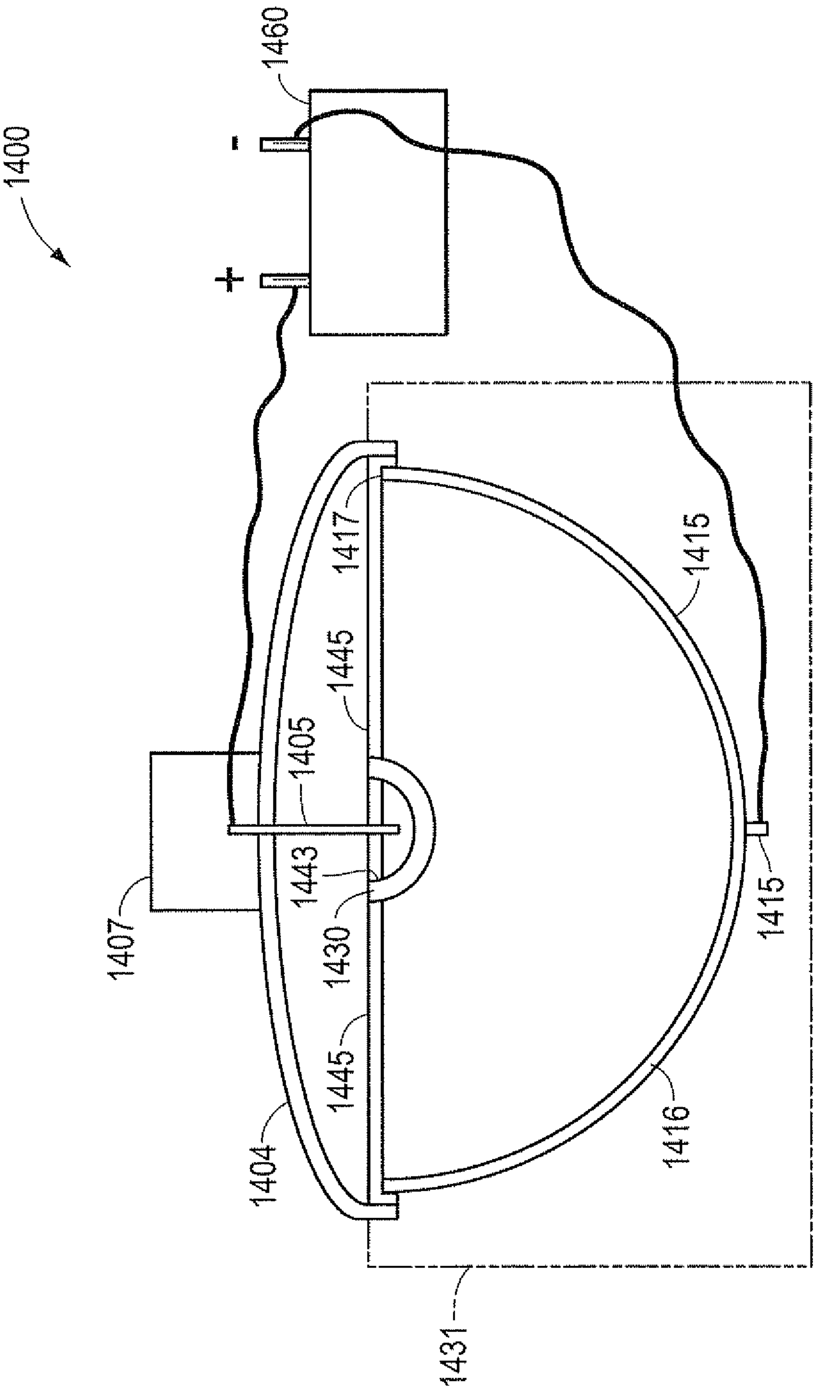
FIG. 14B is a cross-sectional view of the system of FIG. 14A.

Another exemplary embodiment of an electrophoresis-based sample preparation system is illustrated in FIGS. 14A and 14B. FIG. 14A is an isometric view of the electrophoresis-based sample system 1400 and FIG. 14B is a cross-sectional view of the system 1400 in an assembled state for isolating and collecting target nucleic acids via electrophoresis. The system 1400 is relatively robust, having a limited number of parts and being relatively easy to operate. The configuration of the system 1400, as will be apparent from the description that follows, may be particularly suitable for food pathogen detection applications as it can accommodate relatively large sample sizes on which to perform electrophoresis-based sample preparation.

The electrophoresis-based sample preparation system 1400 shown in FIGS. 14A and 14B includes a base 1431 that houses an electrode 1415. In the exemplary embodiment shown in FIGS. 14A and 14B, the electrode 1415 has a dome shape with a closed bottom end 1416 and open upper end 1417. The electrode 1415 defines a sample chamber 1435 configured to receive a sample for preparation. Although other configurations for the sample chamber 1415 may be used, the dome configuration may permit electrophoresis in three-dimensions. In various exemplary embodiments, the sample chamber 1435 defined by the electrode 1415 may have a volume ranging from about 1 ml to about 1000 ml. The size of the sample chamber 1435 may be sufficient to receive a relatively large sample size, such as, for example, sample sizes that are typically associated with food pathogen detection applications. The electrode 1415 may be configured to be placed in electrical connection with a power source 1460 and when supplied power, may become negatively charged. The base 1431 that houses the electrode 1415 may be made of an electrically insulative material to permit handling of the system 1400 without making contact with the electrode 1415. The electrode 1415 may be made of any suitable electrically conductive material, including, but not limited to, platinum, silver, copper, aluminum, electrically conductive plastics, etc.

Disposed in the opening at the open upper end 1417 of the electrode 1415 is a collection chamber 1443. The collection chamber 1443 may be defined by a filter material 1430 and have a substantially dome-shaped structure. The collection chamber 1443 may be relatively small compared to the chamber 1435, with a volume ranging from about 10 microliters to about 1000 microliters. The collection chamber 1443 may be placed substantially near a center of the open upper end 1417 of the electrode 1415. In other words, the collection chamber 1443 may be substantially concentrically disposed relative to the open upper end 1417. A plurality of support members 1445 may extend substantially radially from the collection chamber 1443 and into engagement with the upper end 1417 of the electrode 1415 to hold the collection chamber 1443 in position, as shown in FIG. 14A. In the exemplary embodiment of FIG. 14A, three support members 1445 are shown, however, those having ordinary skill in the art would recognize that any number of support members 1445 may be used as needed to hold the collection chamber 1443 in position relative to the upper end 1417 of the electrode 1415.

Although the collection chamber 1443 may include a solid structural framework that supports the filter material 1430, the interior of the collection chamber 1443 and the interior of the sample chamber 1435 may be in flow communication through the filter 1430. That is, substances placed in the sample chamber 1435 may move from the sample chamber 1435 through the exterior and to the interior of the collection chamber 1443 through the filter material 1430. In various exemplary embodiments, the filter material 1430 may be selected from various porous materials, including, for example, gels, beads, perforated metals (e.g., formed with laser holes), fibers, etc. In an exemplary embodiment, the filter material 1430 may be a porous gel and the porosity may be altered as desired. For example, the filter material may be an agarose or polyacrylimide gel. Moreover, similar to other exemplary embodiments described above, the filter material 1430 may be electrically conductive or saturated with an electrically conductive medium (e.g., in the case of a gel, the gel may be formed with an electrically conductive medium). Other structural components of the collection chamber 1443, such as, for example, framework supporting the filter material 1430, may be made of non-electrically conductive materials, such as, for example, plastic. Likewise, the support members 1445 also may be made of materials that are not electrically conductive, for example plastic.

The system 1400 may further include a cover 1404 configured to mate with the upper end 1417 of the electrode 1415 to close the opening of the electrode 1415. The cover 1404 may be configured to substantially seal the sample chamber 1435. An electrode 1405 may be associated with the cover 1404 and may be configured to generate an electric field with the electrode 1415. The electrode 1405 may be a post electrode that extends through a central region of the cover 1404 such that when the cover 1404 is in mating engagement with the electrode 1415, one end of the electrode 1405 is external to the cover 1404 and the opposite end extends to proximate the bottom of the collection chamber 1443. The end of the electrode 1405 that is positioned external to the cover 1404 may be placed in electrical connection with the power supply 1460. The electrode 1405 may become positively charged upon supply of power thereto from the power supply 1460. The cover 1404 also may include a grasping portion (e.g., handle) 1407 disposed substantially at a center of the exterior surface of the cover 1404 to provide a convenient surface for holding the cover 1404 while positioning the cover 1404 onto and removing the cover 1404 from the electrode 1415. The electrode 1405 may terminate within the grasping portion 1407 to protect a user from handling the electrode 1405. Thus, the grasping portion 1407 in various exemplary embodiments may be made of an electrically insulating material.

Two exemplary modes of operation of the system 1400 will now be described with reference to FIGS. 15A-15D and FIGS. 16A-16H. The exemplary embodiments of FIGS. 15A-15D and FIGS. 16A-16H are described with reference to the preparation of a sample for food pathogen detection applications. Those having ordinary skill in the art would understand, however, that such applications are exemplary only and non-limiting, and that the system 1400 could be used in sample preparation and target nucleic acids isolation and collection for various applications. For ease of illustration, FIGS. 15A-15D and 16A-16H are partial cross-sectional views showing only the electrode 1415, cover 1404 and collection chamber 1443, and do not show the power supply and its connections or the base 1431 of the system 1400.

Figures 15A, 15B, 15C, 15D:
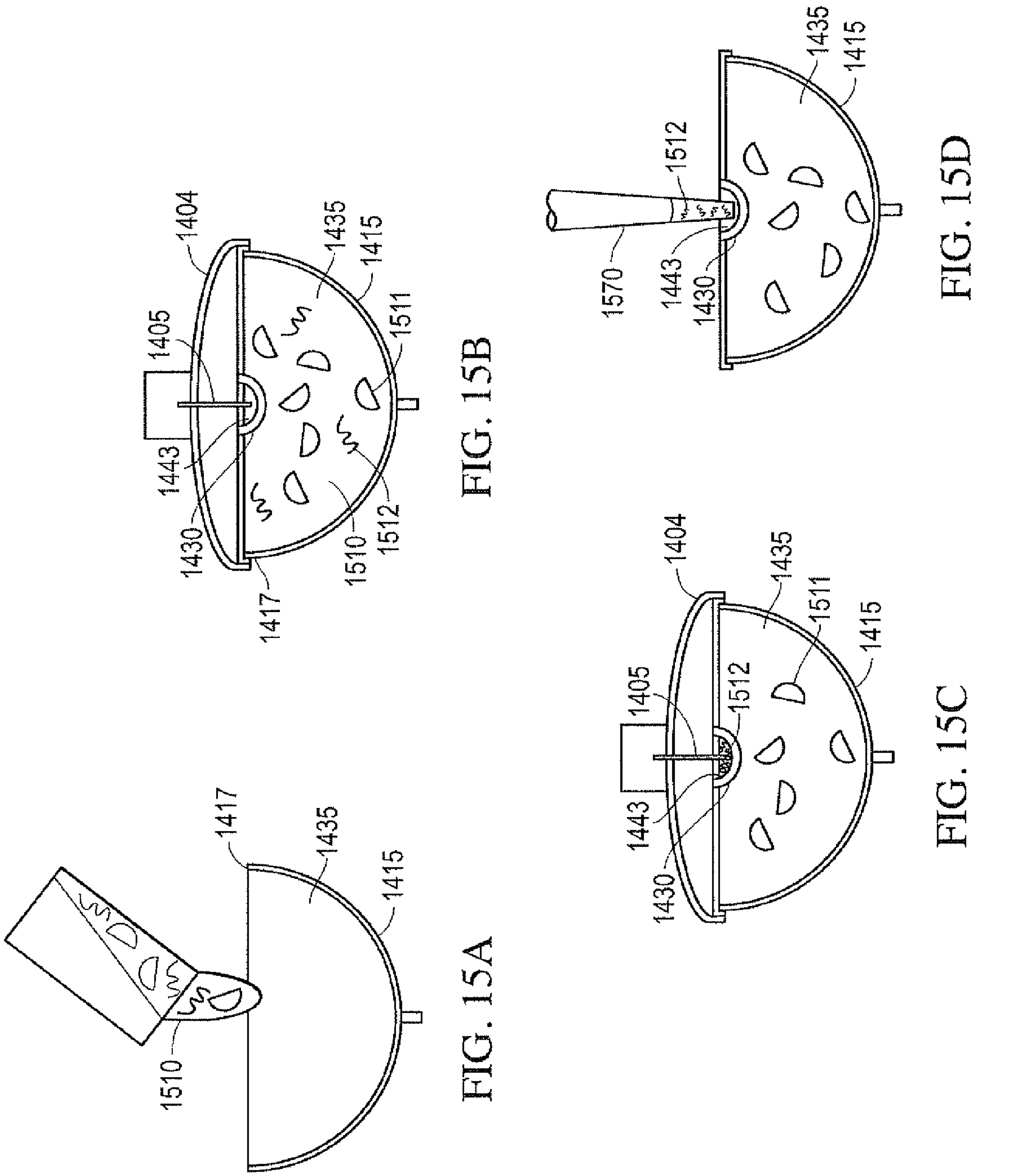
FIGS. 15A-15D show an exemplary embodiment of operating the system of FIGS. 14A and 14B in accordance with the present teachings.

Referring to FIGS. 15A-15D, exemplary steps for using the system 1400 to isolate and collect pathogen nucleic acids from a sample of water that has washed a food product or equipment handling a food product to be tested for pathogens (e.g., meats, vegetables, fruits, pieces of equipment in contact with food products etc.) are illustrated. In FIG. 15A, a sample 1510, such as, for example, water that has washed a food product or equipment that has come into contact with a food product, is supplied to the sample chamber 1435, along with an electrically conductive medium and optionally a lysing reagent (as with other embodiments, the lysing reagent itself may be electrically conductive or an electrically conductive medium may be separately mixed with the lysing reagent). The sample 1510 may be subjected to disruption either before being placed into the sample chamber 1435 or after being placed in the sample chamber 1435. Disruption of entities containing target nucleic acids in the sample may be accomplished by various mechanisms, including chemical, thermal, electrical and/or mechanical mechanisms, as has been discussed above and with which those having skill in the art would be familiar.

After the sample 1510 has been placed in the sample chamber 1435 and disruption has occurred, the contents of the sample chamber 1435 may include a mixture of cell debris 1511, pathogen nucleic acids 1512 (assuming the existence of pathogens in the sample added to the chamber 1435 in FIG. 15A), and other small particles, such as, for example, impurities other than cell debris (not shown in FIG. 15). The cover 1404 may be engaged with the open upper end 1417 of the electrode 1415 to close the sample chamber 1435, with the electrode post 1405 extending into the collection chamber 1443, as shown in FIG. 15B. Power may then be supplied to the electrodes 1405 and 1415 to provide those electrodes with a positive and negative charge, respectively. The electric field generated between the electrodes 1405 and 1415 may act on the electrically conductive sample mixture in the sample chamber 1435 and through the electrically conductive filter material 1430 to cause migration via electrophoresis of negatively charged material contained in the sample chamber 1435.

In the case of the exemplary application of FIGS. 15A-15D, the disrupted sample 1510 may contain negatively charged pathogen nucleic acids 1512 as well as cell debris 1511. Via electrophoresis, the pathogen nucleic acids 1512 may migrate toward the positively charged electrode 1405 that resides in the sample chamber 1443. As they migrate toward the electrode 1405, the pathogen nucleic acids 1512 may encounter the filter material 1430 surrounding the collection chamber 1443. The filter material 1430 may be configured (e.g., have a porosity) to permit passage of the relatively small pathogen nucleic acids 1512, while blocking the passage of larger negatively charged particles, such as, for example cell debris 1511 or other larger negatively charged particles. Electrophoresis may be allowed to continue until the pathogen nucleic acids 1512 have passed through the filter 1430 and into the collection chamber 1443, as show in FIG. 15C.

As shown in FIG. 15D, once the pathogen nucleic acids 1512 have migrated from the sample chamber 1435 and into the collection chamber 1443, the electrodes 1405 and 1415 may be deactivated, the cover 1404 may be removed from the sample chamber 1435, and the isolated pathogen nucleic acids 1512 along with any other substance in the collection chamber 1443, such as an electrolytic buffer medium, may be removed via a removal device 1570. The removal device 1570 may be operated manually or may be automated. Suitable removal devices include, but are not limited to for example, a pipette, a needle, or other removal device The isolated pathogen nucleic acids 1512 can then be subjected to PCR detection and/or other further processing, as desired and in a manner similar to that described above with reference to various exemplary embodiments of the present teachings.

In various exemplary embodiments, portions of the system 1400 may be reusable. For example, the cover 1404 and electrode 1405 may be washed and reused numerous times for processing differing samples. The collection chamber 1443 may be disposed of after each use and a new collection chamber used for each sample preparation process.

Figure 16A:
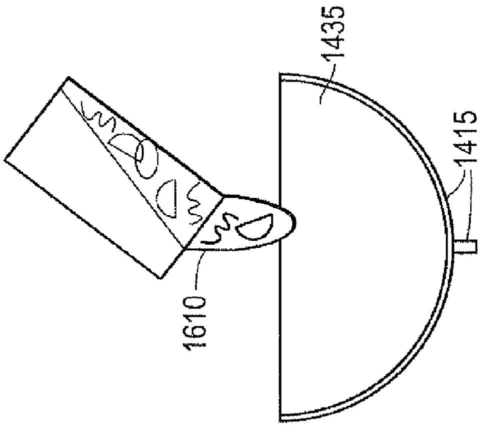
FIGS. 16A-16H show another exemplary embodiment of operating the system of FIGS. 14A and 14B in accordance with the present teachings.
Figure 16B:
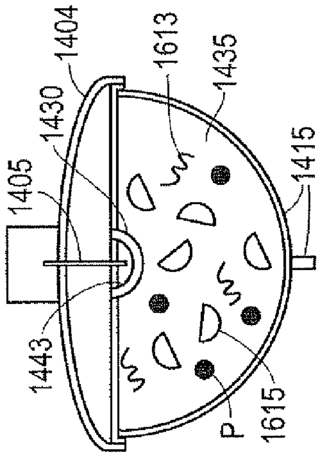

With reference now to FIGS. 16A-16H, exemplary steps for using the system 1400 for pathogen detection in a food product where the sample includes the food product itself are illustrated. For applications in which food pathogen detection is desired and the sample is the food product itself, it may be desirable to perform multiple disruption and electrophoresis steps to first extract and remove the host nucleic acids from the sample and then to extract and remove pathogen nucleic acids. In FIG. 16A, a raw sample 1610 that includes a food product (e.g., which may be stomacked) containing host cells mixed with pathogens is introduced into the sample chamber 1435. The sample 1610 may be subjected to disruption prior to being placed in the sample chamber 1435 or while in the chamber 1435, and disruption may occur via one or a combination of chemical, mechanical, electrical, and thermal mechanisms as described herein and with which those having ordinary skill in the art would be familiar. In any case, the disruption mechanism in FIG. 16A may be selected so as to disrupt the host cells first without disrupting pathogens. In this way, host nucleic acids 1613 may be released and the sample chamber 1435 may contain a mixture of a lysing reagent (if used for disruption), electrically conductive medium, the host nucleic acids 1613, host cell debris 1615, and intact pathogens P. The cover 1404 may be engaged so as to cover the sample chamber 1435, as shown in FIG. 16B.

Figure 16C:
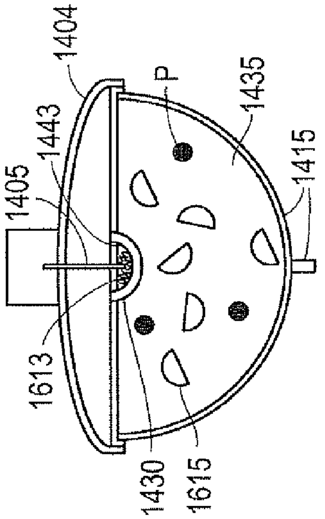
Figure 16D:
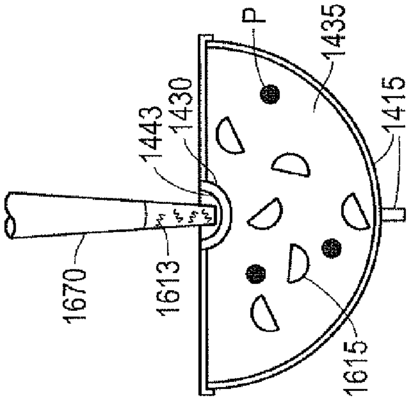

Once the cover 1404 is positioned over the sample chamber 1435, electrophoresis of the host nucleic acids 1613 may be performed by supplying power to negatively charge the electrode 1415 and to positively charge the electrode 1405. Under electrophoresis, the negatively charged host nucleic acids 1613 may migrate toward the electrode 1405 and into the chamber 1443 by passing through the filter material 1430 that is configured to permit passage of particles of the size of the host nucleic acids 1613 while blocking passage of larger negatively charged material, such as, for example, host cell debris 1615 and pathogens P. Electrophoresis may continue until the host nucleic acids 1613 have been removed from the sample chamber 1435 and collected in the collection chamber 1443, as illustrated in FIG. 16C. At this point, as shown in FIG. 16D, the electrodes 1405 and 1415 may be deactivated, the cover 1404 removed and the host nucleic acids 1613 removed, for example via a manual or automated removal device 1670 (e.g., pipette, needle, or other removal device), from the collection chamber 1443. As an alternative to removing the host nucleic acids 1613 with a removal device, the entire collection chamber 1443 with the collected host nucleic acids 1613 may be disposed of.

Figure 16F:
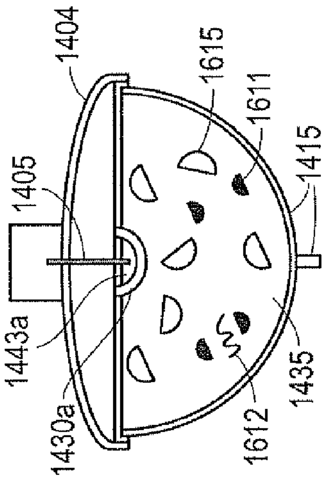
Figure 16H:
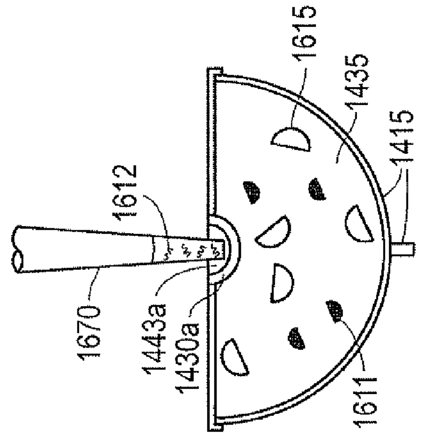
Figure 16E:
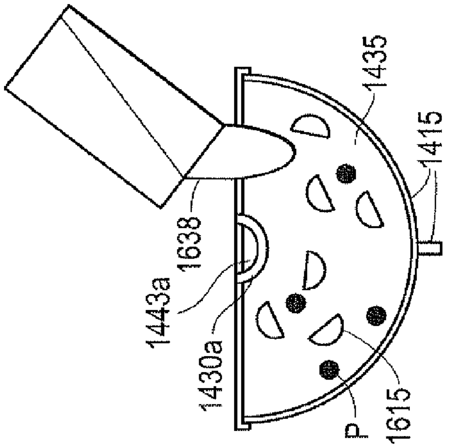

In FIG. 16E, a second disruption step effective to disrupt pathogens P in the sample chamber may be performed. For example, a lysing reagent 1638 effective to lyse pathogens P in the sample chamber 1435 may be added to the contents of the sample chamber 1435 that remain after the step of FIG. 16E. Those having ordinary skill in the art would understand that a variety of disruption techniques as have been described herein may be used in lieu of or in combination with lysing and with each other to achieve disruption of the pathogens. Further, the lysing reagent 1638 effective to lyse pathogens P also may be effective lyse other entities containing nucleic acids, including the host cells, for example. The collection chamber 1443 that collected the host nucleic acids 1613 also may be replaced with a new collection chamber **1443*a* having a new filter material 1430*a***, the latter of which may be configured to exclude differing size material, if necessary.

Figure 16G:
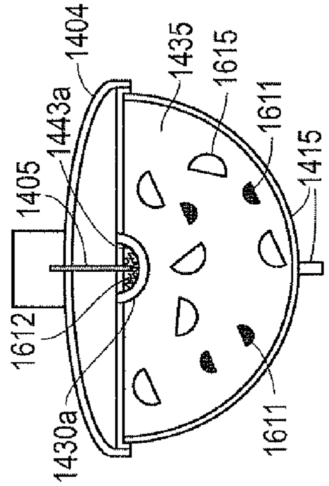

The pathogens P may therefore be subject to disruption in step FIG. 16E, which may occur via one or a combination of chemical, mechanical, electrical, or thermal mechanisms, to release pathogen nucleic acids 1612. Once the pathogens P have been disrupted, the cover 1404 may be placed over the sample chamber 1435, as shown in FIG. 16F, and electrophoresis of the pathogen nucleic acids 1612, as described above with reference to FIG. 16C, may be performed to collect the pathogen nucleic acids 1612 in the collection chamber **1443*a*. The filter material 1430*a* may be configured to permit passage of the pathogen nucleic acids 1612 while blocking passage of host cell debris 1615, pathogen cell debris 1611, and any other negatively charged particles having a size larger than the pathogen nucleic acids 1612 that may be in the sample chamber 1435. After separating the pathogen nucleic acids 1612 in the collection chamber 1443***a*, as shown in FIG. 16G, the electrodes 1405 and 1415 may be deactivated, the cover 1404 removed from the sample chamber 1435, and the collected pathogen nucleic acids 1612 removed from the collection chamber 1443*a* via a manual or automated removal device 1670, as shown in FIG. 16H. The collected pathogen nucleic acids 1612 will thus be in an amount suitable for performing PCR detection and or other analysis assay, and also may be free from substantially all the host nucleic acids contained in the sample 1610 such that little or no contamination of the pathogen nucleic acids 1612 occurs to interfere with PCR detection.

Performing the iterative disruption and collection steps described above with respect to the exemplary embodiment of FIGS. 16A-16H may also be desirable as a way to remove dead pathogens or other dead cells from the sample. PCR detection cannot distinguish nucleic acids released due to cell death from nucleic acids released from live cells due to disruption techniques. During the first round of electrophoresis of the host nucleic acids, nucleic acids that are released due to cell death, including, for example, pathogen nucleic acids from dead cells, will be collected along with the host nucleic acids. In the second round of electrophoresis (e.g., the electrophoresis and collection of the live pathogen nucleic acids), therefore, if any nucleic acids are collected they should be nucleic acids from live pathogens. In some cases, knowing whether or not the second round of electrophoresis collection results in the collection of live pathogen nucleic acids may permit a decision to be made about whether the sample (e.g., food sample) is contaminated with a living pathogen, as opposed to a dead one. In some circumstances if it is determined that the pathogen is dead, it may not be necessary to recall the product.

Although not shown in the exemplary embodiment of FIGS. 14-16, an additional filter that blocks relatively large nucleic acids (e.g., including both host and pathogen nucleic acids) but permits the passage of smaller, negatively charged particles, such as, impurities, may be provided to surround the electrode post 1405 such that electrophoresis separation and removal of those impurities may be achieved in a manner similar to that described above with respect to other exemplary electrophoresis-based systems. Those having skill in the art would understand how to modify the system 1400 to isolate and remove such impurities or other relatively small negatively charged particles using a filter in addition to the filter of the collection chamber 1443.

In the exemplary embodiments of FIGS. 14-16, so that electrophoresis forces can overcome osmotic forces, it may be desirable to provide an electrically conductive gel medium within the sample chamber 1435, such as, for example, an agarose or polyacrylamide gel formed with an electrically conductive medium. In such a case, any disruption step may occur prior to solidification of the gel and then the entire contents of the chamber 1435 may be permitted to solidify prior to performing electrophoresis. In a multiple step disruption procedure, such as, for example, that described with reference to FIGS. 16A-16H, prior to each round of disruption after the initial round, the gel in the sample chamber 1435 may be permitted to liquefy (e.g, via applying heat to the sample chamber 1435). Appropriate disruption procedures, such as, for example, the addition of lysing reagents, may be performed on the liquefied mixture and the mixture permitted to resolidify to a gel before a subsequent round of electrophoresis.

Although titer plates are shown and described above in many exemplary embodiments disclosed with reference to FIGS. 1-13, those having skill in the art would understand that a variety of sample holders could be used without departing from the scope of the present teachings. By way of example only, a plurality of capillary tubes could be configured in an array and replace the individual wells of the titer plates shown.

Figure 17A:
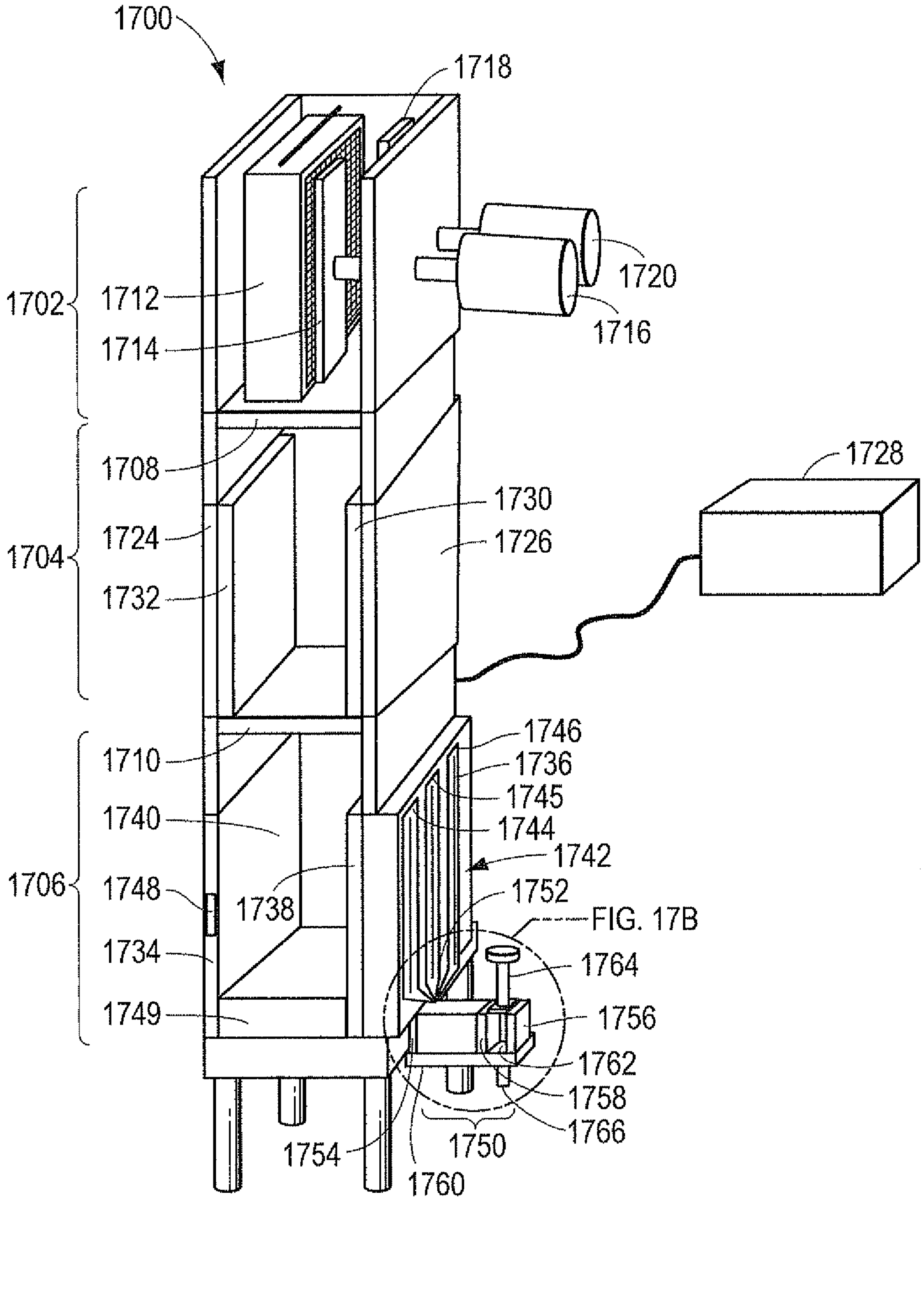
FIG. 17A is a perspective view with some internal features depicted of yet another exemplary embodiment of an electrophoresis-based sample preparation system in accordance with the present teachings.
Figure 17B:
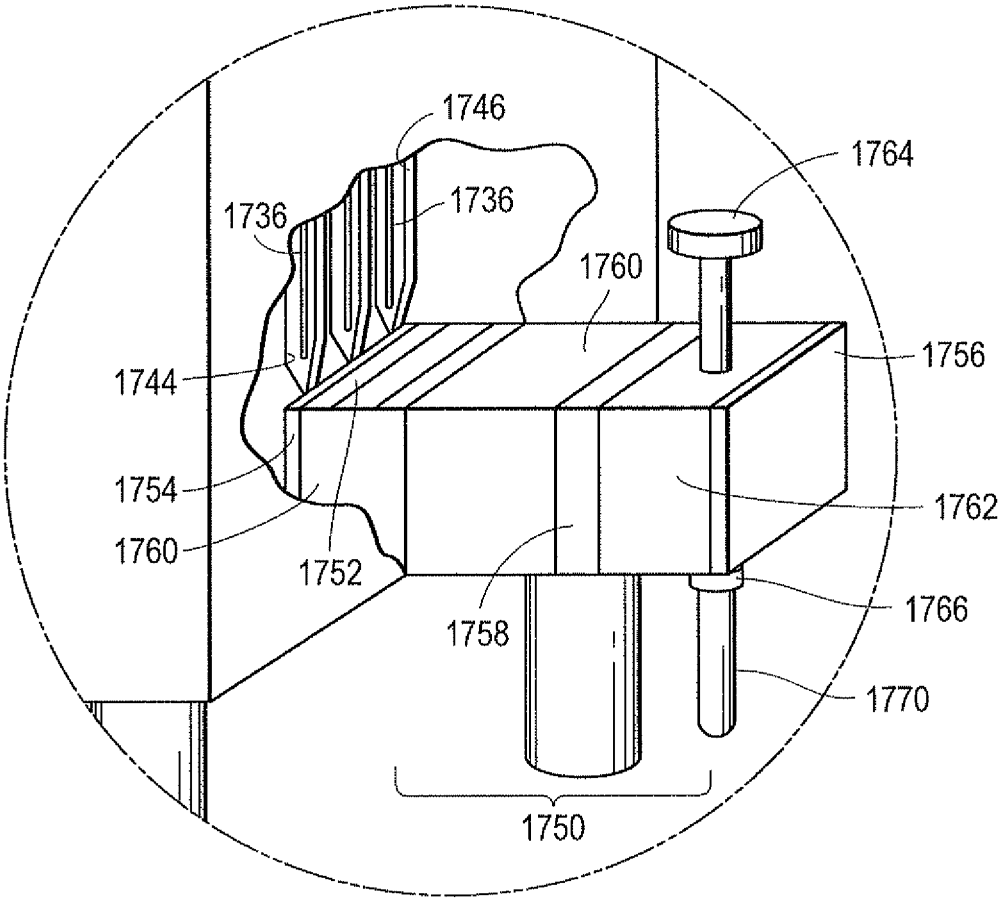
FIG. 17B is an enlarged view of portion 17B of FIG. 17A.

Yet another exemplary embodiment of an electrophoresis-based sample preparation system for extracting, isolating, and collecting nucleic acids from a sample prior to performing further analysis of the nucleic acids, such as, for example, PCR and/or other desired assays, is illustrated in FIGS. 17A and 17B. FIG. 17A is a perspective view of an electrophoresis-based sample preparation system 1700 showing internal portions thereof and FIG. 17B is a perspective view of the portion of system 1700 identified as FIG. 17B in FIG. 17A.

The exemplary embodiment of FIG. 17A shows a multi-chambered electrophoresis-based sample preparation system according to the present teachings. In FIG. 17A, the system 1700 includes a sample chamber 1702, a separation chamber 1704, and a first reduction chamber 1706. The sample chamber 1702 can be in selective fluid communication with the separation chamber 1704. A valve 1708 can provide or prevent a fluid communication between sample chamber 1702 and the separation chamber 1704 when valve 1708 is open or closed respectively. The separation chamber 1704 can further be in selective fluid communication with the first reduction chamber 1706. A valve 1710 can provide or prevent a fluid communication between the separation chamber 1704 and the first reduction chamber 1706 when valve 1710 is open or closed respectively.

In various exemplary embodiments, the valves 1708 and 1710 may include, but are not limited to, for example, a trap door or other hinged doors, a burstable valve, a heat-meltable valve, a dissolvable valve, or other valve mechanisms with which those having ordinary skill in the art have familiarity. The valves 1708 and 1710 may be operated by a motor and can be programmed to open under control of a timing mechanism. Accordingly, the valve 1708 can open to enable contents of the sample chamber 1702 to drop, flow, or otherwise be transferred into the separation chamber 1704, and the valve 1710 can open to enable the contents of the separation chamber 1704 to drop, flow, or otherwise be transferred into the first reduction chamber 1706.

According to the embodiment shown in FIG. 17A, a sealed sample bag 1712 containing a sample is configured to be received within the sample chamber 1702. A first paddle 1714 and a second paddle 1718 can be provided to physically mash, squish, press, and/or otherwise manipulate the sample within the sample bag 1712 if needed. Paddles 1714 and 1718 can be operated by respective motors 1716 and 1720, for example, servo motors, pneumatic pumps, or the like, so that the two paddles alternate manipulating the sample.

As shown in FIG. 17A, the separation chamber 1704 can comprise a first electrode 1724, and a second electrode 1726, both of which may be adapted to be in electrical communication with a controller/power supply 1728. A first filter 1730 can be provided in flow communication with the separation chamber 1704. The first electrode 1724 can comprise a cathode and the second electrode 1726 can comprise an anode. The exemplary embodiment shown in FIG. 17A further comprises an optional filter 1732. The first filter 1730 can be disposed between the first electrode 1724 and the second electrode 1726. The optional filter 1732 can also be disposed between the first electrode 1724 and the second electrode 1726.

In various exemplary embodiments, the separation chamber 1704 may be configured to hold a first volume ranging from about 1 ml to about 200 ml, for example, about 1 ml, about 5 ml, about 20 ml, about 50 ml, or about 200 ml.

According to various exemplary embodiments, and as shown in FIGS. 17A and 17B, the first reduction chamber 1706 can comprise a third electrode 1734, a fourth electrode 1736, and a second filter 1738 disposed between the third electrode 1734 and the fourth electrode 1736. Third and fourth electrodes 1734 and 1736 can be in electrical communication with controller/power supply 1728. In some exemplary embodiments, the fourth electrode 1736 can comprise a wire electrode, for example, platinum, palladium, steel, iron, copper, or the like wire having a diameter ranging from about 0.01 mm to about 5 mm.

According to various exemplary embodiments, the first reduction chamber 1706 may include a disruption chamber 1740 between the third electrode 1734 and second filter 1738 and disposed on a first side of second filter 1738. The first reduction chamber 1706 can further comprise a first collection chamber 1742 disposed on a side of the second filter 1738 that is opposite the first side. According to various exemplary embodiments, the fourth electrode 1736 can be disposed in, or form an inner surface of, the first collection chamber 1742. In some exemplary embodiments, the third electrode 1734 can comprise a cathode and the fourth electrode 1736 can comprise an anode. The third electrode 1734 can be capable of electrical communication with the fourth electrode 1736 when a sample is disposed within the first reduction chamber 1706.

The first collection chamber 1742 can comprise one or more connected channels, shown in FIGS. 17A and 17B as channels 1744, 1745, and 1746. The disruption chamber 1740 can be configured to retain a second volume and the first collection chamber 1742 can be configured to retain a third volume; the third volume can be less than the second volume. By way of example only, the volume of the sample collected in first collection chamber 1742 may be ten times less, one hundred times less, or one thousand times less than the volume of the sample received in the disruption chamber 1740. The ratios of the volumes of the received sample may depend on various factors, including, for example, the size of the disruption chamber 1740, the size of the first collection chamber 1742, and the respective volumes of liquid in those two chambers.

According to various exemplary embodiments, the first reduction chamber 1706 can further comprise a heater (not shown) and a heat sensor 1748. In some embodiments, the third electrode 1734 can comprise the heater. Alternatively or in addition to the third electrode 1734 comprising the heater, heat can be applied via various heating elements including, but not limited to, convective heating elements, conductive heating elements, radiant heating elements, and/or other heating mechanisms, and/or combinations thereof. According to various exemplary embodiments, a lysing buffer 1749 can be disposed within the disruption chamber 1740.

According to various exemplary embodiments, the system 1700 shown in FIGS. 17A and 17B can comprise a second reduction chamber 1750 in selective fluid communication with first collection chamber 1742, with a valve 1752 disposed between first collection chamber 1742 and second reduction chamber 1750 providing or preventing fluid communication therebetween. In various exemplary embodiments, the valve 1752 may comprise a valve chosen from, for example, a one-way valve, a duckbill check valve, a motorized trap door valve, and/or another suitable valve mechanisms with which those ordinarily skilled in the art would be familiar.

The second reduction chamber 1750 can comprise a fifth electrode 1754, a sixth electrode 1756, and a third filter 1758 disposed between fifth electrode 1754 and sixth electrode 1756. Fifth electrode 1754 can comprise a cathode and sixth electrode 1756 can comprise and an anode, and the electrodes can be in electrical communication with controller/power supply 1728.

The second reduction chamber 1750 can comprise a receiving chamber 1760 disposed between the fifth electrode 1754 and the third filter 1758 and on a first side of the third filter 1758. The second reduction chamber 1750 can further comprise a second collection chamber 1762 disposed on a side of the third filter 1758 that is opposite the first side. According to various embodiments, sixth electrode 1756 can be disposed in, or form an inner surface of, second collection chamber 1762. The fifth electrode 1754 can be capable of electrical communication with sixth electrode 1756 when a sample is disposed within second reduction chamber 1750.

The receiving chamber 1760 can be configured to retain a fourth volume and second collection chamber 1762 can be configured to retain a fifth volume; the fifth volume can be less than the fourth volume. By way of example only, the volume of the sample collected in second collection chamber 1762 may be ten times less, one hundred times less, or one thousand times less than the volume of the sample received in the receiving chamber 1760. The ratios of the volumes of the received sample may depend on various factors, including, for example, the receiving chamber 1760, the size of the second collection chamber 1762, and the respective volumes of liquid in those two chambers.

As shown in FIGS. 17A and 17B, the electrophoresis-based sample preparation system 1700 can further comprise a plunger 1764 and a valve 1766. Plunger 1764 can be adapted such that it can dispense a volume of fluid from second collection chamber 1762 through valve 1766 and into a collection vessel 1770, for example, a tube or well (e.g., a well of a microtiter plate).

With reference now to FIGS. 18-26, according to various exemplary embodiments, the electrophoresis-based sample preparation system of FIGS. 17A and 17B may be used for isolating pathogen nucleic acids from a sample, such as, for example, a sample containing host cells and pathogens. FIGS. 18-26 illustrate various exemplary steps for using the system 1700 to perform such a method.

Figure 18:
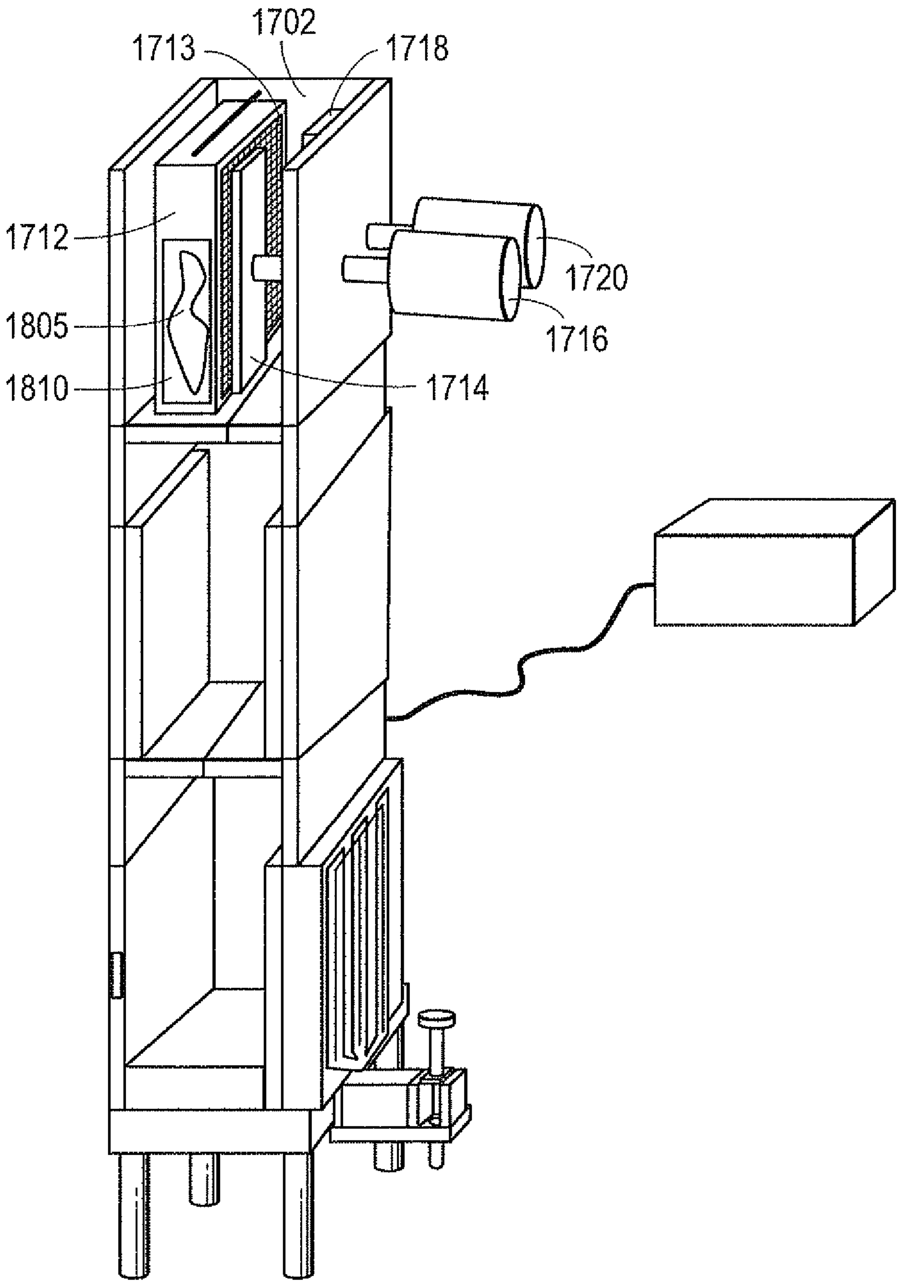
FIGS. 18-26 show exemplary steps for operating the system of FIGS. 17A and 17B in accordance with the present teachings.

In FIG. 18, a first exemplary step of a method according to an embodiment of the present teachings is depicted. According to various embodiments, and as shown, a bag 1712 may be disposed within the sample chamber 1702 and can contain a foodstuff sample 1805 and a first lysis buffer 1810. Lysis buffer 1810 can comprise, for example, citric acid, SDS (sodium dodecyl sulfate), and TE buffer, or any other buffers described herein, in concentrations sufficient to together lyse host cells without lysing pathogens. One or more paddles 1714 and 1718 may be controlled by the one or more motors 1716 and 1720, respectively. The paddles 1714 and 1718 may be operated to push on bag 1712, thus manipulating, lysing and liquefying foodstuff sample 1805 into a matrix material, comprising, for example, intracellular nucleic acid, proteins, and pathogens. The mechanical paddling action in combination with the first lysis buffer 1810 can disrupt (e.g., including lysing) the host cells, connective tissue, and other solid matter within the foodstuff sample 1805, without causing disruption of pathogens.

As paddles 1714 and 1718 push on bag 1712, most of the matrix material can leak out of the bag 1712, for example, through a filter 1713 (which may be formed as part of the bag 1712), and into the sample chamber 1702. The filter 1713 can comprise holes having an average minimum cross-sectional opening that is large enough to allow the intracellular materials and any pathogens to travel through filter 1713, while trapping the larger and less soluble cell and tissue material. For example, the filter 1713 can comprise holes of an average cross-section of about 0.1 mm in diameter, although other diameters can be provided. Other exemplary filter hole cross-section diameters can range from about 0.001 mm to about 1.0 mm, for example from about 0.01 mm to about 0.5 mm.

Figure 19:
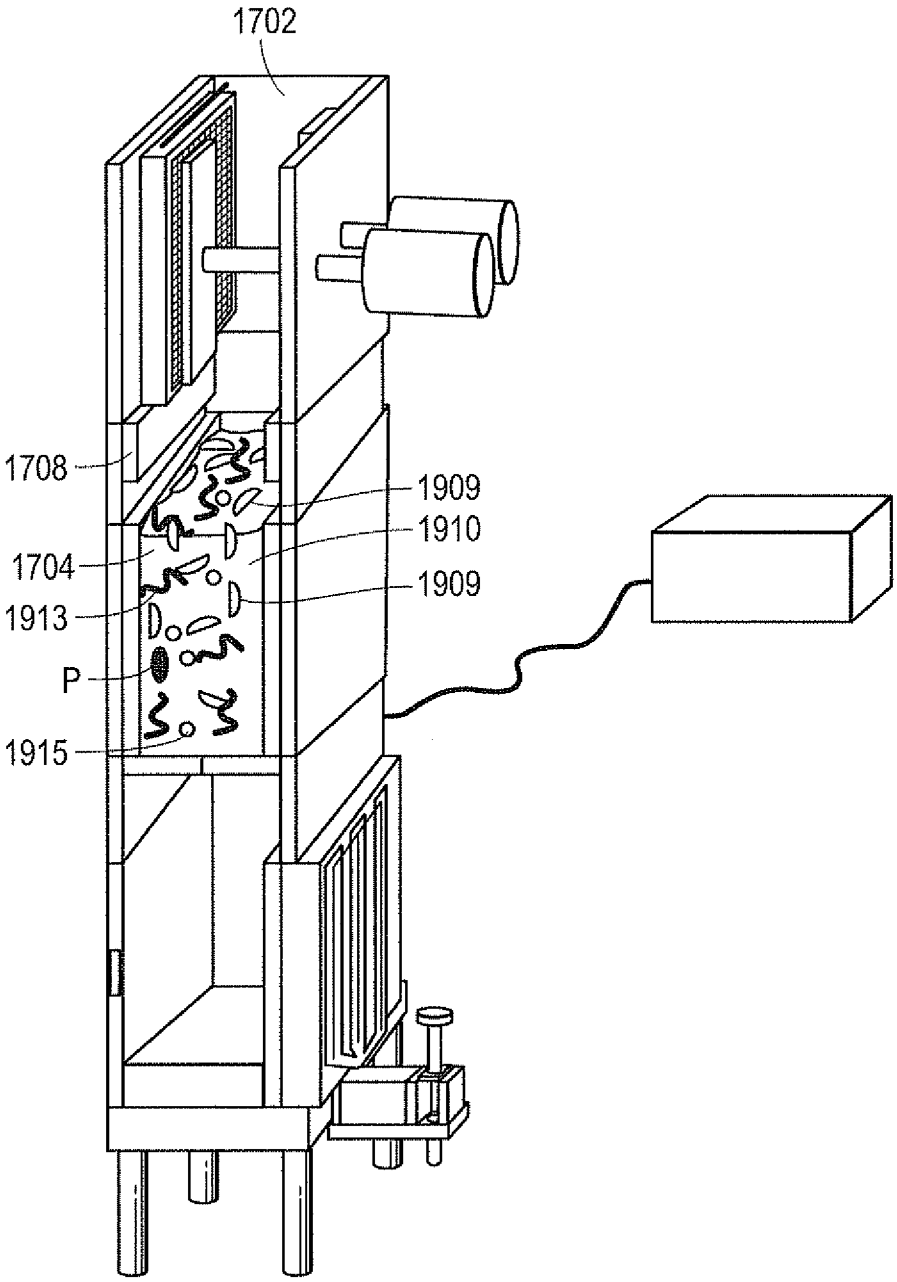

As shown in FIG. 19, a first valve 1708, disposed between the sample chamber 1702 and the separation chamber 1704, can be opened to allow transfer of the matrix material 1910 from the sample chamber 1702 into the separation chamber 1704. Alternatively, an undigested foodstuff sample can be transferred into the separation chamber 1704 where digestion may occur before removal of the host cell material. The first valve 1708 can be operated by a motor (not shown), such as, for example, a pneumatic motor or a servo motor. Matrix material 1910 can comprise host cell nucleic acid 1913, lysed host cell membranes 1909, other proteins and assorted impurity material 1915, and one or more pathogens P.

Figure 20:
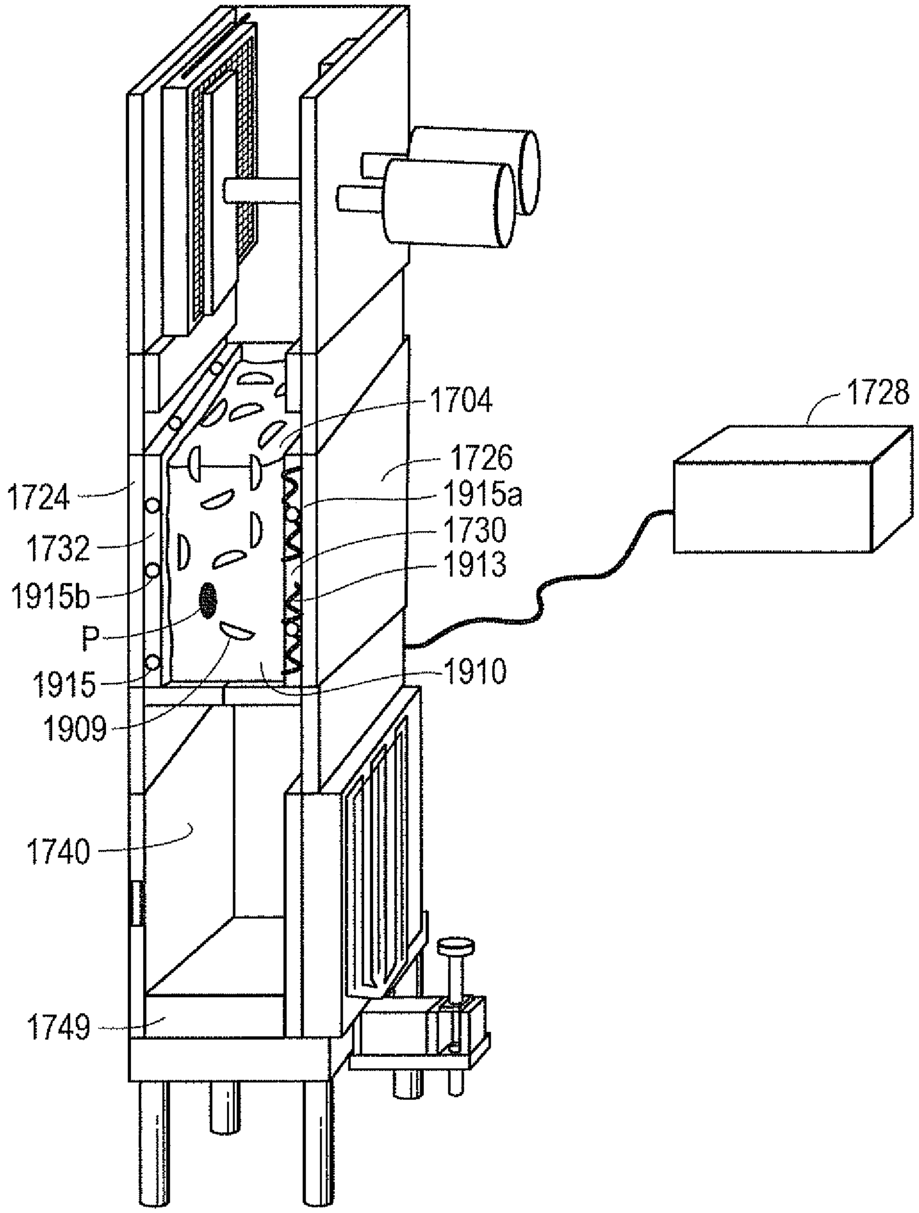

As shown in FIG. 20, the power supply 1728 supply power to the electrodes 1724 and 1726 such that an electric field can be formed between the two electrodes 1724 and 1726 and electrophoresis may occur that attracts negatively-charged particles including the released host cell nucleic acids 1913 and some negatively-charged proteins and/or other impurity material 1915*a* into filter 1730, and positively-charged particles, including positively charged proteins and/or other impurity material 1915*b* into filter 1732. The host cell nucleic acids 1913, and any nucleic acids from dead pathogens, can thus be separated and removed from the sample material matrix 1910. The one or more undisrupted and uncharged pathogens P, the disrupted host cell membrane material 1909, and other uncharged impurity material and/or proteins (not shown) may remain in the resultant processed sample and in separation chamber 1704.

A volume of pathogen lysis buffer 1749 can be predeposited in the disruption chamber 1740. In various exemplary embodiments, the pathogen lysis buffer 1749 can comprise, for example, NaOH (sodium hydroxide), SDS, or a combination thereof in concentrations sufficient so that they together enable the disruption (e.g., lysing) of the one or more pathogens P, either at room temperature, or, if desired, at an elevated temperature. In various exemplary embodiments, the pathogen lysis buffer 1749 may be sufficient to also achieve disruption of the host cells.

Figure 21:
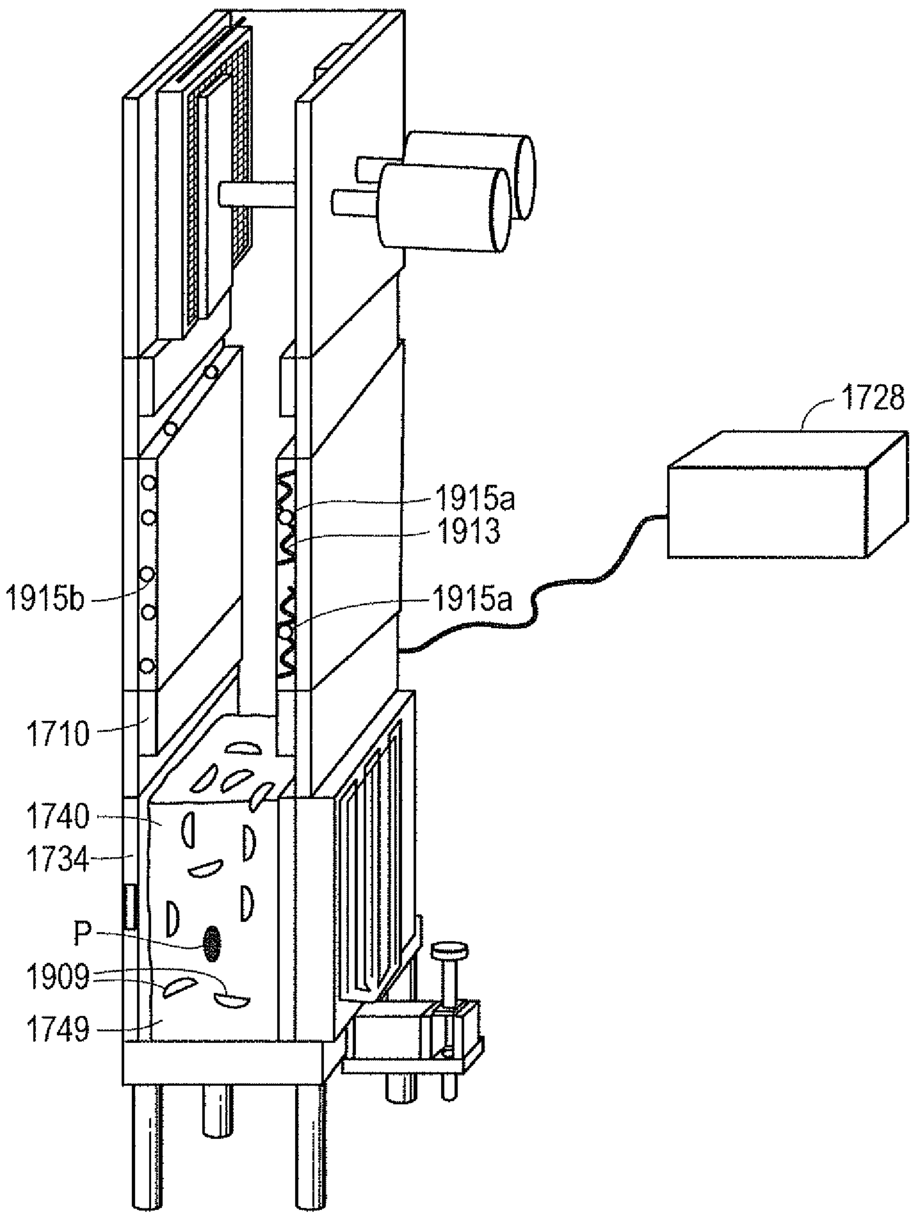

As shown in FIG. 21, the second valve 1710 can be opened to enable the processed sample to drop, flow, or otherwise be transferred from the separation chamber 1704 to the disruption chamber 1740. The disruption chamber 1740 can comprise at least one electrode 1734. As discussed above, according to various exemplary embodiments, the disruption chamber 1740 can further comprise a heater (shown in FIG. 22) and in some exemplary embodiments, the electrode 1734 can function as both an electrode and as a heater.

Upon transfer of the processed sample into the disruption chamber 1740, the disruption chamber 1740 may contain a mixture of the pathogen lysis buffer 1749 and the processed sample comprising undisrupted pathogens P and uncharged cellular materials, such as, for example, uncharged proteins or other impurity material (not shown) and/or uncharged host cell membrane material 1909.

Figure 22:
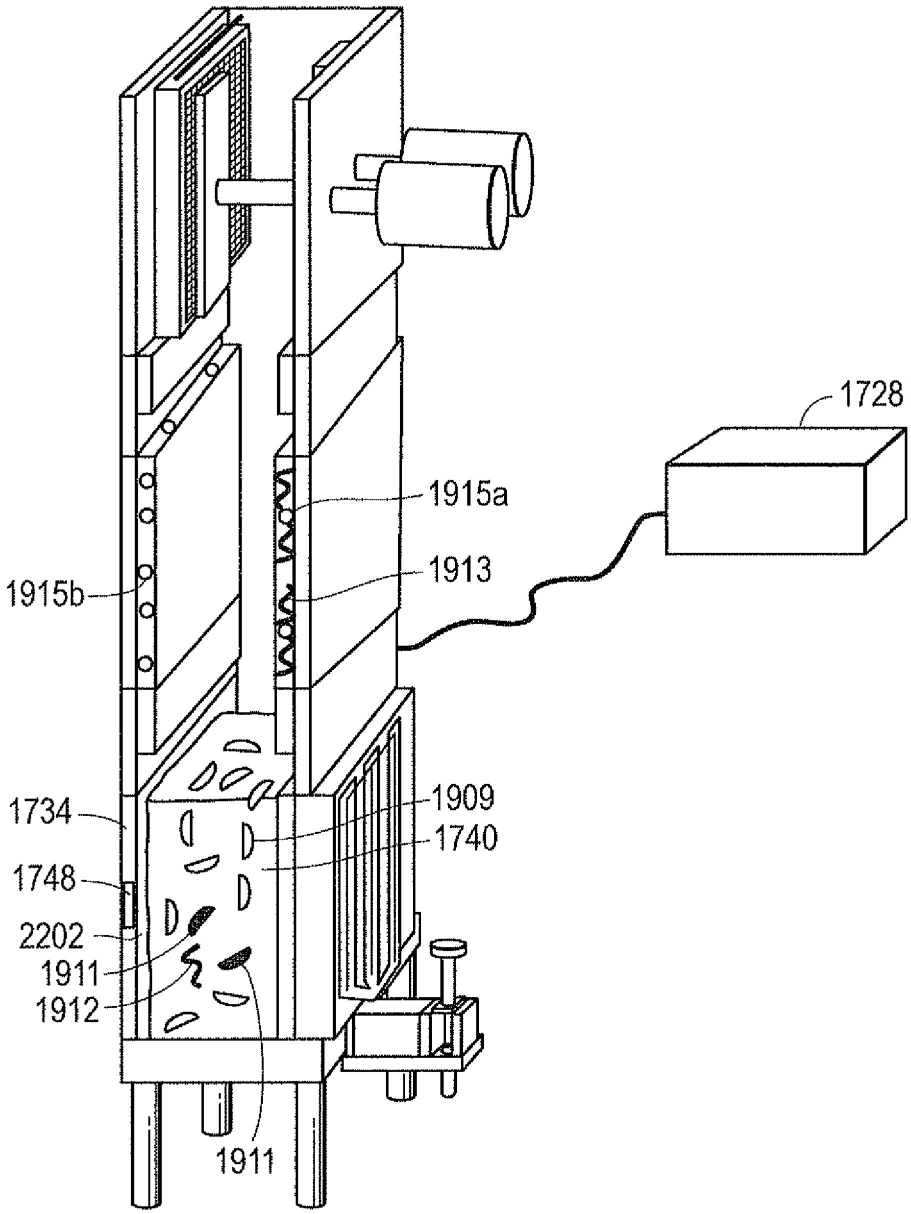

As shown in FIG. 22, pathogen lysis buffer, optionally in combination with heat applied from a heating element, which can be a separate element 2202 or electrode 1734, can disrupt the one or more pathogens P (illustrated as two halves 1911), releasing pathogen nucleic acid 1912. A heat sensor 1748 can be used to monitor the temperature of the pathogen disruption (lysis) reaction and a signal generated from heat sensor 1748 can be sent to a heating system, for example, a heating system that comprises a power source and a controller. After disruption of the one or more pathogens P in disruption chamber 1740, therefore, the disruption chamber 1740 may contain the host cell membrane material 1909, the pathogen boundary (e.g., cell membrane, capsid, viral envelope, and/or other disrupted boundary material) 1911, and pathogen nucleic acid 1912.

Figure 23:
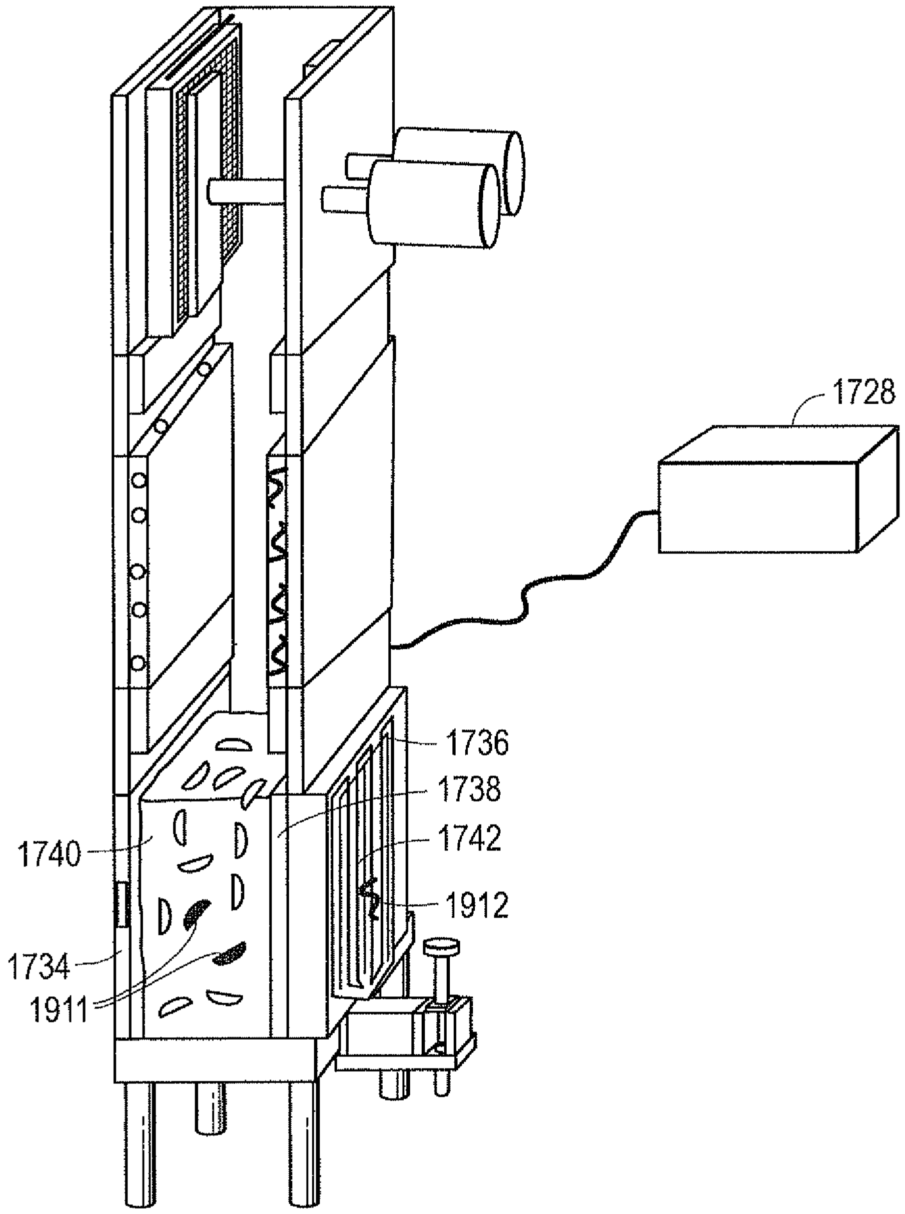

As shown in FIG. 23, the electrodes 1734 and 1736, which may be a cathode and anode, respectively, may be powered via the unit 1728 to establish an electric field therebetween across a conductive material, such as, for example, a conductive buffer, in the disruption chamber 1740. The electric field applied between the electrode 1734 and electrode 1736 can be sufficient to cause the electrophoretic migration of the pathogen nucleic acid 1912 from the disruption chamber 1740 through filter 1738 and toward electrode 1736.

Figure 24:
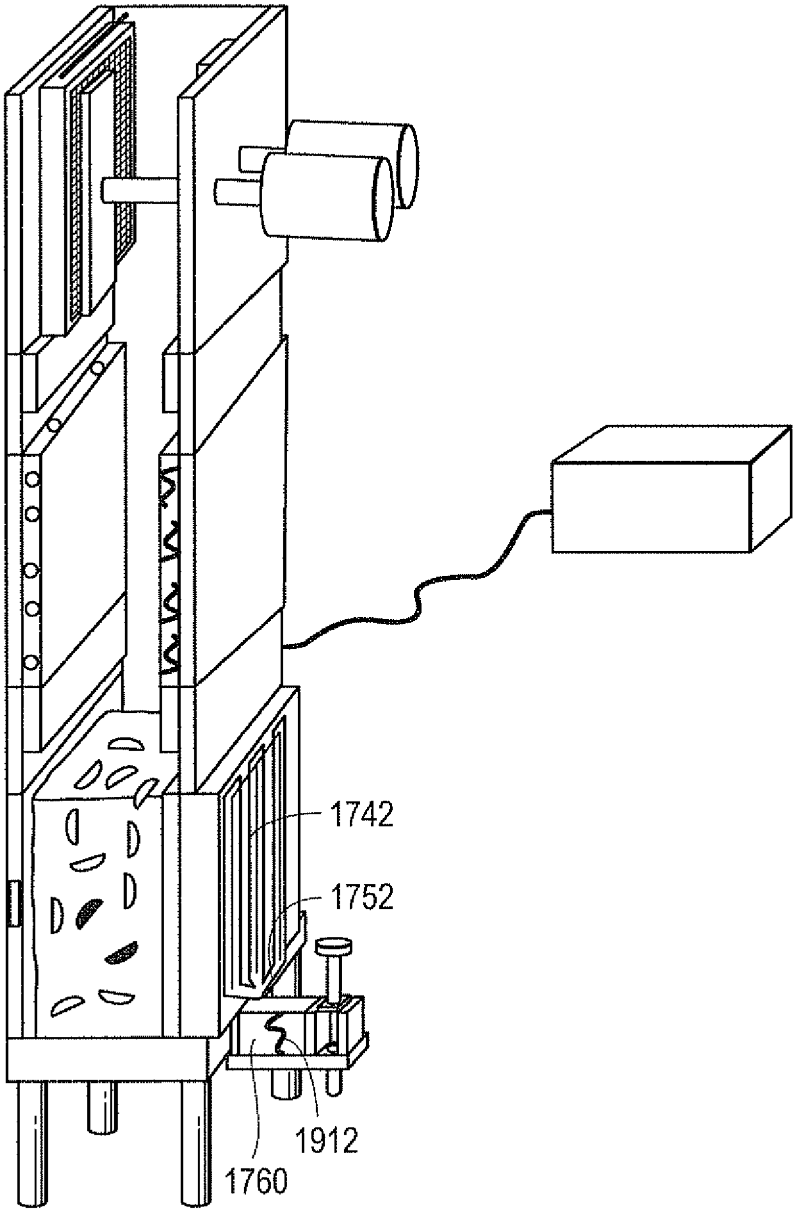

As shown by the embodiment in FIG. 24, the first collection chamber 1742 can be configured to contain a volume that is less than the volume contained by disruption chamber 1740. As shown in FIG. 24, electrophoresis draws the pathogen nucleic acid 1912 from the disruption chamber 1740, through the filter 1738, and into the first collection chamber 1742, which may contain a buffer medium, such as, for example, TBE. In some embodiments, the filter 1738 can comprise holes of a size that allow pathogen nucleic acid 1912 to pass through filter 1738, while excluding larger particulate matter, such as for example, the pathogen boundary material 1911 (e.g., cell membrane, capsid, viral envelope, and/or other disrupted boundary material), host cell membrane material 1909, etc.

As shown in FIG. 24, the receiving chamber 1760 can be in flow communication with the first collection chamber 1742, and the flow communication can be achieved via opening a valve 1752 disposed between the receiving chamber 1760 and the first collection chamber 1742. The valve 1752 can be configured to open to enable the pathogen nucleic acid 1912 to flow or otherwise be transferred into receiving chamber 1760.

Figure 25:
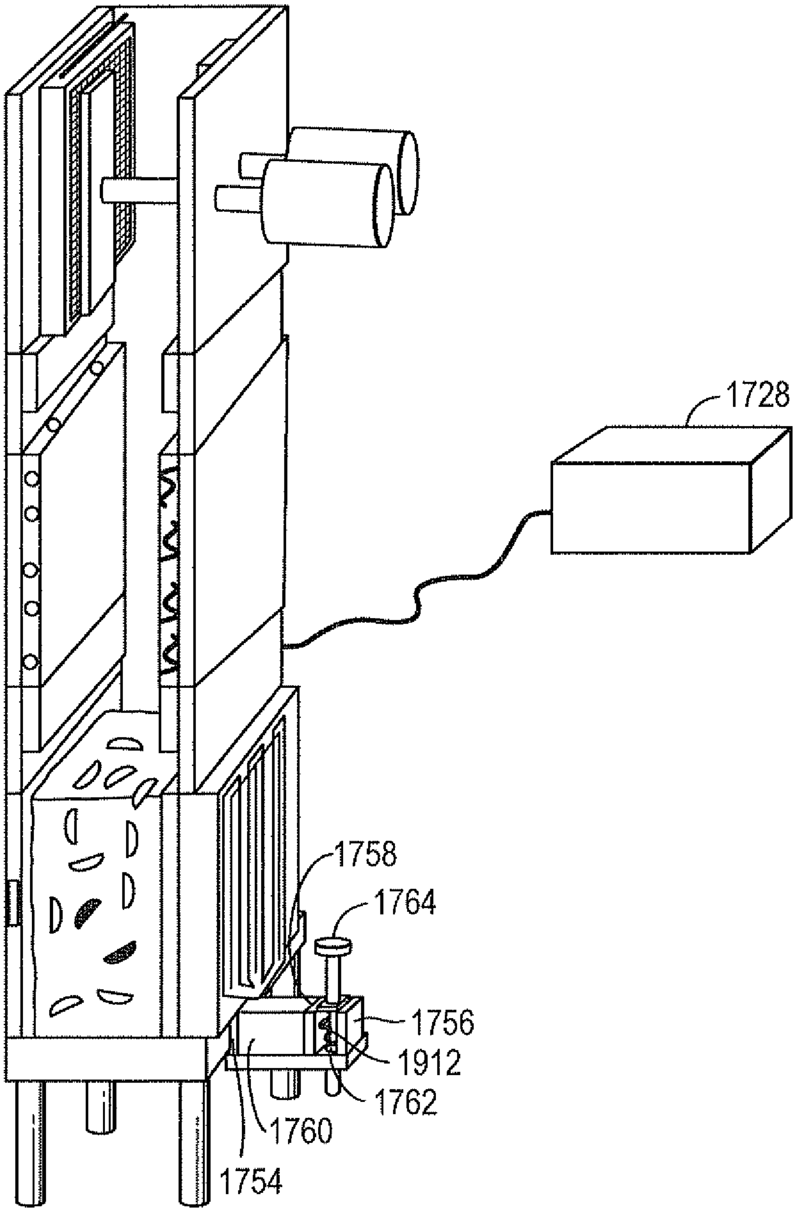

As shown in FIG. 25, the electrode 1754 of receiving chamber 1760 may be in electrical communication with power supply and control unit 1728 and with electrode 1756. As shown in FIG. 25, power supply and control unit 1728 power the electrodes 1754 and electrode 1756 to generate an electric field therebetween, thereby causing migration via electrophoresis of the pathogen nucleic acid 1912 from receiving chamber 1760, through filter 1758, and into the second collection chamber 1762. The second collection chamber 1762 can be configured to contain a volume that is less than the volume contained within the receiving chamber 1760. The second collection chamber 1762 also may contain an electrically conductive buffer medium, such as, for example, TBE.

Figure 26:
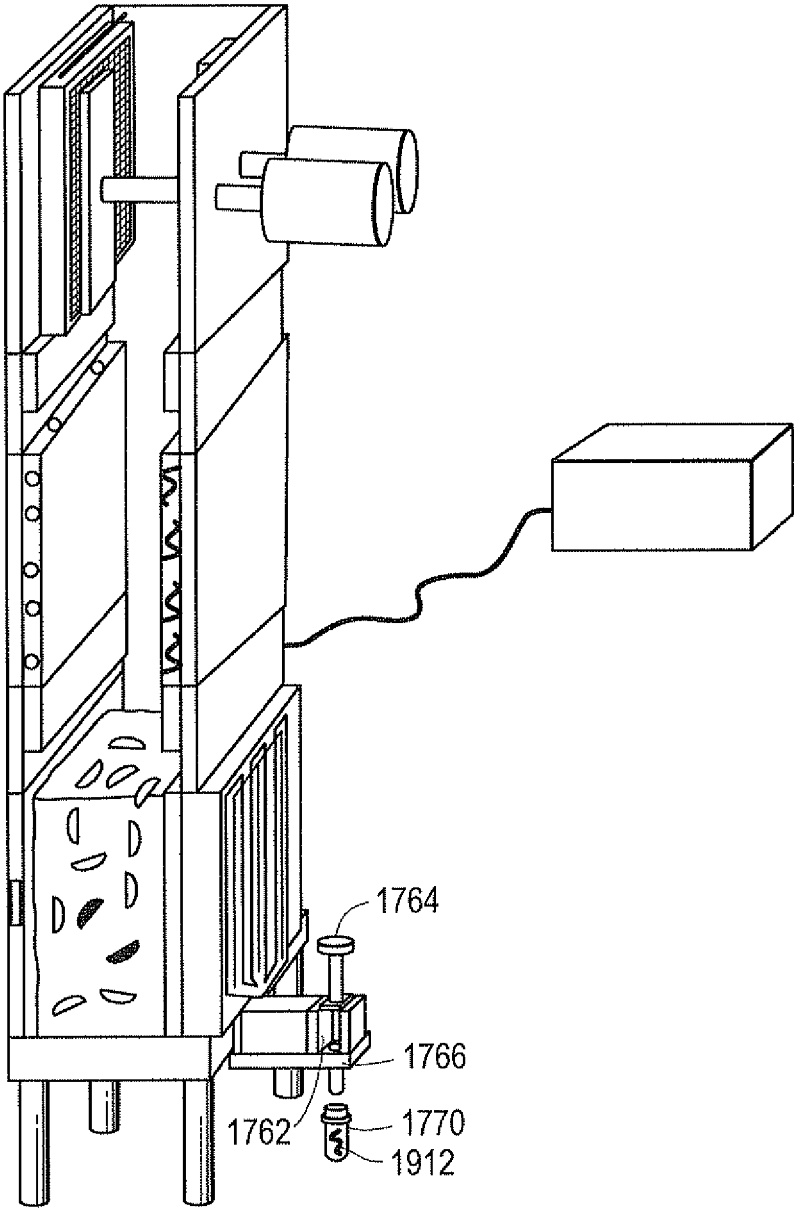

As shown in FIG. 25 and in FIG. 26, the second collection chamber 1762 can further comprise a plunger 1764. Plunger 1764 can push the contents of second collection chamber 1762, including pathogen nucleic acid 1912, through a valve 1766 and into a collection vessel 1770. Pathogen nucleic acid 1912 can now efficiently be further processed and/or subjected to analysis, such as, for example, by polymerase chain reaction.

According to various exemplary embodiments, it is contemplated that a disposable bag may be utilized in conjunction with a multi-chambered electrophoresis-based system, like the system 1700 described above with reference to the exemplary embodiment of FIGS. 17-26. Such a disposable bag configured to be inserted into the system may eliminate the need for washing the various chambers of the system and/or substantially prevent cross-contamination between samples. FIGS. 27A-27D show the components of such an exemplary bag.

Figure 27B:
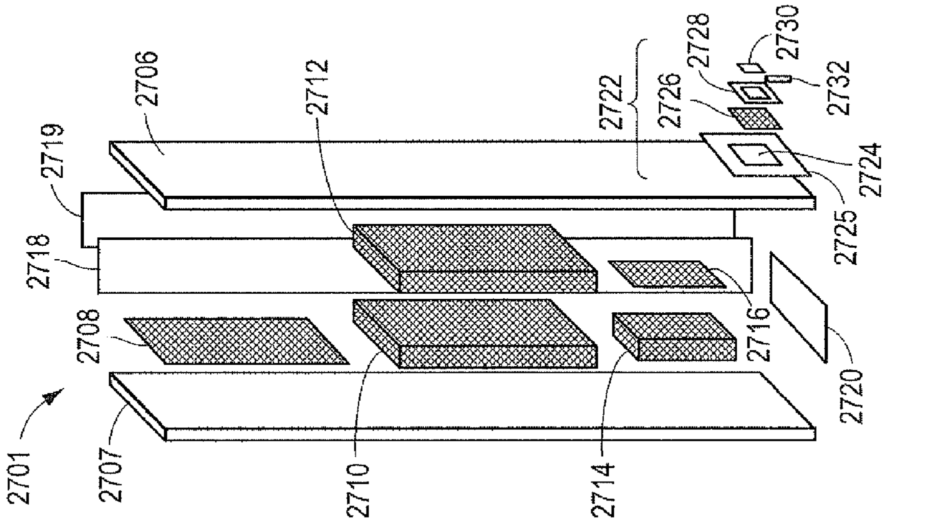
FIG. 27B is an exploded view of the exemplary embodiment of the bag of FIG. 27A and its components.
Figure 27A:
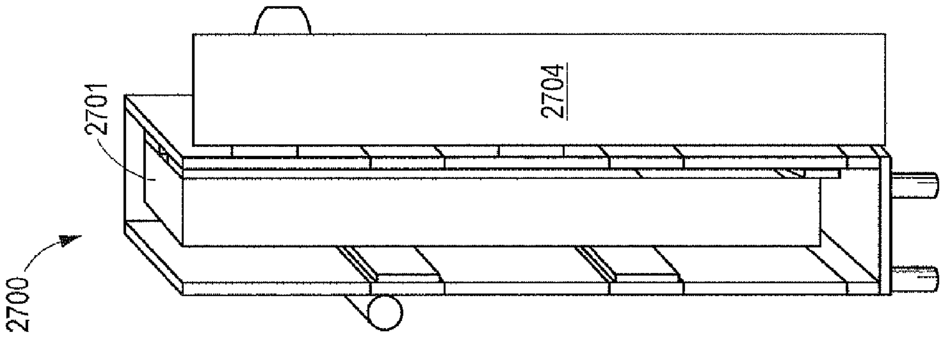
FIG. 27A is a perspective view of an exemplary embodiment of another electrophoresis-based sample preparation system which utilizes a bag in accordance with the present teachings.

FIG. 27A shows an exemplary embodiment of a bag 2701 inserted into an electrophoresis-based sample preparation system 2700. The electrophoresis-based system 2700 may include a door 2704 to facilitate access to the bag 2701.

FIG. 27B shows an exploded, isometric view of bag 2701 and its components. The bag 2701 may include opposing sides 2706 and 2707 that may comprise electrically conductive material. The electrically conductive material can comprise, for example, aluminum, aluminum foil, copper, copper foil, carbonized plastic that is commonly used in the electronics industry, or the like. The bag 2701 can comprise several filters, for example, disposed in an interior of the bag 2701. The filters can comprise be configured to as size-exclusion filters and as such may comprise a size-exclusion material, including, for example, a porous material, a gel material, and/or an electrophoresis separation medium, a combination thereof, or the like. The filters can comprise a submillimeter filter 2708 having relatively large holes, for example, comprising an average minimum cross-sectional opening of greater than 1 micron, but less than 1.0 millimeter, for example, of about 0.1 millimeter. The filters can comprise submicron filters 2710, 2712, 2714, 2716, and 2726 having smaller holes, for example, comprising average minimum cross-sectional openings of less than 1.0 micron. As can be seen in FIGS. 27A-27D, the filters can have different sizes, shapes, and thicknesses, and in some embodiments, can be rectanguloid. The sides 2718 and 2719, the bottom 2720, and the top (shown as 2740 in FIG. 27D) of the bag 2701 can comprise non-electrically conductive material. The non-electrically conductive material can comprise, for example, a plastic, such as, for example, polyethylene or polypropylene. The bag 2701 can comprise opposing faces 2706 and 2707, sides 2718 and 2719, bottom 2720, and top 2740, joined together, for example, with adhesive or by melt bonding, to form fluid-tight seals at each joined edge.

Figure 27D:
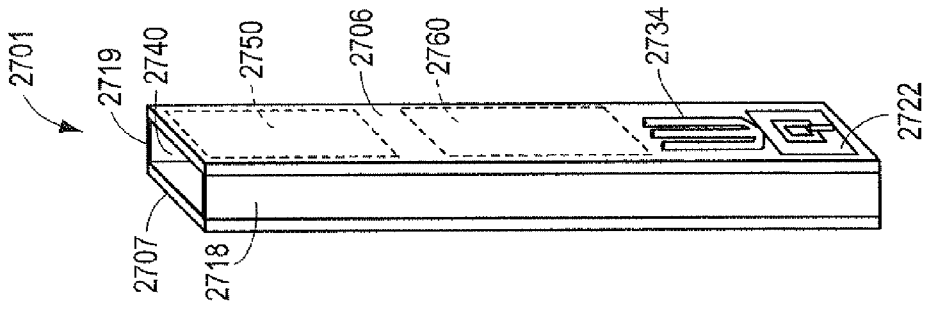
FIG. 27D is a perspective view of the bag and its components of FIG. 27A in an assembled form.
Figure 27C:
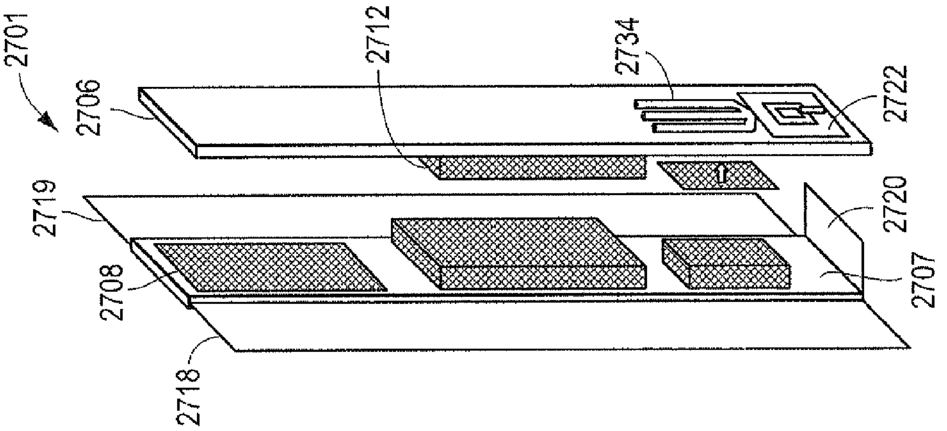
FIG. 27C is a partially exploded and partially assembled view of the bag and its components of FIG. 27A.

FIG. 27C shows a partial assembly of the components of bag 2701. FIG. 27C shows opposing faces 2706 and 2707 of electrically conductive material submillimeter filter 2708, submicron filters 2710, 2712, 2714, 2716, and 2726, non-electrically conductive sides 2718 and 2719, and bottom 2720. A collection chamber 2734 and a bellows chamber 2722 can be formed upon completion of the bag 2701 by providing burstable blister seals between the various regions of the components of the bag 2701 at the time of joining together the various faces, sides, top, and bottom of bag 2701.

The resultant assembled bag 2701 defines the various functional chambers and filters shown and described above in connection with the exemplary embodiment of the electrophoresis-based sample preparation system 1700 shown and described above with reference to FIGS. 17-26, with at least the exception of burstable blister seals being provided in place of various valves described with reference to the exemplary embodiment of those figures. In some exemplary embodiments, housing 2702 can be provided with mechanical squeezing devices, such as motor-driven pressure plates (not shown), to squeeze the various chambers of the bag 2701 and cause sequential bursting of the blister seals that separate the individual chambers. The individual chambers, as shown in FIG. 27D, can comprise a sample chamber 2750, similar to the sample chamber 1702 described with reference to FIGS. 17-26, and a separation chamber 2760, similar to the separation chamber 1704 described with reference to FIGS. 17-26. Similarly, first and second reduction chambers can also be provided. The bellows chamber 2722 is shown in more detail in FIG. 27B and in FIGS. 28A-28D.

With reference to FIG. 27B, the bellows chamber 2722 can comprise an electrode 2724, an electrode frame 2725, a filter 2726, a filter frame 2728, and an electrode 2730. Bellows chamber 2722 can further comprise a valve 2732. Further details regarding the bellows chamber 2722 are provided with reference to FIGS. 28A-28D and the description that follows.

Figures 28A, 28B, 28C, 28D:
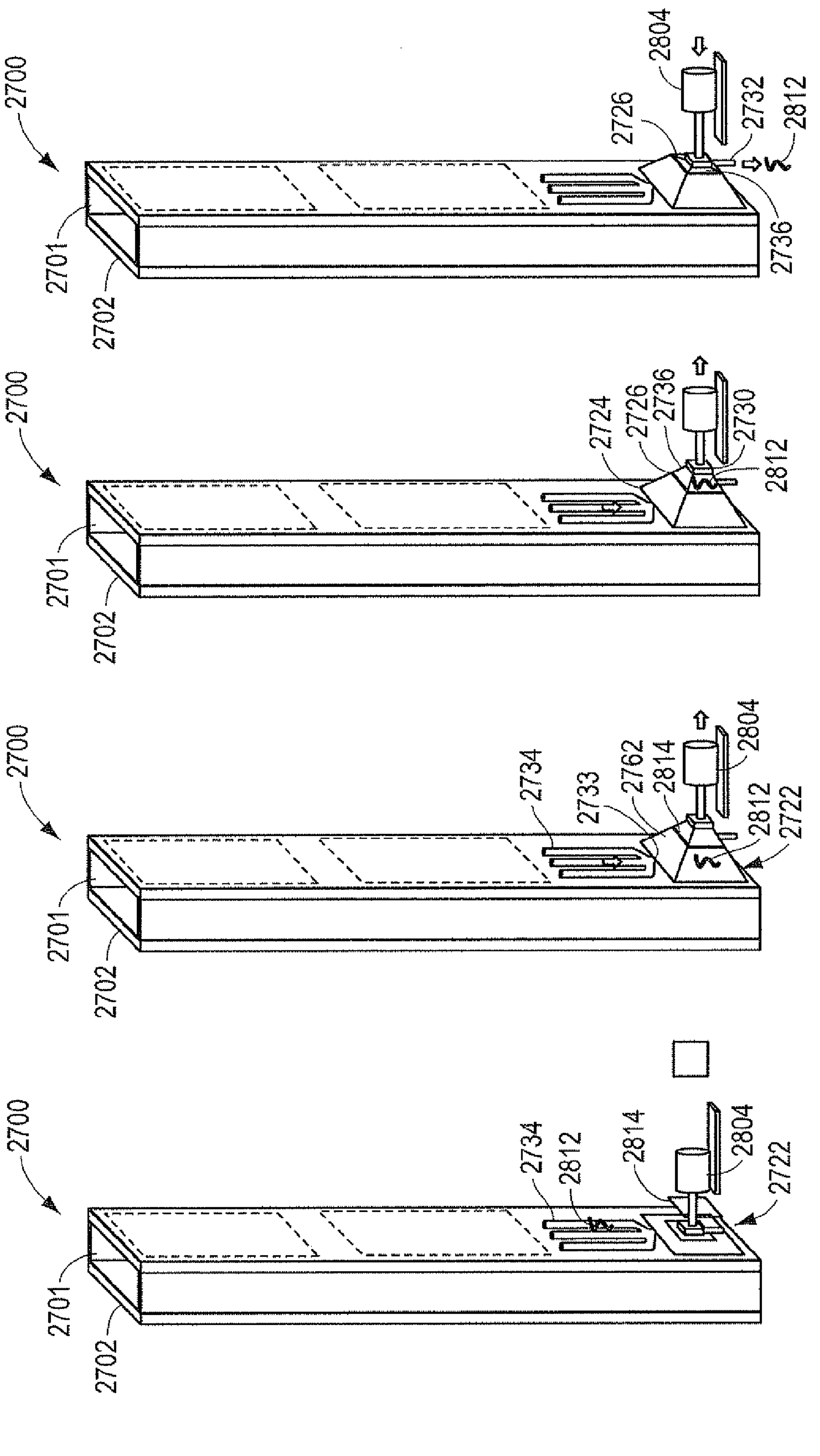
FIGS. 28A-28D show exemplary steps of the operation an electrophoresis-based sample preparation system utilizing a bag according to the present teachings.

As shown in the exemplary embodiment of FIGS. 28A-28D, the bag 2701 can comprise a bellows chamber 2722 that can be operated by a bellows actuator 2804. As illustrated, bellows actuator 2804 can comprise a linear slide and motor combination. According to various exemplary embodiments, the bag 2701 can be inserted into the housing 2702 of the system 2700 such that the bellows actuator 2804 is operably connected to bellows chamber 2722. As shown in FIG. 28A, pathogen nucleic acid 2812 can be isolated in a collection chamber 2734 by one or more earlier operations, as those having ordinary skill in the art will understand from the description above with reference to FIGS. 18-26. A snap lock 2814 can be provided to function as described below.

In FIG. 28B, the bellows actuator 2804 is shown pulling on bellows chamber 2722 such that liquid (including pathogen nucleic acid 2812) in the collection chamber 2734 is sucked through a one-way valve 2733 and into a receiving chamber 2762. Furthermore, a filter frame, such as frame 2728 shown in FIG. 27B, is pulled into snap lock 2814 that fixes the filter location, for example, the location of filter 2726 shown in FIGS. 27B and 28C.

In FIG. 28C, electrophoresis resulting from applying power to and thereby generating an electric field between the electrodes 2724 and 2730 may move pathogen nucleic acid 2812 through the filter 2726 and into a second collection chamber 2736. In FIG. 28D, bellows actuator 2804 changes direction and pushes to collapse the second collection chamber 2736, forcing the liquid, including nucleic acid 2812, through a one-way valve 2732 and into a collection vessel (not shown). One-way valve 2732 can comprise, for example, a duckbill check valve or the like.

According to various exemplary embodiments, an electrophoresis-based sample preparation system comprising a bag such as, for example, that shown and described in the exemplary embodiments of FIGS. 27 and 28, can eliminate washing of the automated processing device between runs (e.g., preparation of differing samples). The bag can be disposable thus eliminating the potential for cross-contamination between samples.

According to various embodiments, the bag can comprise one, or more than one, layer to protect and guard against static charges inside and out. For example, the bag can comprise a polyester outer layer featuring a semi-conductive, static-shielding coating. In some embodiments, the bag can further comprise a non-shedding metallic middle layer to provide an electrical transference barrier. In some embodiments, the bag can further comprise a thick anti-static, polyethylene inner layer that suppresses static inside the bag while resisting punctures and tears. The bag can be transparent for easy content identification. In some embodiments, the bag can comprise a zipper closure.

In the various exemplary embodiments described herein, the filters can comprise, for example, a separation medium, such as an electrophoretic separation medium, and/or a size-exclusion material, examples of which have been described herein.

Unlike conventional electrophoresis used to separate differing nucleic acids by length, in the exemplary embodiments described herein, precise timing of the electrophoresis migration (i.e., the duration of time the electrodes are activated) may not be necessary. However, knowing the length of the target nucleic acids in advance may facilitate in maximizing the amount of the target nucleic acids isolated and collected by permitting determination of a sufficient amount of time to activate the electrodes.

Various exemplary embodiments of electrophoresis-based systems used for extraction, isolation, and collection of nucleic acids in accordance with the present teachings may significantly reduce the amount of time to isolate and detect the presence and/or kind of nucleic acids in a sample as compared to conventional techniques used in a variety of applications. The disruption and electrophoresis separation steps may take from about 5 minutes to about 60 minutes, for example, and may yield a nucleic acid sample amenable to detection via PCR, which may take from about 30 minutes to about 120 minutes. Thus, the electrophoresis-based systems in accordance with exemplary embodiments of the present teachings may permit nucleic acid detection in a matter of less than an hour to about 2 hours, as compared to several hours, e.g., up to 8 or so, for conventional procedures. The various time periods provided herein are approximate and may vary depending on numerous factors, such as for example, sample size, the type of cells in the sample, the type and/or amount of material for which isolation is desired, etc. As such, it should be understood that the invention is not intended to be limited by the particular time periods discussed herein.

Suitable electrode materials in accordance with the present teachings include, but are not limited to, platinum, silver, copper, aluminum, electrically conductive plastics, and/or any other electrically conductive materials suitable for making electrodes. Further, in various exemplary embodiments, it is contemplated that the charge of the electrodes may be reversed if desired to prevent nucleic acids from entering the filter used to capture and/or separate negatively charged particles smaller than the nucleic acids in the event such filter does not block the passage of the nucleic acids. Moreover, as has been described, the various electrode configurations described herein are not intended to be limiting and those having skill in the art would recognize a variety of other configurations that may be used without departing from the scope of the present teachings. It may be desirable, for example, in various exemplary embodiments to provide an electrode that is common to each of the sample chambers, for example, in a multi-chamber titer plate format, rather than providing a plurality of electrodes for the respective chambers. However, in cases where differing electrodes are used for each chamber, it may be desirable to have each electrode independently controllable so as to independently control the electric field generated in each chamber.

In various exemplary embodiments, it may be desirable to add agarose or other thickening agent to the disrupted samples in order to increase the electrophoresis forces relative to diffusion forces acting on charged material in the sample chamber.

Those having skill in the art would recognize that the various exemplary embodiments describing operation of the various electrophoresis-based sample preparation systems may be modified to achieve extraction, separation, and isolation of a variety of sample types containing various material (e.g., number of types of entities containing nucleic acids). Thus, it should be understood that the number of disrupting and/or electrophoresis separation steps may be modified depending on the number of differing types of entities containing nucleic acids (e.g., pathogens and/or other cells) and other factors, for example, the desired level of purification (isolation) of target nucleic acids from other entities in a sample. Those having ordinary skill in the art would understand that features, components, and/or materials described with respect to a particular exemplary embodiment may be used with another exemplary embodiment and modifications made accordingly. It is to be understood that the particular examples and embodiments set forth herein are nonlimiting, and modifications to structure, dimensions, materials, and methodologies may be made without departing from the scope of the present teachings.

Other embodiments of the present teachings will be apparent to those skilled in the art from consideration of the specification and practice of the present teachings disclosed herein. It is intended that the specification and examples be considered as exemplary only, with a scope being of a breadth indicated by the claims.

What is claimed is:

1. A system for collecting target nucleic acids from a sample, the system comprising:

at least one sample chamber configured to receive a sample containing target nucleic acids and other material;

at least one collection chamber removably mountable relative to the at least one sample chamber and configured to collect target nucleic acids separated from the other material;

a filter removably mountable relative to the at least one sample chamber and configured to be disposed between the at least one sample chamber and the at least one collection chamber when the at least one collection chamber is mounted relative to the at least one sample chamber; and a pair of electrodes configured to generate an electric field sufficient to cause target nucleic acids in the at least one sample chamber to migrate via electrophoresis from the at least one sample chamber through the filter into the at least one collection chamber, wherein the filter is configured to permit passage of target nucleic acids and to block passage of material of a size larger than the target nucleic acids;

wherein a first electrode defines with the sample chamber in a dome configuration with a closed bottom end and an upper open end and a second electrode associated with the collection chamber such that the electric field is generated in the at least one sample chamber, the at least one filter and the at least one collection chamber.

2. The system of claim 1, wherein the filter is disposed within the at least one collection chamber.

3. The system of claim 2, wherein the filter is configured to be removed from the at least one collection chamber to remove the target nucleic acids from the at least one collection chamber.

4. The system of claim 1, wherein the filter and the at least one collection chamber are configured to be removably mountable together relative to the at least one sample chamber.

5. The system of claim 1, wherein the filter at least partially defines the at least one collection chamber.

6. The system of claim 1, wherein the at least one sample chamber comprises a plurality of sample chambers defined by a titer plate and wherein the at least one collection chamber comprises a plurality of collection chambers, each collection chamber corresponding to a respective sample chamber.

7. The system of claim 6, wherein the plurality of collection chambers are defined by a titer plate.

8. The system of claim 6, wherein the plurality of collection chambers comprise a plurality of dispenser tips.

9. The system of claim 1, wherein the at least one sample chamber comprises one sample chamber having a volume ranging from about 1 ml to about 1000 ml.

10. The system of claim 1, wherein the at least one sample chamber has a volume ranging from about 1 ml to about 1000 ml, and wherein the at least one collection chamber has a volume ranging from about 10 microliters to about 1000 microliters.

11. The system of claim 1, wherein the filter is configured to permit passage of pathogen nucleic acids and to block passage of host nucleic acids.

12. The system of claim 1, wherein the filter is made of a material selected from beads, fibers, perforated metals, and porous gels.

13. The system of claim 1, wherein the filter comprises an agarose or polyacrylamide gel.

14. The system of claim 1, further comprising a second filter configured to permit passage of particles having a smaller size than the target nucleic acids during migration via electrophoresis while blocking passage of the target nucleic acids from entering the second filter.

15. The system of claim 1, wherein the target nucleic acids comprise deoxyribonucleic acids.

16. A system for collecting target nucleic acids from a sample, the system comprising:

at least one sample chamber configured to receive a sample containing target nucleic acids;

at least one electrophoresis matrix comprising at least one collection chamber and at least one filter, the at least one electrophoresis matrix configured to be removably mountable relative to the at least one sample chamber such that the at least one filter is disposed between the at least one sample chamber and the at least one collection chamber;

a pair of electrodes configured to generate an electric field sufficient to cause target nucleic acids in the at least one sample chamber to migrate via electrophoresis from the at least one sample chamber through the filter and into the at least one collection chamber;

wherein the pair of electrodes comprises a first electrode that defines the at least one sample chamber in a dome configuration with a closed bottom end and an upper open end and a second electrode associated with the collection chamber such that the electric field is generated in the at least one sample chamber, the at least one filter and the at least one collection chamber.

17. The system of claim 16, wherein the at least one sample chamber comprises a plurality of sample chambers defined by a titer plate and wherein the at least one collection chamber comprises a plurality of collection chambers, each collection chamber corresponding to a respective sample chamber.

* * * * *

UNITED STATES PATENT AND TRADEMARK OFFICE

CERTIFICATE OF CORRECTION

PATENT NO. : 8,568,580 B2
APPLICATION NO. : 12/179455
DATED : October 29, 2013
INVENTOR(S) : Vann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1320 days.

Signed and Sealed this
Fourteenth Day of April, 2015

Michelle K. Lee
*Director of the United States Patent and Trademark Office*